(12) United States Patent
Zwiebel

(10) Patent No.: US 7,141,649 B2
(45) Date of Patent: Nov. 28, 2006

(54) MOSQUITO ARRESTIN 2 POLYPEPTIDES

(75) Inventor: Laurence J. Zwiebel, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 417 days.

(21) Appl. No.: 10/094,240

(22) Filed: Mar. 8, 2002

(65) Prior Publication Data

US 2003/0082637 A1  May 1, 2003

Related U.S. Application Data

(63) Continuation-in-part of application No. 10/056,405, filed on Jan. 24, 2002.

(60) Provisional application No. 60/264,649, filed on Jan. 26, 2001.

(51) Int. Cl.
*C07K 14/00* (2006.01)
*A61K 38/16* (2006.01)

(52) U.S. Cl. .................. 530/350; 424/198.1; 514/2; 514/12; 530/324

(58) Field of Classification Search ............. 424/198.1; 514/2, 12; 530/300, 350
See application file for complete search history.

(56) References Cited

U.S. PATENT DOCUMENTS

| | | |
|---|---|---|
| 5,011,909 A | 4/1991 | Borovsky et al. |
| 5,030,722 A | 7/1991 | Snyder et al. |
| 5,128,246 A | 7/1992 | Snyder et al. |
| 5,130,253 A | 7/1992 | Borovsky et al. |
| 5,439,821 A | 8/1995 | Borovsky et al. |
| 5,501,976 A | 3/1996 | Borovsky et al. |
| 5,629,196 A | 5/1997 | Borovsky et al. |
| 5,670,354 A | 9/1997 | Burns et al. |
| 5,702,916 A | 12/1997 | Molin et al. |
| 5,993,778 A | 11/1999 | Firestein et al. |
| 6,008,046 A | 12/1999 | Ffrench-Constant et al. |
| 6,071,878 A | 6/2000 | Delecluse et al. |
| 6,610,511 B1 | 8/2003 | Carlson ............... 435/69 |
| 2002/0064817 A1 | 5/2002 | Buck et al. |
| 2003/0045472 A1 | 3/2003 | Axel et al. |
| 2003/0143679 A1 | 7/2003 | Vosshall et al. |
| 2003/0186359 A1 | 10/2003 | Vosshall et al. |
| 2004/0003419 A1 | 1/2004 | Carlson .............. 800/8 |

OTHER PUBLICATIONS

Pierce et al. (2001). Classical and new roles of B-arrestins in the regulation of G-protein-coupled receptors. Nature Reviews. 2:727-733.*
Fukuto et al. (2004). G protein-coupled receptor kinase function is essential for chemosensation in C. elegans. Neuron 422:581-593.*
Dolph, P.J. (2002). Arrestin: roles in the life and death of retinal neurons. The Neuroscientist 8(4):347-355.*
McDonald et al. (2000). B-arrestin 2: a receptor-regulated MAPK scaffold for the activation of JNK3. Science 290:1574-1577.*
Gurevich et al. (1995). Visual arrestin binding to rhodopsin. The Journal of Biological Chemistry. 270(11):6010-6016.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 492-495.*
Bentrop, et al.; *An arrestin homolog of blowfly photoreceptors stimulates visual-pigment phosphorylation by activating a membrane-associated protein kinase*; Eur. J. Biochem (1993) 216: 67-73.
Boekhoff, et al.; *Termination of second messenger signaling in olfaction*; Proc. Natl. Acad. Sci.; Jan. 1992; 89: 471-474.
Clyne, et al.; *A Novel Family of Divergent Seven-Transmembrane Proteins: Candidate Odorant Receptors in Drosophila*; Neuron, Feb. 1999; vol. 22, 327-338.
Fox, et al.; *Candidate Odorant Receptors from the Malaria Vector Mosquito, Anopheles Gambiae AND evidence of Down-Regulation in Response to Blood Feeding*; PNAS, vol. 98, No. 25, Dec. 2001, 14693-14697.
Hyde, et al.; *Twenty Drosophila visual system cDNA clones: One is a homolog of human arrestin*; Proc. Natl. Acad. Sci.; Feb. 1990; 87: 1008-1012.
Levine III, et al.; *Isolation of a Novel Visual-System-Specific Arrestin: An In Vivo Substrate for light-Dependent Phosphorylation*, Mechanisms of Development, Dec. 1990, 1:19-25.
Merrill, et al.; *Visual Arrestins in Olfactory Pathways of Drosophila and the Malaria Vector Mosquito Anopheles Gambiae*; PNAS, vol. 99, No. 3; Feb. 5, 2002; 1633-1638.
U.S. Appl. No. 10/056,405, filed Jan. 24, 2002, Zwiebel.
Merril et al. Visual aarrestins in olfactory pathways of Drosophila and the malaria vector mosquito Anopheles gambiae. Proc. Natl. Acad. Sci. USA. Feb. 2002, vol. 99, No. 3, pp. 1633-1638.
Merril et al. Molecular characterization of arrestin family members in the malaria vector mosquito, Anoopheles gambaie. Insect Molecular Biology, Dec. 2003, vol. 12, No. 6, pp. 641-650.
Xu et al. Identification of a distinct family of genes encoding atypical odorant-binding proteins in the malaria vector mosquito, Anopheles gambiae. Insect Molecular Biology. Dec. 2003, vol. 12, No. 6, pp. 549-560.

* cited by examiner

*Primary Examiner*—Christine J. Saoud
*Assistant Examiner*—Jon M. Lockard
(74) *Attorney, Agent, or Firm*—Wyatt, Tarrant & Combs, LLP

(57) ABSTRACT

The invention discloses a polynucleotide and polypeptide of arrestin 2. Also disclosed are methods for producing such polypeptide. This invention also discloses a method of identifying compounds that bind to arrestin 2 or odorant receptors. A method of identifying compounds that inhibit the binding of mosquito arrestin 2 to a mosquito odorant receptor is also disclosed.

2 Claims, 19 Drawing Sheets

Figure 1

*Anopheles gambiae* odorant receptor 1 genomic sequence (SEQ ID NO: 9)

Features:
1) Presumed Untranslated 5' and 3' regions are underlined.
2) Potential TATA box transcription initiation signal is double underlined.
3) Putative Start (ATG) and Stop (TAA) codons are in BOLD.
4) Introns are tentatively assigned and are shown in lower case.
Exons are highlighted.

```
AGCTTTGTTCATTTATGTTGAAATCTAGCCCATTTTGTATAGTGCTGAACGACGAAGAACATAC
GAAAGTACCTCGTCCGAACACTATCAACATTAATTATACCAAGCTAGAAGAAGATATTTATAGT
CAAGCCTCAACATCATAGGAAACTTTAGCAAAACCATTTAATTTACATGATGATAAGTCCCACC
TCTTACCCCAGCACAGGTTTGAGAAGGACGAAAGTATCTTTACGATAATATTACTCTAAGGTAG
TTTTTGAATAAAATAAAAATTTACGTGCAAGTGGTGGCATCGGACATCATTCGAAAGAATCTAC
TAAGTCATACACACACCCAAGACGACCGACGTAGTTTCATCTAGAAAAAACGGGTCAGCTCCAT
CGAACACGTCAGGACATAACTGCGACATGCGTATGGTCAGTTCCACTAGTGCCAACACTGGTTC
CAGGGCACTACCTTCCGAAGCAGTAGAACCTAATGTATTGGAAATTATTAGGACATACTGCAAC
ATGCATATGGCTAGTTCCGCTGGTACCAACGATGGCACCAGGACACTATCTGCGGCCTTGTAAA
ATCACTGTAAAATCTATACAAAAACGGCTTTACCCATACTTTATCACAAAAACGGCAGGTGAGG
GCTGGATTGCTTCAAAGCATTAGAAATATATAATTTCAAAGTCCATAATCTCCTTAAAAGATAG
ACAaCAGTAGAGAACACATTTAGTGCTCTTTTCGTTCGAGTTAGTTGCCTTCTCAAGTAAGCGT
TTAATGCTCAATTGTTGTAGATTCGTTGGATGACTCTCGCTACGTGCTATAGTGGTCAATACTT
CCAATTAGATTTCATAATTAGTTTCCAATTGTCCACGGAAAACCCaCAAAAGAAAAAAAAACTT
GTATCTAGGGTGGAATTTTTCGAGAACAATTGGACACTTCATATGAAAAACGACACGCTTTTCA
AAATGCTTAAATAAACAGCCGTTGCCATCCTTTgttggatttcaattctccaaattctgcagaataa
ttctgcaaatttacaaaactgctcaaccaccaataattccaattaatcatctgaacatttaaa
actgataattaagatgagtaattgcttcgtcatcacctaagaaatcgattagtttggataaaaa
gaacaaattgaaatacaataaagtccctgaattttattcgaataacggcttgaactcatttatt
tcaaaaacctttgagaaattcctcgttgaaaattggtctcctatagttctgctaacgggccact
tcaaagcaagaactaacaaaatcataattatggtgcaagtaactatcagtaccagtaatcgcc
attaaaaacttttcctcaatttgcggctcgttaccggctaaatacagagcagagtaacgggaag
tgatcaacgtcgctattagtataacgaggaacgccctccgaaggtgtgttgaaggacctttca
aattgaaaccaagtactgtttccagttttaaattggatagttataaaatgagccgttcaacgat
cgggcatcatttgagtttcatcttcgaggagaaatagatcagtgccactgtttaaccgaaagta
atgaagctgaacaaactgaacccacggtgggatgcgtacgatcgacgggattcgttctggttgc
agttgctttgtttgaaatatttagCCGTATCCCCACGGGAAGATACCGATCACGGAACGCGGAA
CGGGTACATCGCGTACGGTTGCCGCTTTCCCCATCATGTTTCTACATCTCTACGCTCTAACGCA
GCCGTATACTTCAAGCgATGTGAAGGATATTAAIgtgagtctctagttagctattagtgttccac
ctgtccataatctgtctttattgggtagGACATCGGAAATGCATTGTTGCCTGCTTATCACTCA
ACTGACCTCGATCTAGAACGCTGGAAACTTTAACTACAACATCGCAGGCATTGAGCCGTTGCTG
```

GGCAAGGTTAACTGGACACTGTATGACGCCGAAACACGCCGAAGAATTCAGgtaagcctgctggg
aaatatgactaaaaagagtgctaacaaacgactctcctccaaatgtagCCCGTTTTACAATCG
ATGAGTGGAGTGTTTTGCCTGATGATCTTTCTCATGTTTGTGGCTATCTTCACCATCATCATGT
GGCTTATGTCGGCCAGCCTTCGACAATGAACGTCGTCTGCCCGTGCCGGCCTGGTTCCCGGTCGA
CTATGACCATTCGCACATAGTGTACGGTCTACTGTTCCTGTATCAAACCATTGCAATCGTCATC
AGCCGAACCTACAACTTCTCGACCGATACCATGTTTTCCGGCTTGATCCTACACATAAATCGAC
AAATTGTCGCCGTTCCTACTATGCTTAAAAAGgtgagttacggcgactacttgcctccagtaag
gacagggagtttgtttccgttatgatatcattttatcagCTTGGACATGACGTCCGTCGCGAAC
GCCAATTGCTCGCAACGGATCGCGAATGGAAAGAGATGCGAAAGCGCATCGACCATCACTGCAA
ACTGTACCGTACCATGTACCGTAAACTAACGGACTGTGTGGCTGTTTCACAAGGACATGTTAACg
tacgaattgggccaattaattgtgtcatttaaaaagcttgacccaactttttcacagcttcggcg
atgaagtgcaggacatttttccaagGATGTATGTTCGCGGCAACTATGCCGCTCTGTAATTATGAT
TTGTATGACACTGCTGGAACTACCGGCGCGATGTTACGATGCCGATCTGCTCGGCTGTCGGC
TGTATTTTGCTAGTAAAGACATCGGCAACTGTTTATTTTCTGTTACGTAGGCAATGAAATGTCGTA
TACCgtaggttggacacgtagaggaattaaatgtttgggaagaatatcaataccaaatagtatg
atgtttcgttacagACGGATAAATTTAGAGAGTTTGTTGGGTTTTCCAACTACTTGAACTTCGA
TAAGCGTACCAGCCAAGCAATGATATTTTTCTGCAAATgtgagatagcggtgtatttgtgcag
tcagtacattaaatacgttctctatttcagGACTGTTAAAGATGTTGACATCAAGGTCGGAAGT
GTCTTGAAGGTTACGCTAAATCTTCACACATTTTGCAGgtatgtaattatgctgtggtattta
gcttgaaataagctacaaactttgaaagtaatttcaatctgttttgtagATTATGAACGTATCG
TACTCGCTATCTGGGCGTACTTCACAGCATCGAATCAGAGTAATCGTCGTAATATCCGTAATGTT
GAAATTATATTTTGTTAGATTTATTGCATAAAGTAaTaTTTAATTTTATACATCAAACGTAAGC
CCGCtaGTTTTCAATTAGCCTTTTTCCAAAATTTATCAAATTGATTTCGAATTGATTGCAGAGTT
TCAGGAATTTAATCTGATAGGATATCTTGTTTATCCAATAGAGGTGTGGAAGCGTTCCCAAGCC
ATTCGTTTGATAGTTTATAGCACCGTCGAGCAGTTGATCGCTGTGATCGCTAGGCGCACCTGAT
TTTATCTTTATCTCGCACCTGTTATGGCAAGGGCGCTTTTCACACGTTTCACACAATATAATGC
ACATGTATAATGCATTCTTACTTTAGCATTTTTGTTACATATAATACCAAAATTATGCATTTTT
ATTCTCACGCAACGATTAGAGGATGACTTcACAAAGGTCCATCTAGTGGTAGGAGGTATACAAT
TATACCTCTCAAAATCTCACAGCAtAATGAGAAACAAAAGGATACCAAGCATACCCTTTTTTA
CTTGACAATTTCATTTGATTTATGTAATAAAGCACTGCaCGTCGACTTCCTAAAA

*Anopheles gambiae* odorant receptor 2 genomic sequence (SEQ ID NO: 10)

Features:
1) Presumed Untranslated 5' and 3' regions are underlined.
2) Potential TATA box transcription initiation signal is double underlined.
3) Putative Start (ATG) and Stop (TAA) codons are in BOLD.
4) Introns are tentatively assigned and are shown in lower case.
5) Exons are highlighted.

```
GGGATCCTCTAGAGTCGACCTGCAGGCATGCAAGCTTCCCTCACCGTGACGTGCTAGAAATGGT
TCAACATACTCGTCCGGCAGAGCGAAGACGACGAACAGCGGAATGTCCCAGGAAATGTAATGAG
ATATCACAGCAAGTGAACCCAAACCGAGCTGTGCGCTTTGTGTTGCGCTTTAAAAATGGCCCTT
CCTTCGCCGCATCTGCTTGGTTTCACACGCTTTCCCAGGAAATCCACTGACCACTGGCCACACA
TCAACCACCGGAGCGGGAGCCTCAGTGCCCAGCGAAGCATATAATTTGCTCAAAAAGTCACGGT
ACTCAATTAATTTGATTATAATCAATTTCGTGGCTTCCAACACACCCTTCTTCCACAATCCATC
GCCGAGTGAGCGAGTATAAAGGTGAAGAAACGTACCTTGCGCTTGCTCACTAACTGAACCGGAT
TTCAAAAAGGAACATAAACCGCAACCCACAGCCGAAAATGCTGATCGAAGAGTGTCCGATAATT
GGTGTCAATGTGCCGAGTGTGGCTGTTCTGGTCGTATCTGCGGCGGCCGCGGTTGTCCGGCTTTC
TGGTCGGCTGCATCCCGGTCGCCGTGCTGAACGTTTTCCAGTTCCTGAAGCTGTACTCGTCCTG
GGGCGACATGAGCGAGCTCATCATCAACGGATACTTTACCGTGCTGTACTTTAACCTCGTCGta
cgtgggcgaggggaggggcaataaccttcccacttggtggatattttcataccttttccatgtg
tttttttattctctgtttgttgccatccagCTCCGAACCTCCTTTCTCGTGATCAATCGACGGA
AATTTGAGACATTTTTTGAAGGCGTTGCCGCCGAGTACGCTCTCCTCGAGgtaagtcattggtt
tttctagttttgggggagttgtttacaccataaccaccccgacggtaacatttgatcgtccc
gcgaaaatgtttgtacagAAAAATGACGACATCCGACCCGTGCTGGAGCGGTACACACGGCGGG
GACGCATGCTATCGATATCGAATCTGTGGCTCGGCGCCTTCATTAGTGCCTGGTTTGTGACCTA
TCCTCTGTTTGTGCCCGGGCGCGGCCTACCGTACGGCGTCACGATACCGGGCGTGGACGTGCTG
GCCACCCCGACCTACCAGGTCGTGTTTGTGCTGCAGGTTTACCTTACGTTCCCGGCCTGCTGCA
TGTACATCCCGTTCACCAGCTTCTACGCGACCTGCACGCTGTTTGCGCTCGTCCAGATAGCGGC
CCTAAAGCAACGGCTCGGACGCTTGGGGCGCGACAGCGGCACGATGGCTTCGACCGGACACAGC
GCCGGCACACTGTTCGCCGAGCTGAAGGAGTGTCTAAAGTATCACAAACAAATCATCCAGtaag
tagacgctagtagactcgaccggattgcccttccctcggggaggggaggtttgctatttcggga
tgcggcagcacgcatacacacaaaccggaagccattaattctcccgttttcatgcccgcacggg
cactgggtcatgtttcacatccttccttcctttccaaacacacacacgcgcgcgtgcacgtaca
gATATGTTCATGATCTCAACTCACTCGTCACCCATCTGTGTCTGCTGGAGTTCCTGTCGTTCGG
GATGATGCTGTGCGCACTGCTGTTTCTGCTAAGCATTGtaagtaaaatcgaccgacgtgcggtc
gctagtccgtctccggactctcatttcgggactcaatcgttccatctctcaatagAGCAATCAG
CTGGCACAGATGATAATGATTGGATCGTACATCTTCATGATACTCTCGCAGATGTTTGCGTTCT
ATTGGCATGCGAACGAGGTACTGGAGCAGGtaatggcgctgaagctgagtttggttgagcggtt
cgctatagatcggctgtcttacattgttgtgtttctgcatggggatcggttttgttttcctct
```

```
ccatttcagAGCCTAGGCATTGGCGATGCCATTTACAATGGAGCGTGGCCGGACTTTGAGGAAC
CGATAAGGAAACGGTTGATTCTAATTATTGCACGTGCTCAGCGACCGATGGTGGTAAGtttggc
tgatcgatgctctgttcaatgaacatggcacagaaggctgtgtaaatagctgttcattaataag
ttttttcagaatgtatcgtttttagttgatttaaacgcattgttctatgcaatggtagcaacaa
tagaccgcctttattaatccaagcttcctttaggattgattttttattttaagagaaagataaac
cattttagtaaccaatttagttacaggaaccaaaatacagaatttattattattattattatt
attattattattattattattattattattattattattattattattattattattattatta
ttataattattattattattattattattattattattattattaatattattattattat
tattattattactattattattataattattactttattattattattattattattattatt
attattattattattattattattattattataattatgattattattattattattatta
ttattattattattataacaataataattattattattatttattattaattaattaatttatt
attattaattattattattgttattcattattatacattattatcataataatttattat
gattattattattattattattattattattattattattattattcttattattattatt
attattattattaatattattttaatattattattattattattactattcttattataa
ttattttttttattattattattattattattattattattattattattattattgcta
ttgttattattattcttattattgctattgttattattattattcttattattgttgttgttgt
tgttcttattattgttgttgttgttattcttattattgtttattattattgttttttttttattc
tctaattattccagtaatccataataaaaataataaagtaaataaatagtaaatagtaaataa
ttccagtaactgtagtaatacacaataatctctaagaattaaaattgcatttgtaatgaaata
tgttgattgttcgaatagttcagaaaaacttaaaaatgcctcagcattaaacagttttgaggtt
gttcagggcatttagtttagatattttagtattttaaagcatttgttttcattactacaaaaaa
gcaaatttatgagtgaattactttcagttcttctaaacgcctatgtgtatgcaattacataaca
atagctctcttttttattgcattttccttagtaatctaaatccaatctcttcttttcctcttg
cagATTAAAGTCGGCAACGTGTACCCGATGACGTTGGAAATGTTTCAAAAATTGCTCAACGTGT
CGTACTCCTATTTCACACTGCTGCGCCGAGTGTACAACTAAACTTAACCGGTAAACAAACAAAA
ATCCCCTCATCACTATGCAAAGACAGCAAGCAGCCGATCATCAAACACCATTAGCAGCCACAAA
GTTACCAGCCGCTTATCCCACGGGATTTGGTGGAAAGTTATTGCACTGAAGCTCTTTCACCCAA
ATTTTCATGGAGGTTCCCTCTCAACCAACCCATTGAAGCGAATAAAAGTATCAGCAACCAGGCG
ACGGTGAAAAAACGCTGCATTATTGTGCTTGCTTCAGCATTCCAGCGAATGACTCTTAAACTTT
TCCATTCAAAAGTCGCGATGCTCACGATACGGAGCGGTGTGTTGTTCGATCCGCCGAGTGCACT
CGCAAGCCGGTGATGTTGCCGGTGGAAATGCACAGATCGACACAGCGATAGATAATCGTTTGTT
CGCGTAAATGGGAGGGAAAAAAGTAAGCTGCCAGCTACTTCATTTCCATGTTAATTGAAACTCA
AGCCAACGAACATGCAGAACCCGGTTGGTTGTGTGTCTCCGCTCCGGGAAAGGTCTCTGCTCCG
GGGCATGGATTCTTTCCCCCTCCGGGTGGTTGGGGGTATTGTTTAGGTTTTTATTTTACAAATT
CATATCCTTCCGCTTCCGCATCAGCCGACCCGGTGGGTGCGCCAGACAGATGTGCGGCGGGCAA
CAAAACTATGCACGAACATGGCCAACAAACACAGCTTCTATCTCATCTCTGTGTCGCACTGTCT
CGCTTTCCCGCTGCGTTGCTTGTAGTACTATCATTGTTTTAGTCCACGGGTTTACTTCTAATTC
CATTGCACCACGCAAAAAGGCTCATCCTTTGCTCGTTCCGGTTGCAACTTCGACAAGCGCATGG
TTGGGATACGAACAAAAAACCAACTACTCCACCCACTACTACTACTACTGCCACCACCACTAAC
AACACTACACTTGGTTGGGAGCTTGCAGACCCACAAGCAAACAACGATACAAGCTAGCTAGCTG
CTGTGTGCGCTCGAGTCAGCCGACGGTACAAGGTTTAACCGGTACAAGCAACTCCCGGACCGAT
CCCAAAACTCTGACAAGGCACGGGGCCGCATCCGGCAGTACGGTCGGAAAACATGGAAATGTTT
AATTAAAACTGTAATTGTCAATCGCTGCTACAAGTTGTGACACAGGGAGAGAGAGAGACAGAGC
GCGCCCGATGGTGATGGTGTAAAAGATAGATACAGGAAAAGAGCGAGAAACATTGGTACGATTT
```

GGTGTGGTTAGCAAATTTGATTTCCACTGATTTTGAGTGCAAATTTAATGCATCGAAAATTTGC
CATTCAGGGTAAAGTTGCTCGTGGACGGATCCCCCGGGCTGCAGGAATTCGATATCAAGCTTAT
CGATACCGTCGACCTCGAGGGGGGGCCCGGTACCCAGCTTTTGTTCCCTTTAGTGGA

*Anopheles gambiae* odorant receptor 3 genomic sequence (SEQ ID NO: 11)

Features:
1) Presumed Untranslated 5' and 3' regions are underlined.
2) Putative Start (ATG) and Stop (TAA) codons are in BOLD.
3) Introns are tentatively assigned and are shown in lower case.
4) Exons are highlighted.

```
AAGCAGAACACATCAAGAAGCAATTAGGTGTGTCGTACGTTAGCAAGTAGTTCGCGAGGAGGAATAAAATAGATGCG
TTGTCAGCGGGTTGCTGTCATTAGTTCCTTCGGAACTGCTCATGACAATAGCACGATGCTATGCCAAAATTAAAGC
ATGAAACAGGAGTGATGCCGTTTCTGCTGCAAATTGAAACCATGCCGGACTCTCCCGTCAGCGTTCCCAGCCCTAC
CGTTTTTATCTCATCTTTTCCTACTTCTCGCCGATCGTGCTTCTACCGAAACTGCTGTTCGGTAATCCACATCTGGA
GGTTCCCGTACCGCGGACCGGCCGAGCTGATGTTCGAATCGAACGCATTCTTGCGGATGCTAATCGTTTCCTTTCAAC
CCGACAACTACGAGCGATTCCTGCATCACGTTGCAGGATCTCGCAGCTCTAGgtgagtatgcagccaatcgattgttc
caaacctttcgcaacatccttcgtaacactgctacactttcagTCCTCCAAGACCTACGCACAGAGCCTGGGAGACTAC
CTGATCTCAGTCAACCCGACCGGTCGATCCCTTCTGCAAAATTTACTGGTGCTGCTCACTTTTCCATGCCAACGTTCTT
TTGCTTCATCCCCGTCTCGGACCACGTATTCGGCCTACTTTCCTGTCCGAACAGCACGGAAGGCTCCAGCACCGTCTT
TGCACCTCCAGGAAGAGCTCTACTTCCTCAACATTCCGACTTCCATCGGCCTATATACCTTTTTATGTCCCATTATC
TGCCCCACCATCTATACCGCTCCGCTTTACCGCTGCCAGAAAGCTCGTCACCCATTTTCACCAATCTTACTACTCTTG
GGCCATGCCTGAAGCTGCTTGCACTCCGAATCCACTGTCTAGCGAGACTACGGCAAGACCCACCGCAAATAGGACGTCCA
ACCAGATTATTTCCATCCATCAGCCGGCTACTCAAgtaagtaaattcaaattgaaagttttgcagggaataacttgag
tgtgtctgacccgtgcacatcctagCTGCCGTCTTCGCTGCCTCGAGACGACATTCGGCTGGGTATTTTCCGTCCACTTC
ATTCACTGTACAATCATCTGGTGCAGTCTCATCCTCTACATACGCCTCCACgtaatagcattttcgtcatttcgtta
gccttattcaatccattttttgtgaacgtgaatttcccccagCGCTTCAGCCTCGACCCTAGCCAATCTATCTCTCCAG
ATGATTTCGCTGACGGTCCAAACTTACCCTACGGCTACTTCCGAACACATCTAACCACCACCGTCCTTTCgtacc
ctttggatgaagcttcaaaaagtaattccaaattctgttttcgattttttccccttttccactagACCTATGCCCTTC
CCCTCGGCATTTACCATACCCAGTCGTACAAGTTTTCCATTTCGATCCCCGGCAAACTTCGACTGCTACTCCAAACGA
TCCCAAAAACCGCTCGCCCTAACCGCCGCGAAAGCTTTCGCCTTCGTCAATCGTCGCCAGTTTGCCCAGgtaacattaat
tacagtttgaaaattctgaagaatgcatcttacttgccttacttgttgttccagATGCTGAAGATGTCCTATTCATT
TTACCTACTACTCAACCACCACCTTCTTAGGAGCTGCTGTTTCCCACCCTGGAAATGGCCTTTTCGCACTGTCTTCTGT
TTGTTGGACGCACGCAGCACCGAGAGCGCCCCTGCACGCACTGACGTATTTTGGCTACTTTGACGTTTGCACCTTTG
ACAGCTGAAGGACAGGGTACAATTTTTGCTGCTGTTATTACGCGCAGCGCATTGGATACGAAAACATTGGCCACAAG
TTCTACGATTTTAGCGTTTATTTACTGTTCGTAGCAGCTTTTTTCCaCAATAAACACACACAATAACGTACCGACAG
TATTCTTTTCATTGTAGGATAGAGAAGCCGCCGGCCAGCAGCCAAAACGCGCCGCAAAACGAAAGGCGGCACCACCG
GGGGAAAAACACGGGAGCAAAACGAGAACAGAACGCAGTAAACAACAAAACCGGCCGGAACAACAACGGTGCCGGAA
ACGA
```

Figure 4

*Anopheles gambiae* odorant receptor 4 genomic sequence (SEQ ID NO: 12)

Features:
1) Putative Start (ATG) and Stop (TAA) codons are in BOLD.
2) Introns are tentatively assigned and are shown in lower case.

GGGGAACTCCCCCACCCGACCAGACGACGGAAAGCTAACGATGTGCAATTGAATAGTCATTAGT
AGCGTTTTTGCTCGCAAACGAACTAACCCTTTGACTTTTTAAGTTCACTACGGTGAGGACAAAAA
TCAATAAATTAAATCGAGACCGTTGATGAGCAAAAGAAAAAAAAATATTTTACTGATTTTCATTT
CGTTCCATCGACTACATAATCATAATTATATGCCACATTTTATTATAAGTTTTTGTATCATTTTTA
AACAACACAAAAATGCATCCTTTCGAATATTAGTCAGGTTGTATCAACAATGAAGTTTGAACTGT
TTCAAAAATATTCCTCCCCGGACACGGTCTTATCCTTCGTGCTAAGGCTTTTGCATATCGTGGGC
ATGAATGGGGCAGGATTTCGGTCGCGAATTCGAGTTGGTGGCATTTTTCTGTTCTATTTAATCTT
TCTTGTAATACCGCCACTAACGGGCGGGTACACCGATGGTCACCAGCGTGTACGCACCAGTGTG
GAATTCCTGTTTAATTGCAATATTTACGGCGGCAGTATGTTCTTTGCCTACGATGTGGCCACTTT
CCAAGCGTTCATCCAGGAACTGAAGAGCCTTTCGGTTTTGGgtaatatttaattaattaaaattgcgtttattgcat
catcatttgtttctctttgcagTATGCTCACATTCGTACAGACTAAAGTATAAGCTGACCCGGTTCAACCGTC
GAGCGGATATTATCGCCAAAGTGCAAACGACCTGCATGGGTGCTGTAACGCTTTCTACTGGAT
TGCACCGATACCTTCCATCTGTGCGCACTACTACAGGTCGACCAATTCCACCGAACCCGTGCGG
TTTGTGCAACATTTAGAGGTGAAGTTCTATTGGCTCGAGAATCGCACCTCAGTCGAGGACTACAT
AACCTTCGTGCTGATCATGCTACCCGTCGTGGTTATGTGTGGTTACGTATGCAATTTGAAGGTGA
TGACCATCTGCTGCAGCATTGGACACTGTACACTGTACACCAGGATGACTATAGAGATGGTAGA
GCAGTTGGAAAGCATGGCATCAGCGGAACGAACTGCCAGCGCCATACGCAACGTGGGGCAGAT
GCACAGTGGTTTACTGAAATGCATTAGGCTTTTGAACACGTCAATCCGATCGATGCTGATGCTGC
AGTGGTTGACCTGCGTGTTAAACTGGAGCATTTCTCTCATCTATCTAACGAACGTGgttagttttgtctt
gtttggaaatccaaaaacaaaaagatggctataattgaactttctattacagGGCATCTCGCTACAATCGGTTACCGTGGT
GGTAATGTTTTTTCTTGCCACTGCGGAAACTTTCCTGTATTGTTTACTTGGGACGCGGCTTGCGA
CACAACAGCAGCTGCTGGAGCACGCACTCTATGCTACACGGTGGTACAACTACCCAATAGCCTT
TCGCAGCAGCATTAGGATGATGTTGAGACAGTCGCAAAGGCATGCACACATAACGGTGGGGAAG
TTTTTTCGCGTTAATTTGGAAGAATTTAGCAGGATTGTCAACTTATCCTACTCTGCTTACGTCGT
ACTTAAGGATGTAATAAAGATGGATGTACAGTGAATGTTTTTTTTTTGGCTTGGCAACGAATGA
AGTTTTCCGAATCTATATTAGATCTAGAATTTAATCTAGATGTCATAATATGATCTTGGCCATGA
CCGGTTCCTGGTTTTGGAACCAATTCTCAAAACAATTTTGAACTTAGGGCGAGGCATGAAATGTC
CCAAGAACCTATCCAAGTTCTGGAACTACATATTACCGAATCTATCCCATTATTGCCTCGGAACT
GGTTTGGTGCTAAATATTTGTCCAAATGTTGGTCCTGGACCTATCCAGACAAAGATCTTCAATTA
TTCCTACCACTGGAACTGATTAATTGATGTAGGAAGTCATGGAGGTGTTCAGGGAGAATTTAAA
CACTAATGTTCCAACTCATTATTTCAAGGGCAATTCTATTTTTTATATGCCCCTACGGATTGATAC
GTATGTATTACTCCATTTCCTGGACTTTGTCTTATTCTTGCTGCTGATTGGACGTGAAATGTTGA
GAAAAAGATTCTTATTTATGAGTGATACAGAGCCTTTAAATACTCCTACGTTGTTTGCTATTTAA
GTATGGCCAGGCTAATCACAATCGCTACTAATGAACAGAATCTCTTCTAATTAAACCCTTTCGAT
TGATAGTGTCAATGTCAATGTCGAGATAATTGAACTGCAAACgATACCTACCTTAAACGGAGCAG
AACACATCAAGAAGCAATTAGGTGTGTCGTACGTTAGCAAGTAGTTCGCGAGGAGGAATAAAAT
AG

Figure 5

*ANOPHELES GAMBIAE*

Preferred DNA Codons

| Amino Acids | | | Preferred Codons | | | | | |
|---|---|---|---|---|---|---|---|---|
| Alanine | Ala | A | GCC | GCG | GCT | GCA | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGT | GGA | GGG | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCG | CCC | CCA | CCT | | |
| Glutamine | Gln | Q | CAG | CAA | | | | |
| Arginine | Arg | R | CGC | CGG | CGT | CGA | AGA | AGG |
| Serine | Ser | S | TCG | AGC | TCC | AGT | TCT | TCA |
| Threonine | Thr | T | ACG | ACC | ACT | ACA | | |
| Valine | Val | V | GTG | GTC | GTT | GTA | | |
| Tryptophan | Trp | W | TGG | | | | | |
| Tyrosine | Tyr | Y | TAC | TAT | | | | | http://www.kazusa.or.jp/codon/cgi-bin/showcodon.cgi?species=Anopheles+gambiae+[gbinv]

Figure 6

| Name | SEQ ID NO |
|---|---|
| Arrestin 1 (cDNA) | SEQ ID NO: 1 |
| Arrestin 1 (polypeptide) | SEQ ID NO: 2 |
| Odorant Receptor 1 (cDNA) | SEQ ID NO: 3 |
| Odorant Receptor 1 (polypeptide) | SEQ ID NO: 4 |
| Odorant Receptor 2 (cDNA) | SEQ ID NO: 5 |
| Odorant Receptor 2 (polypeptide) | SEQ ID NO: 6 |
| Odorant Receptor 3 (cDNA) | SEQ ID NO: 7 |
| Odorant Receptor 3 (polypeptide) | SEQ ID NO: 8 |
| Odorant Receptor 4 (cDNA) | SEQ ID NO: 13 |
| Odorant Receptor 4 (polypeptide) | SEQ ID NO: 14 |
| Odorant Receptor 5 (cDNA) | SEQ ID NO: 15 |
| Odorant Receptor 5 (polypeptide) | SEQ ID NO: 16 |
| Odorant Receptor 6 (cDNA) | SEQ ID NO: 17 |
| Odorant Receptor 6 (polypeptide) | SEQ ID NO: 18 |
| Odorant Receptor 7 (cDNA) | SEQ ID NO: 19 |
| Odorant Receptor 7 (polypeptide) | SEQ ID NO: 20 |

Figure 7

*Anopheles gambiae* odorant receptor 5 genomic sequence (SEQ ID NO: 21)

Predicted Exons: *ITALICIZED*, UNDERLINED AND HIGHLIGHTED.
Introns: lowercase.

tctagacttgaacccatgacgggcattttattgagtcgttcgagttgacgactgtaccacgggaccacccgtttatcactatcactatt
aattaattataatatgcttttgtagcgatcagcctaccgggttttgtttctctggatatcttaagttcccatttgattatcaagatagaa
caacaacttgtaccttaaataatcattacgtacccttaatcaacctgtgcatcaaggagttttcgcgaaagcaaaaatccgattgtct
gatgttgtcttgattccatccgattcgttactggttctgcaaaatcgtccaataatacggcaatgtccttatcgatgcttgaatcaacat
cacattgtttgcatttcgttttttgcgtgcaaatatgttatttgcaaagaaggcaaggtaatgtgcttaagagtaaatacaattcgctg
tccattttttgtccaccagtgtgccagaacccgtgccttttagtccttcgaatacatccgaccagtcagcaagcaagtgcatc*ATGG*
*TGCTACCGAAGCTGTCCGAACCGTACGCCGTGATGCCGCTTCTACTACGCCTGCAGCG*
*TTTCGTTGGGCTGTGGGGTGAACGACGGCTATCGCTACAAGTTCGGGTTGGCATTTTTA*
*AGCTTCTGTCTGCTAGTAGTTATTCCGAAGGTTGCCTTCGGCTATCCAGATTTAGAGAC*
*AATGGTTCGCGGAACAGCTGAGCTGATTTTCGAATGGAACGTAGTGTTTGGGATGTTG*
*GTGTTTTCTCTCAAGCTAGACGACTATGATGATCTGGTGTACCGGTACAAGGACATATC*
*AAAGATTG*gtgcgtgataatgattgataaaaggaacctttgagcaactcctatccctttcaag*CTTTCCGTAAGGAC*
*GTTCCCTCGCAGATGGGCGACTATCTGGTACGCATCAATCATCGTATCGATCGGTTTTC*
*GAAGATCTACTGCTGCAGCCATGTGTGTTTGGCCATCTTCTACTGGGTGGCTCCTTCGT*
*CCAGCACCTACCTAGCGTACCTGGGGGCACGAAACAGATCCGTCCCGGTCGAACATGT*
*GCTACACCTGGAGGAGGAGCTGTACTGGTTTCACACCCGCGTCTCGCTGGTAGATTAC*
*TCCATATTCACCGCCATCATGCTGCCTACAATCTTTATGCTAGCGTACTTCGGTGGACT*
*AAAGCTGCTAACCATCTTCAGCAACGTGAAGTACTGTTCGGCAATGCTCAGGCTTGTG*
*GCGATGAGAATCCAGTTCATGGACCGGCTGGACGAGCGCGAAGCGGAAAAGGAACTGA*
*TCGAAATCATCGTCATGCATCAGAAGGCGCTAAA*gtaaggtctgccggtatgttgtggatagaatacattt
ctagctgctttcag*ATGTGTGGAGCTGTTGGAAATCATCTTTCGGTGGGTTTTTCTGGGACAG*
*TTCATACAGTGCGTAATGATCTGGTGCAGCTTGGTTCTGTACGTCGCCGTTACG*gtaacta
aaagcactgtagtgatctgtctgccacaccattcactgctgtgtcttgttttgtcactcttcccag*GGTGTCAGCACAAAAG*
*CGGCAAACGTGGGTGTACTGTTTATACTGCTAACAGTGGAAACCTACGGATTCTGCTA*
*CTTTGGCAGTGATCTTACCTCGGAGGCAAGTTGTTATTCGGTGA*gtttcagttacttttccgttcccc
tctaaccgtaccacttgtaccatttgtttgagacagagcttgagcgtag*CACGTGCTGCCGTACGGTAGCCTCTGG*
*TATCGCCGTTCGGTTTCGATTCAACGGAAGCTTCGAATGGTACTGCAGCCGTGCCCAGA*
*AACCGGTCGGCATCTCGGCTGGAAGTTTTGCTTCGTCGACATTGAGCAGTTTGGCAA*
*T*gtatggggagaccttccactgtggcaagaaagattttctttattaatgcatcttttaatttacag*ATGGCAAAAACATCA*
*TACTCGTTCTACATCGTTCTGAAGGATCAATTTTAA*aggggaactcccccacccgaccagacgacggaa
agctaacgatgtgcaattgaatagtcattagtagcgttttgctcgcaaacgaactaaccctttgacttttttaagttcactacggtgag
gacaaaaatcaataaattaaatcgagaccgttgatgagcaaaagaaaaaaaaatattttactgattttcatttcgttccatcgacta
cataatcataattatatgccacattttattataagtttttg

Figure 8

*Anopheles gambiae* odorant receptor 6 partial genomic sequence (SEQ ID NO: 22)

These are the predicted last three exons of another candidate *Anopheles gambiae* odorant receptor.

Predicted Exons: *ITALICIZED*, UNDERLINED AND HIGHLIGHTED.
Introns: lowercase.

aacacccatcttatcggcaaaattagtatttaccgtttgaaagcggcttcccttcctggctgtttctcactctctctctctctgtctctctta
ttgatgccgtatgcgccgcgtgctataggctag*TTATGCTTACCGGATGTTGCGATCGCGCACGTGCTTT*
*TCCGCATACGCCAGTGCACACTTGATGGCGGTGGTGATGACGTGCTGCTGCGCACCGTT*
*TTGTGCTCGTGAGTCAGACCTTTTCATTTCCTGCAATATCCTGTTTCTTTCCCGACCCC*
*ACAGACGGTTAGACGGATATATGCTGGTAAAGTTTGTCCTCTTCATGCTGTGCTTTCTG*
*ATCGAGGTGCTGATGCTGTTGTGCCGTACGGTCACGATATTGTTGGAATCC*gtaaggcaccaggc
ggtgatgagcgagtcgcgagtaattgaagcttttgcttttaaaacacatcagag<u>CCTTGCGGTGATTGATGCCGCT</u>
<u>TACGGTTGCGAATGGTACCGGGAAGGGTCGGTGGCGTTCCATCGATCCGTGCTGCAAA</u>
<u>TTATACAGCGCAGCCAGCAGTCCGTCATACTGACCGCATGGAAAATTTGGCCCATCCAA</u>
<u>ATGAGTACTTTCAGTCAG</u>gtgagttgccaattgattgccgtttgcgttaatatttcagtaagagtgcgctctttcccttag
==ATCCTGCAAGCTTCCTGGTCCTACTTTACCGTCCTGAAGACCGTCTACGGGAATAA==gtaa
gcgcgagagagagagagagagagcagtatcgttcaccctttggatgaatcaatagatttctaatcatgaaccattgaaaaatgaatca
acattttcgctagttgcacaatattgtaccattctatacagcttcaccacgaccaagcgtttgttgcatcaggaccaaacacgtttcga
caagccgcgtcacctgctggc

Figure 9

*Anopheles gambiae* odorant receptor 7 genomic sequence (SEQ ID NO: 23)

Features
1. Predicted Exons (7): ALL CAPS, ITALICIZED, UNDERLINED, HIGHLIGHTED
2. Introns (6): lowercase
3. 5' and 3' sequences: lowercase, dotted underlined ccgcccgggcaggtgacttacgcggtctgacttgctggtgcgctgctttgtacggcaaacggctacacaagcgaatcgaattattttcc
tatcacgctgcgcttaccagcgcctgctggtaggcaaagaatgtgcaaagtttcatttggcttggttcgtctgctttgctgtgaacgtgt
gcacggttgcatcgctaaggtttcggtgtgagccgagaagttgcagatcgaaatctctttgtgtgtgtgtgtgtgtgcagtgggaa
gcattgtgtttagtgagaagtgaaaagaaaagtgctgaaaaatgcaagtccagccgaccaagtacgtcggccttcgttgccgacct
gatgccgaacattcgggttgatgcaggccagcggtcaactttctgttccggctacgtcaccggcccgatactgatccgcaaggtgtac
tcctggtggacgctcgcccATGGTGCTGATCCAGTTCTTCGCCATCCTCGGCAACCTGGCGACGA
AGGCGGACGACGTGAACGAGCTGACCGCCAACACGATCACGACCCTGTTCTTCACGGCA
CTCGGTCACCAAGTTCATCTACTTTGCGGTGAAGTCGGAGAACTTCTACCGGACGCTG
GCCATCTGGAACGAGACGAACACGCACCCGGCTGTTTGCCGAATCGGACGCCCGGTACC
ATTCGATTGCGGCTCGCCAAGATGCGGAAGCTGCTGGTGCTGGTGATGGCCACCACCGT
CCTGTCGGTTTGTCGgtatgtgtgtatgtgtgtggccgtttgggaaagtgtctttgcggcagaacccccaatctactgttacgc
ttgactgggttttttgttttttttctcggtggagggacgggataaaatatctgaaagaataattgagtcaacccacaggggatgcaag
acatcgcaggcagagagtttgggtttgatttataccgcacaccgaatatcttcacggttcataagcttcaccgcggtgaaaaggga
actccccatttccctgtttctttttttttcttcctctcgataaaattactcatcgcttttcgttttttttttttttgttgttgcttctttcttctttcatc
cctactagCCTGGGTTACGATAACATTTTTCGGCCGAGAGCCGTCAAGACTGTGCTCGATAAG
GCAACCAACGAGACGTACACGGTGGATATACCCCGGCTGCCCATCAAGTCGTGGTATC
CGTCGAATGCAATGAGCGGACCGGCGTACATTTTCTCTTTCATCTACCAGGTACCGTTG
GCGGAATgtcctgcgcgtcacagttggcagtcagtgagcggcaacacggcgaaaaaatgggactaaaaccggtcttcacaga
gccaacacattcctacagcaattgcataccttcgggcggtcgggactgggcaatgcagctacaacatcctcgcctaaagttatgcaat
tcgagcgacaaatgttgccgtgttaggcttttttgtgataatagtcgttttttttgtcctctcgcttatcaaactctatcaacggaggaaa
tccattttcgctacaatgcctacagctcaagtttcaaggtcaatcgagcgggtggggatcaactttttttattcattttgctaacgcccca
tcaacaaattctatgttctcaatggcaaagattactgcccgcaccaatcgcccaacgaaacggcaaaagaaaagcgacgattatga
agatgtccaaaccattgcccgcccgacgctttatctgatgatttgcgggatggcttttacttgtctgctactttcaggcacaaaaggaa
atgaaaccagcgcaggctcgtttgccggcttgcggaggttcttcaggcactgaggctgagtacttaaatcgaacgattttttacgattc
tggatccagttttatgatgtggcctgcattacagtggcaattatacccctgatgttcatttcattgcattttgtaagtttgtgctggtaacg
cccgtaacgattaattcttttcaaagagattctttcaaagagattcaaaatgtgtataacaaatgctaacgaatggaccgtacttgg
agggttgcggaaagtaacgttttaaaatattcatcacaatcctctgcaaacttgtgcttaattaattggtgcacaataagtttaaact
gtggcggcagatgtgtcgctgtccgcttccttccttcccagcaagctcgtgcgaaataatttattccatcattttaatacagccgtttgtg
cattttaattagcaaagcaatataaaaagcagctaaccatccccattaaaacaaagtgcttccgggcccaattgttatggcggtgga
aagtaatggttttaccagtggaagtgtcctttcccatcgtgggtacttcgcgatattcttgtcttatacaagtgcatacagaaaaaaa
ggacaaatcctccttgctatggtctaaggccagcttcggtaccgcttccgcttcgggatgtcataaagtttgatgggtgttttaacatt
acttccgctcttaaccacctaatggacttttcatgcttgagctaaagttaaaccagccaccagcggtacgcaccgagccacggttgatt tcggcggcggcctcatccccagttttgcgccaccaatattgccttcattaatctgtaccctcggagcgttagggcccgcggacgagtcct
cgttgtaatgcaccgccatgccacgggacgggataatccgttgggacggcgcgaaagcgactatcgcggacggattggttcgaccg
tgctacaacacattttatgcttcacagatttacttcctgctgttttcgatggtccagagcaacctcgcggatgtcatgttctgctcctggt
tgctgctagcctgcgagcagctgcaacacttgaaggtaggtacggtagcaaacgtggttgtctttacatccgcgtgcagcattatcct
tatcgacgtgtagtgttaacggtaaaagaggaagcgataaaaaagcaacattctctcacaccctcgatctctctttatttctctctct
ctctctctctctctctctctctctctctctctctccatctcctcgggcag*GGTATTATGCGATCGTTGATG*
*GAGCTTTCGGCCTCGCTGGACACCTACCGGCCCAACTCTTCGCAACTGTTCCGAGCAA*
*TTTCAGCCGGTTCCAAATCGGAGCTGATCATCAACGAAG*gtatgtgaaacgtgtgctcgtggcagacg
gactcaaagagagcataacacaatccctggtagttcatttcaatgaccttaacactcggcaagctaagcgagacagtggggacag
tgagaaagagagaacaagaaaaaaaaccatcatccgtacgacatcatcgctacgtaccggtatttcaggatgaggaaataaaac
gctaggggaatgaaagtgcgacagaatgataaaacaatcccccacccaggcccccagcctggacgaacggatgtagtgtgcgaagc
gagcaaaaaaagtcaaataaattgaagtttaaaaatagattttccccgtccatccgtggtggagcgtaaagcccggcggacaactt
cgagcacggcgaccgtgcacagtactgtgccacagttgtagggacggataagctccgttcctttttatccttttttttggagatttgt
ttgcgttcgcatcgttagacgagcttagtgccgtgttgctctaattgctatttattataaagcgcttccaaatagaagatcggttctctc
catttaatctatcgcgcctgtacgcctgaaactatgcactgtgctgtgaaaccgtcaagctcgagcacgacgaatggcccaccgtacc
acgcccgtggtgcccaaagcgcaacgcgaattgcatgttaacaaacctttgcctaccatccaatccgtgtgaaattgcccgctctcttt
ctctcttttgcgctttcggtgtatcgaacggttttgtcccttttttttactttgctcttgatctcttgctgtgctcactttcatctcatgttttgc
ctgacgtggtgggttttcgaaaaaagagcgatttcttctgcgtgtgtgtggttttttttaaataaccgctccaggtcgtgttgaacg
ctgcaggaccgatcggagctagtttattatcagctttagtgtttatcccacccatgccccacatcacgtctgtggagagtgggggaag
cttaagtccaatgtaatttaccgtgtttctgtcgttcgtcaccttcttcgtcgatggagattggtgcggttggcacgataaaagcccact
gcacgttacggaccgagggaaaggtcttttttgtaggcctagcaacggtcctcattcaccgcatgggggtgtagctcagatggtagag
cgctcgcttagcatgtgagaggtaccgggatcgataccccggcatctccaacccacacaaaacgttttttaagaagatttttagggaa
gatattaacgcgggtacactgtgctcctctaagttggaagagtagatgagatgatgacaagggagaaggaacatgtgtacgtgttt
gatagcaaacacacaaacaacaatatcatctctgataataatctgatgtgtgatgtgtgtgtattgttgttatgctgcctttgccatct
tgtccctctctctcctgttcaactcctaaaagaattgtttggagtcctctcagttcctcgtaaagatccttcgagattcttctttccttttt
attatttattccacgagcctctgacataagtagccttccgcttatttccttcccttgcacttgtcagttccgtgtagagcgtcatttgag
gtttacacatttcccaccgacgcctgattgttacattgtcatctacattgctttccgtttaccgttccgccctttttttttttaacgctaccaca
g*AAAAGGATCCGGACGTTAAGGACTTTGATCTGAGCGGCATGTAGAGCTCGAAGGGGG*
*ACTGGGGCCGCCCAGTTCCGTGCGGCCGTCGACGGCTGCAAACGTTCGACGAGAATGCCAG*
*GAACGGAAATCCGAACGGGCTTACCGGAAGCAGGAAATGATCGGTGCCGCAGCGCCATC*
*AAGTACTGGGTCGAGCGGCACAAGCACGTTGTACG*gtaggtatggtaatttctaaggtgtggtgtaaag
cctccaggttccatgaaaaagggatactttaccacagtaagagtttgttttgctggacttacattctttggagcattgtttggtgttgtg
ctgaaaccggttgcaatatcgttttgcgaagaaattatgtgtaaagcgtattacaatctcattcctctgttaatctgtaccaattgtgtc
agccccgaccgaaagcaggcctaattcgtaccagaaaaaccacaagctgtttgtaagcatcgatacgcccgaagctttcaatccagc
caaggcgccacctactattgacgtgacttttttgcacgttcacactctccctctcccattcttttctataaccaatcgtcgctcagccagcat
cgcccggagtgaagtttttatttgaacgatatcacccgtatcgattttccactaaacatgcttaaatcgtttcacaaagctccccaaa
atcccatttcaccaatccaccaatttgaagtccgtcgtcctttgtgtccttgtgtttgtgtttttgtgtgagctggagacatggggagt
gagtaaccgaacaacctcttgccgctgcttcacgatatcgaacagcaccaagataagcatcccttttccctagccgatgtctccgata
tctcgattccgcttccagcgaggcaaagaaaaaggcgaactggctgacctcacccggggcgaggaaaaagcgtagggattacgtc
gagcagcacgagttgtgatttcttcttcttctggttccataaatcgctgacggtttccattaccgcctgcggagtgcacacacgtgaag
ggaaagcgaaaacgtttagattccagcagcaacggcagcaccagaagcagcagcagcgcggcaaattgaatcatcctgacgcgat
gagttgtctgggttttcgggtcggtggcttacagcaccacaccatctgctgcagctaatacagctgtaaatttcgttagacatagactt
gattttacaatattacacacacacttacacacacagctatagatttgtcgcttggcgtatggctctgtacgcgcgtgccgtacatgccgc
gagccgtgttgctgctggttgcgatacggatcacgtccgattcgattcagcctgcgtgttttggtgaagatccttatcggtgacccact
ttcagtgtgtcgagagcgagggtcactatggcgcctgtcagttggaaagctaggctcgattcaaagggccattgtgccagtgttcttt ttaagatagcgataagcttttgatcgaaatagtaaatcaaacattgtttcttttttcctattccaaactgttgccaacctcattattacg
tttttgcagcgggtgtatagtaaattgcatactttaaggcgtgatttttcaaatgtagcgttccgtatgcagaaacgccatggattatgc
aatttaaacaatgctgcttccttaacattcaaataacggcttattaaggaacttttttgtgcaatttgtttttaacagcaaatagttagc
tcagaacgatcacatttagtatcgcttcaacaaagaactcttttaaacacacaatttgtaatgccattccctcgagaaagtttcttgtc
agtcctcctctgcatcacagcaacaaccaaacctgctcatgtttcctgctcgtttcctagctgttttgaacgttatttccgattcctgtgct
tgcccgcttttcttacaatcaaccacaatggttcagatttcgctcttattttattgacccactgctttcgtgctgaagcccgtggaaacaa
tgcgccaagctcagcatccagccatgcatgtaaaatgagccacgcgacagattttagacatcgctttcgctctgcaccggaggtggtt
ttattcttgtttccgattcccacgtccattcgtcctgggtccgtccgccgggcccgaaaccgtaagccgtgcggggaattacgcaatcga
aacgagccagaaaatgagcacgccaaatgcaaagaaaatccccttttgagtggtgctcctgccaccactcatctccccaactggtgg
gtgaaaaaccttgtgcgcccttctctttccagaaaaaaaacgcctcgctcgcacaaaaacatgctcgcccggtgaagctgcgtatgt
cgcagaagctcaaaccaacgccgccagcaagcatcaacaatttctattcaaacacccaacgcagcgcccaaaccgggtgcactgta
ctcagtagcgaagatgctcagattgtcccgtgcgctgctttcgatgcccgtttcggagcggggaagccatcgcttgccaacgttggcgat
gtcttttagccgtggatttgaatttctgaatatcacaggcgggcgcggtttgcctgcaaggttgttgcttccacacgagcattgcttt
ccgtaccgcggtggggcgagttttcaacgcaaccttctacaagcaacgccacaacgcctgggagcgatatttaacagaaacaagaa
catcccgaacttcagcacatgccgtgatttgcctgttgaaaagcttttgtgagcgtgtgagttgaacgagctctatttccccagcgat
gggtggcatttgtgtggcatgctatcgtcagcttttcttgaatctttacctctccattcgcctccattagtacacgcgtatggaaaatgg
gtgcaacggatcagaacggattttccgcgacagacttaataaagggaaagcaacgcgttttttgcatgtgtagtgtttatgagcttt
atgccgttactttgcaattaaaaatagcaaaaaataacagtttttttttgtaagcggattacaaagaatgtatcagaatattacgtg
aaacattcatttcatgctgttaacgctcaaatagaatagttttgtaacacggattgcataccttgccggtatcggttacatttcgccta
acagtatgcaatctgtttagctttgttgtttaatgactgcgttggtagtacaatatttatttacaccgcgtaatttatctcacaaattgc
aaaaaaatgtcaatctgtatcgattattcacacaaatcagatcccggaaccagtgtagcccaatgtgctcttattgaattaccacga
acaaatcaacctgatgcccgggtccgttggcaaacagcttgcgccgaagccgctcagtgtttcgtgcactaccgtgctgccattttgct
gccctcatcgaacagataaacagaagggcaactcttgtgagcatcgcaatgcccgtctgaagttccgtcgaaaatgggcctaaattc
aatttgacgcatttacccgcgaacaattgcgcgaaggctgtcaagtgtgttccacgaactgcgacaacaagcacacacacaaacac
aaatgttatcgtttcggcatgtttctcggtacaaagcgtgtggcgctatgtggcatgccgattcccagacagagtgatcgatagtaaa
tgtagcctatccggtagcattcaatttcctttctatcctcgcaaacaaagcccattctggggaggcgtggtgaagctttcaaaggcat
tgtgaaacaaatgtcctggttcggagggatgctggggaaagcaaacacggtgccgccatcgctgctaccgtcaatcgatcatgcatg
atgtgattaatatttgtgttattcacctgcgtatctatgcgtccgtcgtgtcgttcggatttccggaagtcaaggaaaaagcgactcca
tttgggattggttttgcagcgaaaaatcaaaacattcgcacaaaaccgtcctccatttcaaatgcctacacttgtcactgtatatctct
ctttctctcgttttgccacgttgcag*TCTCGTTTTCAGCAATCGGAGATACGTACGGTGCCTGCCCGTGCT*
*GGTACACATGCTCAAGGTCCACCATGAAGCTGACGGTGCTCGCCTACGAGGCAACGAAA*
*ATCGACGGTGTCAACGTGTACGGATTGACCCGTAATCGGATATTTGTGCTAGGCGTTGG*
*GTCAGGTTTTCCTGTTTTGCATCTTTGGCAATCGGCTCATCGAGGAG*gtacgtgcgctcggcgtg
ttgccgtgggaaagcattctccctgccccatatcgcttcattctcccagatcacacatttgcatcacaaagccagcacacttttgcttcg
ccgctgccatctcggcttctgaatgttttcacttctcccatacttctcccgtgcag*AGGTCATCCGTGATGAAGGCGGG*
*CTATTCCTGCCACTGGTACGACGGGTCCGAGGAGGCAAAAACCTTCGTCCAGATCGTT*
*TGTCAGCAGTGCCAGAAGGCGATGACTATTTCCGGAGCCAAGTTTTTGACCGTTTCGC*
*TCGATCTGTTTGCTTCG*gtaagtgtagcctggtggctggcacagaacaggctggcaaaacagggactttggctctagc
ctgatggtggtatatgtgtgtctattttttgctaccattctcgcatcccttcctttccag*GTTCTTGGAGCCGTTGTCAC*
*GTACTTCATGGTGCTGGTGCAGCTGAAGTAA*acagccgtggccccggaaggatgtgttttttttcgctcgttcg
gttgtttgtttgtgcacactttctcttggacatttctctactgcaaaggtttaacaaacagcaacaacaaataatcccaagtttctttt
acagatctttgcaaaatgattagatttaatagattaacagtgcttgattatctgtcctgtagcaaccggggctgaagaacgttgatt
tggtaaaagtacaaaagggacgttggaaattgaaccaccagaagagtgatatttatgcaaagctcaccaagggaaatctatgtat
gtgtgatttgcgctcatcaagcactgtatgtgcctttcaactagtgcagcaataaagagtacaaatgtttcttagcgcaccgtacattg
tcgtttcggcgttttaaccgttgttgataatacacaaaagatgataaaaataaataataacaaaatgttaatatgagtaagtacta

```
aatagagaaatcgttttagtatgatcatacctccaatcatttgtttgaaattaactttaattttaactcaaattaaaccgatgttttact
ttctgtgagaattattgtggaagaacttaatggaagtataattaaattgattgctaactttatgcgtttttcaatttacgaacgctagt
cttcaaacatcgcttcaaaagtattactaccacattattcatttacttatagttatatttattgcctcttcatctttccatggccagaact
actgcagaaaagcttcttttttgctcgctttccgatggttggttggacgaagttggtaacaaacggcaagcaattagcataaactatt
ttcgcatcgagatggaaatgaatgtaccactagaaccgagtgaaatgaattactttcaacttgcacgccaaaaccattatctaaag
tacgcacaacttaaaaacaaaccccaaattgtcgtccaccttcattccactttcttgctacactttccgaccgagttctgtagcgccag
cagcaaaaaaatacatataaaaccttcatcactcaagctgtatcgagccagcgtgggttgtgtttgactgtgctgtgaaagaaaga
agaaaaaaaaaacacttccacgggaagctagcaattggaaatgcataaattaaccggaagaaattcgcaaaacccgcaccgac
gtaccgcaccgcatccgtaccgataccggaacaaacggtgtgcgcgaaagaatccgctagcagccccactggcacgggtatttgctt
ttggttctgtgtttttcttccactggtttgggtgcctgggcgaaggctagctcggctactttccggggccgcaattttctgcagcccaag
gcggcgtgctcgtggggccaaaagaat
```

*Anopheles gambiae* arrestin 2 genomic sequence (SEQ ID NO: 24)

Features
1. Predicted Exons are highlighted and underlined.

GGTAAAGGGCTGGATGAGGAGAGGAGACTTATATTTTTGGAAGCCTTTGGTAG
GTGACAAGGGGGAGTTAGTGATAGGGGAGTGGGGCCAAAATAGGGAGGAGGT
AAAATTTATGGTACGCCCCATAGGGGAAGAGGAAAGTGACCAGAGCAGGCAG
TGTCCCCGCTGGGGGGCTCAACGGTGAGCCGGCTGTCCTCGGCGGGGGAAT
GAAACCCTTACAAAATAAAAACTAGCGTTTTTCTACTCTCTCAAATGTCCAAAG
CTGTTGCTCAACTGGGTGCTGAAAACCCCTGCGTTATGCAAAGCATTAGTCAGC
TGAAGGTGCAAAATCTTCCACAGCTTGCATAAAGGAGCTGCTGATCCGTAGCTT
GTCCGTGCAAGATCATACGATCTTTATAATTCGCAAATTCGCCTTCCCTTCTTA
ATCCTTTATGACGCCCGTGTTGGTTCGCTCTTTCCTGCGACACACGGTGCTCAG
CCAAACGTGACCTAAACACGCACCCCACAGCGTACGCGTGACGTCACGACCTT
TTGCGTTTTCGCGGGGAAATAAGATTAACGTTCGCTGCCGACGCCCGTTGACC
GTTGCATCGTAATTTCGTATACCGTTCTGCGCGTGTACCCCTGCGTACGTCCAG
GCTGTTGCGTATCGCACCATCGTACGCGAACGGAAGGCATCGGGGAAAGGGAC
GCAAGGATGGGCATGAATTAGCTGACACTATTTGTCCCCTCCCCCGTAATGCA
GGCGCAACCACCTGGCAGCTCGTCGGTGGCAGTAGCTCGAGCCTAATTCAGTT
AATGGCAATCGGGCAAGCGTCGATCGATTTTCCCGCTGCAAAAGCCCGCACGS
KKWYSGTCCGGGAAACCTTTTCGGTGTTTTCAGTGTACGGTCCACCACACGGG
CGGTAAAAAGGTATAAAACTGTCCACCAGCCGACCGTTCGATCGCACTTCTGG
TTGTTCTTTCAAACCATACAATACCCGAAACTAGCTGAGAACTTTGTAGTTCAA
GCAATTGAAAAAACGCAAGAAAACAGCGCTCCGTAGAACGACCCCGGAGAATA
GACACGCAATTTTGTACGACCAATCTCGAAGCGAGTGAATTGAGGGAGTGAGC
TACCGTGTGTGAGAATACTCGTGATACATTTCGAAAGTTCTATCTGATTGTTTG
CTCTGTGTTTGCGAAGACACAAACTAACGCGCAGTGATGGTTGTCGCAGTGAA
AGTGTTTAAAAAAATCCGCCCCGAATGGCAAACTGACCGTCTATCTCGGCAAGC
GTGACTTCATCGACCAGACCGACTACTGTGACCCGATCGATGGCGTTATCGTG
CTGGACGAGGAGTACCTGCGAGGCCGCAAGGTCTTCGGCCAGGTTGGTTTACT
GGAAGATCTCGATCCTCGATGACTGCAGTTCAGGAAGTCTTTAAGAACTTGTTA
AGTGAMCAGATATGATTCTTTCGAGTGTCTACTTACTAGATGAGTGAATATGTG
TGCAATTTGGAATGAACTCTCAAATGCCTGGAGCAGAAGCAGAGTATCGATAA
CTTGGAATTACAATCAAGCCTCGTTAATTAGCCAATACTCATGTTGCCATGTTC
TGAATTTATCAGATCTTTGAAAGGTTCGAGGATATTATGAAGATAATAGTGCAG
ACGGCCAATACAAAGGACCTATTATCGTTCTATTGCTGAACCACAATGTTACAG
CGTTTGATGAATATCATCCGATTAGTTTCAATACAATCCAATTAGTGAGGTGAC

ATACTAGAAGGACACACAACTGATGTCATAATGTAGTTGAAATGAATGCTAATA
TCAAGGGTATTAAAGGTTTTTAATGAACTCCAACTCATTGGATAACTCTTTCGA
AGAACTTTGATGTCTCAGAATAGCCGAATTCTTATCTTTTACTAACATAGTTGC
AAGTTCTCAGCATGTAACTGTTCTCCAACCCACTTCAATGTTCCATTTCTCTC
TCTCTCTCTCTCTCCCCGCAGCTCATCACCACCTACCGCTATGGCCGGGAAG
AGGATGAGGTGATGGGCGTGAAGTTCTCCAAGGAGATGGTGCTGACCAAGGAA
CAGATCTACCCGATGGAGAACGCCAACATGGAGATGACGCCCATGCAGGAGCG
GCTGGTGAAGAAGCTGGGCGCGAACGCGTTCCCGTTCACCTTCCACTTCCCGA
GCATGGCGCCGAGCTCGGTGACGCTGCAGGCCGGTGAGGACGACACGGGCAA
ACCGCTCGGCGTCGAGTACGCGATCAAGGCGCACGTCGGCGAGGACGAGAGC
GACAAGGGCCACAAGCGCAGCGCCGTCACGCTGACGATCAAGAAGCTCCAGTA
CGCGCCGGTGTCCCGCGGTCGTCGTCTTCCTTCGTCGCTCGTCAGCAAGGGCT
TCACCTTCTCGCAGGGCAAGATCAACCTGGAGGTAACGCTCGATCGGGAGATC
TACTACCACGGCGAGAAGATTGCGGCCAACATCGTCGTGACGAACAACTCGCG
CAAGACTGTCAAGAGCATCAAGTGCTTCGTTGTGCAGCACTGTGAGGTTAGTA
GTGATGGAGCATTCCTGGGAGGGGCACCTAGATGTGATGATCGGGTTAATTT
AACTCCCTAATCATTCCCTCCTGCATTYTAGGTCAGCGATGGTGAATGCACAGT
TCAGCAAGCACATCGCCTCGCTGGAGACSCSCGAGGGTTGCCCGATCACGCCC
GGGGCGAGCTTCACGAAATCGTTCTTCCTGGTCCCGCTCGCCTCCAGCAACAA
GGACCGCCGGGGCATTGCGCTCGACGGCCACCTGAAGGAGGATGACGTCAAC
CTGGCCTCGTCCACGCTGATCAGCGAGGGCAAGTGTCCGTCGGATGCGATGGG
TATTGTCATCTCGTACTCGCTGCGCGTCAAGCTCAATTGTGGCACGCTCGGTGG
CGAACTCCAGACGGACGTACCGTTCAAGCTGATGAACCCAGCACCTGGTAAGT
GTCGTAAGGGAGCGAACTTCGTACATCATCGAATATCTGGTGCTAATGCATATT
TTTTTCCTATTTCTCTATTATCAGGATCTGTCGAGCGAGAGCGCGTGAACGCCC
TGAAGAAGATGAAGTCGATAGAGCGTCACCGTTACGAGAACTCGCACTACGCC
GACGATGACGACAACATCGTGTTCGAAGACTTTGCCCGCCTGCGGATGAACGA
GCCGGAGTAAGCCTGTCCCGCCTGATGCGGCATTCACYKRCAACCATCCTTCA
CCCCAAGGGCGAACGGCTTTAATCCGGAGAGGGGACAGCAAATGCCATGTCTT
CTGTTCCATTTCCTCCACCGAGCACCCGAGCAGGCAGCAAACGCAAACATGAA
GAAAACACACACGCCCCAAAAATCCTCCCAATGCTTTTCCGCGCCAAGTATGCT
TTCTTTCATGCCCTTTTAATGCTCCCAGGAGCGGTACGAGCGTGCGTGTGATGG
CTGGGCGGGGACGAACGAGTGTCCCTCGGGGGGACCCTTCGTCTAGGCTAGC
GGCTAGAGTGGTGGTCACCTGAGAGACGCTCATCAGCCTTTCCCAGCCGTAAC
CACACGTAACMATGTCCAATGTGATAACACTGATGATGCTATTTAAATTATTAA
ACGCAAAAAACACGGCGCCGCTAAGCAACGAACACTAGAGCGCGCGATAAGGA
AACAGCAAGAAGAAGAAGAAGAAGAAGTAGTAGAGAAAAAACCTATCTAGTGA
AGGAACAACCTACCCTATAAGTGCTCCCCAAAAACTATAACGATATATGAAGT
AACGAGAGAAAAACGACATGAAAATGAGGAGTGTTAATGGTAGCCTCCGCCAA
AAAACAAACAAACGACTAACGAAGCCAAAACCCCCTTCCTAAAATCACAACAAG
CAAACTAACGATTATGAAATGGTCAACACCAAATAGACAACAAATTTGATTCAT

```
CGATTAATTCCCTGCCGGAGAAACTGTGCCGAGAAGTTCCCGAGAAGAAAACC
AGAACATCAACGACTGCGCAGTCAAGAGGTGGGGCAACGCGAACCAGCAACTC
CCTTGGGAATGCAGAATCCCCAACTGGGGGTGCGATGGTTACAATCCTCCTCA
ATCGAAGAACACGCACATGAGTAACGTGCAGCAATTAATCGATCAATCGAAGA
GCAACTTACATCGAAAAATGTTTAAAAACGAACAAAAAAAAATATCATAACCAT
ACACAAGAACCAAGCCCCAAAAMCCCAAGCAAACACCAGAAGTGAACGAAATC
GACGATAATCTAGTGCAGCTCCGGKTCGTACGTGGACGCTTTTCCCCGGKTTG
GCTATGGTGRAAACCGGCCMCATCCGAACCGCTGGCGACAGCAGCCTTAGAGT
GTAAGACGTTTTATGTTTCTGTTTTGTTTTTCGTGGTGAGACAGCAATTGGAGC
AGGCAATTTAAGGGAAACGAGCAAACGATTTAGGCAAATGGAAGCTAGAAGCA
ACAAAGACGCGCGCAGAGGAAGAAAAAAACAGACAAGAAGATAAAAACAAAAC
CACACGAGCAATGAATGCAACGAATGCGGTTGGGAAGTGAAGAGCTAAGGAAA
ACGGTGCGGAGAAATGGACATGAAGATGTCCTTTTCCCGGTACCGTTTTCACTT
CCGATTCATTCACCCCAACTCGTTCAGCGCTCCTTACTGCGAGTCAATTATTGT
TTCAGATTGTGTTCGATTGGTTGATATAAGCTTGTTCATGCAAAATGGGGGTTT
TTCTTATCTAAGGAAACCATGCTATATTATTACCTGCAAATGCAATAGGAACAG
AGCAGAAAGGAAACTTTATAATCMACTAAAATYWAACCMAATTAATTGGAAAA
GAGAAAAAAAACCCACAACTTCAAACCAATGCAACGACCTATTGATACATTTGA
AACAAACCCAAAGGTCACGCAACACATAGAGTCAGTTTTGAGTTTTGCGATGTA
CAGTGGACTGTTAGTAGCTGTGTTTATTTTGTATAAATCTAATTTGGCTATGTT
ATTATTGTAATTGGAGAAAAAATGCTGAGCAACCAAAAAAAAACTAACTTACAA
ACAAACCAGCAACTATTGAATTTGTTTTTATTTGTTCCAATTTGTACTGTTTTTT
CAGGTTTCTTTTTTTGCGTTTGGTCGGGAGGCTTTCGGCCAACGGTCCACAGGT
AGTAGAGGGGGAAAGAAATAACTGGTTGATGGAAGAAAAAAAAAAGCAACCC
TTACCCTAACTCTTTGTAAAGATATGTATACGAATGCACCGGTATTTGCTCAAT
TAGAATGTATTCCCTTTTTGCTGGAAGATAGGGGAAGGATTGGGATGGACCGT
TTTCTGTTTCTAGAGAACAATTTACTGCAACGAGTGTGATATTCAAGGATGTGA
TAATGCATTTTCCAGCAGAGAGTTGGAGTTGGCACTATTGTGATTGTAATTTGA
AACTTTGAAACTATTACAAATACCAAACTTTCCTTATAAAGGGGGAAATTCTGA
AAAGAAAAATCATATTTCACCCCAGTTGGGCTAAAACCATTTG
```

*Anopheles gambiae* arrestin 2 (Ag2) amino acid sequence (SEQ ID NO: 25) aligned
with *Drosophila melanogaster* arrestin 2 (Dm2) (SEQ ID NO: 27).

```
Ag2         MVVAVKVFKKSAPNGKLTVYLGKRDFIDHTDYCDPIDGVIVLDEEYLRGRKVFGQLITTY
60
Dm2         MVVSVKVFKKATPNGKVTFYLGRRDFIDHIDYCDPVDGVIVVEPDYLKNRKVFGQLATTY
60
            ***:******::****:*.***:****** *****:*****::  :**:.******.***

Ag2         RYGREEDEVMGVKFSKEMVLTKEQIYPMENANMEMTPMQERLVKKLGANAFPFTFHFPSM
120
Dm2         RYGREEDEVMGVKFSKELILCREQIVPMTNPNMEMTPMQEKLVRKLGSNAYPFTFHFPPN
120
            *****************::*  :*** **  *.*********:**:***:**:*******.

Ag2         APSSVTLQAGEDDTGKPLGVEYAIKAHVGEDESDKGHKRSAVTLTIKKLQYAPVSRGRRL
180
Dm2         SPSSVTLQQEGDDNGKPLGVEYTIRAFVGDSEDDRQHKRSMVSLVIKKLQYAPLNRGQRL
180
            :*******  **.********:*:*.*.**:.*.*:  **** *:*.********:.**:**

Ag2         PSSLVSKGFTFSQGKINLEVTLDREIYYHGEKIAANIVVTNNSRKTVKSIKCFVVQHCEV
240
Dm2         PSSLVSKGFTFSNGKISLEVTLDREIYYHGEKTAATVQVSNNSKKSVKSIKCFIVQHTEI
240
            ************:***.***************  **.:  *:***:*:*******:*** *:

Ag2         TMVNAQFSKHIASLETREGCPITPGASFTKSFFLVPLASSNKDRRGIALDGHLKEDDVNL
300
Dm2         TMVNAQFSKHVAQLETKEGCPITPGANLTKTFYLIPLAANNKDRHGIALDGHLKDEDVNL
300
            **********:*.***:*********.:**:* *:***:.****:********:*****

Ag2         ASSTLISEGKCPSDAMGIVISYSLRVKLNCGTLGGELQTDVPFKLMNPAPGSVERERVNA
360
Dm2         ASSTMVQEGKSTGDACGIVISYSVRIKLNCGTLGGEMQTDVPFKLLQPAPGTIEKKRSNA
360
            ****::.***...** *******:*:**********:********::****:.*:::.**

Ag2         LKKMKSIERHRYENSHYADDDDNIVFEDFARLRMNEPE---     398
Dm2         MKKMKSIEQHRNVKGYYQDDDDNIVFEDFAKMRMNNVNMAD   401
            :*******:**  :..:* ***********:.***:  :
```

MOSQUITO ARRESTIN 2 POLYPEPTIDES

This application is a continuation in part of co-pending U.S. patent application Ser. No. 10/056,405, filed Jan. 24, 2002, entitled "Mosquito Olfactory Genes, Polypeptides, and Methods of Use Thereof," which is hereby incorporated by reference, which claims benefit of U.S. Provisional Patent Application Ser. No. 60/264,649, filed Jan. 26, 2001, entitled "Mosquito Olfactory Genes, Polypeptides, and Methods of Use Thereof" which is hereby incorporated by reference. U.S. Provisional Patent Application Ser. No. 60/264,649, filed Jan. 26, 2001, went abandoned on Jan. 26, 2002. Be it known that I, Laurence J Zwiebel, a citizen of the United States, residing at 2512 Sunset Place, Nashville, TN 37212; have invented a new and useful "Mosquito Arrestin 2 Polypeptide."

GOVERNMENT SUPPORT CLAUSE

This invention was made with federal grant money under NIH grant 1 R01 DC04692-01 and NSF grant 0075338. The United States Government has certain rights in this invention.

A Portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to the field of host identification by insects. Specifically, the present invention relates to the identification and cloning of genes related to mosquito olfaction, identification and purification of polypeptides thereof, and methods of use thereof.

BACKGROUND OF THE INVENTION

The ability of an insect to respond to chemical stimuli is necessary for the insect to reproduce, mate, and feed. For example, insects respond to certain chemical stimuli by moving up a chemical gradient to identify and target a host. Mosquitoes, in particular, are believed to use olfaction to identify and target sources of bloodmeal for reproductive purposes. This behavior contributes to the spread of diseases in humans, such as malaria, encephalitis, and dengue fever; as well as, animal and livestock disease.

Olfaction plays a critical role in insect behaviors among agricultural pests and disease vectors. Hildebrand, et al., 1997, Annu. Rev. Neurosci, 20:595–631. In *Drosophila melanogaster* (the common fruit fly), the olfactory system functions through a rapid cycling between an on and off state of certain regulatory molecules. The olfactory signal transduction cascade is "turned on" by ligand-based activation of an odorant receptor and transduction of the signal by G-protein coupled second go messenger pathways Boekhoff et al., 1994, J. Neurosci, 14:3304–9. The "on signal" is rapidly and substantially terminated in the *Drosophila* system through the modification of the odorant receptor such that the G-protein coupled second messenger pathway is deactivated. Dohlman et al., 1991, Annual Review of Biochemistry, 60:653–88. Olfactory transduction is provided by second messenger pathways of G protein-coupled receptors. Reed, R., 1992, Neuron 8:205–209; Bloekhoff, et al, 1994, Neurosci 14:3304–3309.

The structural and functional characteristics of the mosquito olfactory system has not been characterized to date. Given the importance of the controlling this pest and disease vector, what is needed is the identification and characterization of the genes and polypeptides that function for mosquito olfaction and methods of use thereof for mosquito management.

SUMMARY OF THE INVENTION

The present invention provides, in part, nine novel mosquito polypeptides and nucleic acids encoding the polypeptides (collectively referred to herein as "mosquito olfaction molecules"). Seven of the polypeptides are novel mosquito odorant receptors and the eighth and ninth are novel mosquito arrestin molecules (see FIG. 8 and FIG. 12). The odorant receptor molecules are discovered to function in a ligand-induced signal transduction pathway for the activation of mosquito olfaction. The mosquito arrestin molecule is discovered to function to inhibit the activated signal transduction cascade. Thus, the odorant receptors can be viewed as parts of an "on switch" or an "on signal" and the arrestin molecule can be viewed as an "off switch" or an "off signal" for the odorant detection system of the mosquito. The present invention is not bound by theory or mechanism.

The present invention also provides, in part, a system for disrupting the mosquito olfactory system by disrupting, inhibiting, or otherwise interfering with the function of the off switch for mosquito olfaction. Such interference is contemplated to inhibit or degrade the ability of the mosquito to appropriately respond to chemical clues in the environment used by the mosquito for host identification and targeting. For, example, if the signal cascade cannot be terminated or inhibited, then the mosquito is impaired in following a chemical gradient to a host through sampling of the frequency of ligand-induced activation of the olfaction signal cascade. In this example, the chemical concentration of the odorant is expected to increase with decreasing distance to the target. Thus, receptor activation is expected to increase with decreasing distance to the target. It is a discovery of the present invention, that factors that inhibit the on and off cycling of the mosquito olfactory signal cascade through inhibition of signal deactivation are useful for the control of mosquitoes. Test agents used in a method for identifying mosquito olfaction molecule binding compounds would include, but are not limited to: chemicals, proteins, peptides, organic compounds and lipids. Such factors that inhibit signal deactivation may be peptides and chemicals. Several Go classes of chemicals that would be selected as targets are the carboxylic acids and steroids that are components of human sweat. Cork, A. (1996). Olfactory sensing is Aim the basis of host location by mosquitoes and other hematophagous Diptera. In Olfaction in Mosquito-Host Interactions, G. R. B. a. G. Cardew, ed. (Chichester, New York, Brisbane, Toronto, Singapor: John Wiley & Sons), pp. 71–84.Furthermore, certain aspects of the present invention are contemplated to be effective for insects in general.

Methods are presented for identifying compounds that interfere with the operation of the mosquito olfactory system resulting in an over stimulation of olfactory signaling. One consequence of interfering with the mosquito olfactory system is that the mosquito has a diminished ability to home in on sources of bloodmeal. Additionally, interfering with mosquito insect olfactory systems will inhibit mating and feeding having a significant impact on mosquito populations and is helpful, for example, in nuisance and disease vector control for humans and livestock. Interfering with non-mosquito insect olfaction will similarly have a positive impact in control of other insect populations including for the protection of crops, such as: wheat, corn, rice, cotton, and soybeans. Thus, certain aspects of the present invention provide screening assays for the identification of compositions that will reduce the ability of mosquitoes to locate sources of bloodmeal, such as humans and other mammals, including livestock (cattle, pigs, horses, sheep, etc.), show animals (horses, pigs, sheep, dogs, cats, etc.), and pets (dogs, cats, horses, etc). Certain aspects of the present invention provide a screening assay for the production of "mosquito olfaction molecules."

One aspect of the present invention provides an isolated DNA comprising a nucleotide sequence that encodes arrestin 1 polypeptide (e.g., SEQ ID NO: 2). In certain embodiments, arrestin 1 nucleotide sequence comprises a DNA molecule that hybridizes under stringent conditions to a DNA having a nucleotide sequence consisting of SEQ ID NO: 1, or the complement of SEQ ID NO: 1. Preferably the isolated DNA encodes naturally-occurring Aniopheles gambiae arrestin 1 polypeptides. In certain embodiments, the nucleotide sequence may be that of SEQ ID NO: 1. In alternate embodiments, the nucleotide sequence may encode a fragment of SEQ ID NO: 2 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 2. In certain embodiments, the isolated polynucleotide comprises a complement to a sequence that encodes a polypeptide having an amino acid sequence selected from the group consisting of SEQ ID NO: 2, and conservatively modified SEQ ID NO: 2. In alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 1 polypeptide (e.g., SEQ ID NO: 4). In certain embodiments, odorant receptor 1 nucleotide sequence comprises a DNA molecule that hybridizes under stringent conditions to a DNA having a nucleotide sequence consisting of SEQ ID NO: 3, or the complement of SEQ ID NO: 3. Preferably the isolated DNA encodes naturally-occurring Anopheles gambiae odorant receptor 1 polypeptides. In certain embodiments, the nucleotide sequence may be that of SEQ ID NO: 3. In alternate embodiments, the nucleotide sequence may encode a fragment of SEQ ID NO: 4 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 4. In certain embodiments, the isolated polynucleotide comprises a complement to a sequence that encodes a polypeptide having an amino acid sequence selected from the group consisting of SEQ ID NO: 4, and conservatively modified SEQ ID NO: 4. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention provides an isolated DNA comprising a nucleotide sequence that encodes odorant receptor 2 polypeptide (e.g., SEQ ID NO: 6). In certain embodiments, odorant receptor 2 nucleotide sequence comprises a DNA molecule that hybridizes under stringent conditions to a DNA having a nucleotide sequence consisting of SEQ ID NO: 5, or the complement of SEQ ID NO: 5. Preferably the isolated DNA encodes naturally-occurring Anopheles gambiae odorant receptor 2 polypeptides. In certain embodiments, the nucleotide sequence may be that of SEQ ID NO: 5. In alternate embodiments, the nucleotide sequence may encode a fragment of SEQ ID NO: 6 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 6. In certain embodiments, the isolated polynucleotide comprises a complement to a sequence that encodes a polypeptide having an amino acid sequence selected from the group consisting of SEQ ID NO: 6, and conservatively modified SEQ ID NO: 6. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide Jo sequence that encodes odorant receptor 3 polypeptide (e.g., SEQ ID NO: 8). In certain embodiments, odorant receptor 3 nucleotide sequence comprises a DNA molecule that hybridizes under stringent conditions to a DNA having a nucleotide sequence consisting of SEQ ID NO: 7, or the complement of SEQ ID NO: 7. Preferably the isolated DNA encodes naturally-occurring Anopheles gambiae odorant receptor 3 polypeptides. In certain embodiments, the nucleotide sequence may be that of SEQ ID NO: 7. In alternate embodiments, the nucleotide sequence may encode a fragment of SEQ ID NO: 8 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 8. In certain embodiments, the isolated polynucleotide comprises a complement to a sequence that encodes a polypeptide having an amino acid sequence selected from the group consisting of SEQ ID NO: 8, and conservatively modified SEQ ID NO: 8. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 4 polypeptide (e.g., SEQ ID NO: 14). In certain Ho embodiments, odorant receptor 4 nucleotide sequence comprises a DNA molecule that hybridizes under stringent conditions to a DNA having a nucleotide sequence consisting of SEQ ID NO: 13, or the complement of SEQ ID NO: 13. Preferably the isolated DNA encodes naturally-occurring *Anopheles gambiae* odorant receptor 4 polypeptides. In certain embodiments, the nucleotide sequence may be that of SEQ ID NO: 13. In alternate embodiments, the nucleotide sequence may encode a fragment of SEQ ID NO: 14 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 14. In certain embodiments, the isolated polynucleotide comprises a complement to a sequence that encodes a polypeptide having an amino acid sequence selected from the group consisting of SEQ ID NO: 14, and conservatively modified SEQ ID NO: 14. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 5 polypeptide (e.g., SEQ ID NO: 16). In certain to embodiments, odorant receptor 5 nucleotide sequence comprises a DNA molecule that hybridizes under stringent conditions to a DNA having a nucleotide sequence consisting of SEQ ID NO: 15, or the complement of SEQ ID NO: 15. Preferably the isolated DNA encodes naturally-occurring *Anopheles gambiae* odorant receptor 5 polypeptides. In certain embodiments, the nucleotide sequence may be that of SEQ ID NO: 15. In alternate embodiments, the nucleotide sequence may encode a fragment of SEQ ID NO: 16 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 16. In certain embodiments, the isolated polynucleotide comprises a complement to a sequence that encodes a polypeptide having an amino acid sequence selected from the group consisting of SEQ ID NO: 16, and conservatively modified SEQ ID NO: 16. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 6 polypeptide (e.g., SEQ ID NO: 18). In certain embodiments, odorant receptor 6 nucleotide sequence comprises a DNA molecule that hybridizes under stringent conditions to a DNA having a nucleotide sequence , consisting of SEQ ID NO: 17, or the complement of SEQ ID NO: 17. Preferably the isolated DNA encodes naturally-occurring *Anopheles gambiae* odorant receptor 6 polypeptides. In certain embodiments, the nucleotide sequence may be that of SEQ ID NO: 17. In alternate embodiments, the nucleotide sequence may encode a fragment of SEQ ID NO: 18 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 18.In certain embodiments, the isolated polynucleotide comprises a complement to a sequence that encodes a polypeptide having an amino acid sequence selected from the group consisting of SEQ ID NO: 18, and conservatively modified SEQ ID NO: 18. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention also provides an isolated DNA comprising a nucleotide sequence that encodes odorant receptor 7 polypeptide (e.g., SEQ ID NO: 20). In certain ho embodiments, odorant receptor 7 nucleotide sequence comprises a DNA molecule that hybridizes under stringent conditions to a DNA having a nucleotide sequence consisting of SEQ ID NO: 19, or the complement of SEQ ID NO: 19. Preferably the isolated DNA encodes naturally-occurring *Anopheles gambiae* odorant receptor 7 polypeptides. In certain embodiments, the nucleotide sequence may be that of SEQ ID NO: 19. In alternate embodiments, the nucleotide sequence may encode a fragment of SEQ ID NO: 20 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 20.In certain embodiments, the isolated polynucleotide comprises a complement to a sequence that encodes a polypeptide having an amino acid sequence selected from the group consisting of SEQ ID NO: 20, and conservatively modified SEQ ID NO: 20. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention provides a substantially pure arrestin 1 polypeptide that includes amino acid sequence that contains at least a conservatively modified identity with SEQ ID NO: 2 and binds to odorant receptors. The amino acid sequence of arrestin 1 protein can differ from SEQ ID NO: 2 by non-conservative substitutions, deletions, or insertions located at positions that do not destroy the function of the arrestin 1 polypeptide. In alternate embodiments, the polypeptide has an amino acid sequence consisting of SEQ ID NO: 2. The purified polypeptide is a polypeptide that binds specifically to an antibody that binds specifically to mosquito arrestin. In other alternate embodiments, the polypeptide comprises fragments of SEQ ID NO: 2, having at least 20 consecutive residues.

The present invention also provides a substantially pure odorant receptor 1 polypeptide that includes amino acid sequence that contains at least a conservatively modified identity with SEQ ID NO: 4 and binds to arrestin. The amino acid sequence of odorant receptor 1 polypeptide can differ from SEQ ID NO: 4 by non-conservative substitutions, deletions, or insertions located at positions that do not destroy the function of the odorant receptor 1 polypeptide. In alternate embodiments, the polypeptide has an amino acid sequence consisting of SEQ ID NO: 4. In other alternate embodiments, the polypeptide comprises fragments of SEQ ID NO: 4, having at least 20 consecutive residues.

The present invention provides a substantially pure odorant receptor 2 polypeptide that includes amino acid sequence that contains at least a conservatively modified identity with SEQ ID NO: 6 and binds to arrestin. The amino acid sequence of odorant receptor 2 polypeptide can differ from SEQ ID NO: 6 by non-conservative substitutions, deletions, or insertions located at positions that do not destroy the function of the odorant receptor 2 polypeptide. In alternate embodiments, the polypeptide has an amino acid sequence consisting of SEQ ID NO: 6. In other alternate embodiments, the polypeptide comprises fragments of SEQ ID NO: 6, having at least 20 consecutive residues.

The present invention also provides a substantially pure odorant receptor 3 polypeptide that includes amino acid sequence that contains at least a conservatively modified identity with SEQ ID NO: 8 and binds to arrestin. The amino acid sequence of odorant receptor 3 polypeptide can differ from SEQ ID NO: 8 by non-conservative substitutions, deletions, or insertions located at positions that do not destroy the function of the odorant receptor 3 polypeptide. In alternate embodiments, the polypeptide has an amino acid sequence consisting of SEQ ID NO: 8. In other alternate embodiments, the polypeptide comprises fragments of SEQ ID NO: 8, having at least 20 consecutive residues.

The present invention also provides a substantially pure odorant receptor 4 polypeptide that includes amino acid sequence that contains at least a conservatively modified identity with SEQ ID NO: 14 and binds to arrestin. The amino acid sequence of odorant receptor 4 polypeptide can differ from SEQ ID NO: 14 by non-conservative substitutions, deletions, or insertions located at positions that do not destroy the function of the odorant receptor 4 polypeptide. In alternate embodiments, the polypeptide has an amino acid sequence consisting of SEQ ID NO: 14. In other alternate embodiments, the polypeptide comprises fragments of SEQ ID NO: 14, having at least 20 consecutive residues.

The present invention also provides a substantially pure odorant receptor 5 polypeptide that includes amino acid sequence that contains at least a conservatively modified identity with SEQ ID NO: 16 and binds to arrestin. The amino acid sequence of odorant receptor 5 polypeptide can differ from SEQ ID NO: 16 by non-conservative substitutions, deletions, or insertions located at positions that do not destroy the function of the odorant receptor 5 polypeptide. In alternate embodiments, the polypeptide has an amino acid sequence consisting of SEQ ID NO: 16. In other alternate embodiments, the polypeptide comprises fragments of SEQ ID NO: 16,having at least 20 consecutive residues.

The present invention also provides a substantially pure odorant receptor 6 polypeptide that includes amino acid sequence that contains at least a conservatively modified identity with SEQ ID NO: 18 and binds to arrestin. The amino acid sequence of odorant receptor 6 polypeptide can differ from SEQ ID NO: 18 by non-conservative substitutions, deletions, or insertions located at positions that do not destroy the function of the odorant receptor 6 polypeptide. In alternate embodiments, the polypeptide has an amino acid sequence consisting of SEQ ID NO: 18. In other alternate embodiments, the polypeptide comprises fragments of SEQ ID NO: 18, having at least 20 consecutive residues.

The present invention also provides a substantially pure odorant receptor 7 polypeptide that includes amino acid sequence that contains at least a conservatively modified identity with SEQ ID NO: 20 and binds to arrestin. The amino acid sequence of odorant receptor 7 polypeptide can differ from SEQ ID NO: 20 by non-conservative substitutions, deletions, or insertions located at positions that do not destroy the function of the odorant receptor 7 polypeptide. In alternate embodiments, the polypeptide has an amino acid sequence consisting of SEQ ID NO: 20. In other alternate embodiments, the polypeptide comprises fragments of SEQ ID NO: 20, having at least 20 consecutive residues.

The invention also provides an arrestin 1 antibody, which comprises polyclonal or monoclonal antibodies. The antibody can be conjugated to a detectable label.

Another aspect of the present invention provides an arrestin 2 antibody, which comprises polyclonal or monoclonal antibodies. The antibody can be conjugated to a detectable label. Antibody labels and methods are well known in the art.

Another aspect of the present invention provides an odorant receptor 1 antibody, which comprises polyclonal or monoclonal antibodies. The antibody can be conjugated to a detectable label. Antibody labels and methods are well known in the art.

The present invention also provides an odorant receptor 2 antibody, which comprises polyclonal or monoclonal antibodies. The antibody can be conjugated to a To detectable label.

Another aspect of the present invention provides an odorant receptor 3 antibody, which comprises polyclonal or monoclonal antibodies. The antibody can be conjugated to a detectable label.

Another aspect of the present invention provides an odorant receptor 4 antibody, which comprises polyclonal or monoclonal antibodies. The antibody can be conjugated to a detectable label.

Another aspect of the present invention provides an odorant receptor 5 antibody, which comprises polyclonal or monoclonal antibodies. The antibody can be conjugated to a detectable label.

Another aspect of the present invention provides an odorant receptor 6 antibody, which comprises polyclonal or monoclonal antibodies. The antibody can be conjugated to a detectable label.

Another aspect of the present invention provides an odorant receptor 7 antibody, which comprises polyclonal or monoclonal antibodies. The antibody can be conjugated to a detectable label.

The present invention also presents a method of producing arrestin 1 protein. The method includes the following steps: (a) providing a cell transformed with an isolated DNA comprising a nucleotide sequence that encodes an amino acid sequence to of SEQ ID NO: 2; (b) culturing the cell; and (c) collecting from the cell or the medium of the cell the polypeptide encoded by the polynucleotide sequence. Certain alternatives to SEQ ID NO: 2 are described above (e.g. conservative variants and hybridization variants).

The present invention also provides a method of manufacturing odorant receptor 1 protein. The method includes the following steps: (a) providing a cell transformed with an isolated DNA comprising a nucleotide sequence that encodes an amino acid sequence of SEQ ID NO: 4; (b)

culturing the cell; and (c) collecting from the cell or the medium of the cell the polypeptide encoded by the polynucleotide sequence.

The present invention provides a method of manufacturing odorant receptor 2 protein. The method includes the following steps: (a) providing a cell transformed with an isolated DNA comprising a nucleotide sequence that encodes an amino acid sequence of SEQ ID NO: 6; (b) culturing the cell; and (c) collecting from the cell or the medium of the cell the polypeptide encoded by the polynucleotide sequence.

The present invention also provides a method of manufacturing odorant receptor 3 protein. The method includes the following steps: (a) providing a cell transformed with an isolated DNA comprising a nucleotide sequence that encodes an amino acid sequence of SEQ ID NO: 8; (b) culturing the cell; and (c) collecting from the cell or the medium of the cell the polypeptide encoded by the polynucleotide sequence.

The present invention also provides a method of manufacturing odorant receptor 4 protein. The method includes the following steps: (a) providing a cell transformed with an isolated DNA comprising a nucleotide sequence that encodes an amino acid sequence of SEQ ID NO: 14; (b) culturing the cell; and (c) collecting from the cell or the medium of the cell the polypeptide encoded by the polynucleotide sequence.

The present invention also provides a method of manufacturing odorant receptor 5 protein. The method includes the following steps: (a) providing a cell transformed with an isolated DNA comprising a nucleotide sequence that encodes an amino acid sequence of SEQ ID NO: 16; (b) culturing the cell; and (c) collecting from the cell or the medium of the cell the polypeptide encoded by the polynucleotide sequence.

The present invention also provides a method of manufacturing odorant receptor 6 protein. The method includes the following steps: (a) providing a cell transformed with an isolated DNA comprising a nucleotide sequence that encodes an amino acid sequence of SEQ ID NO: 18; (b) culturing the cell; and (c) collecting from the cell or the medium of the cell the polypeptide encoded by the polynucleotide sequence.

The present invention also provides a method of manufacturing odorant receptor 7 protein. The method includes the following steps: (a) providing a cell transformed with an isolated DNA comprising a nucleotide sequence that encodes an amino acid sequence of SEQ ID NO: 20; (b) culturing the cell; and (c) collecting from the cell or the medium of the cell the polypeptide encoded by the polynucleotide sequence.

The present invention also provides a method for identifying a mosquito olfaction molecule binding compound. The method includes the following steps: (a) providing an isolated mosquito olfaction molecule; (b) contacting a test agent with the isolated mosquito olfaction molecule; and (c) detecting whether the test agent is bound to the isolated mosquito olfaction molecule. Methods of detection are well known in the art. In certain embodiments, the isolated mosquito olfaction molecule further comprises a polypeptide having an amino acid sequence as set forth in SEQ ID NO: 2 or variants thereof as described herein (As used herein this statement means conservatively modified variants, hybridization variants, and variants to which antibodies bind specifically). In still other embodiments, the isolated mosquito olfaction molecule further comprises a polypeptide having an amino acid sequence as set forth in SEQ ID NO: 25 or variants thereof as described herein (As used herein this statement means conservatively modified variants, hybridization variants, and variants to which antibodies bind specifically). In alternate embodiments, the isolated mosquito olfaction molecule further comprises a polypeptide having an amino acid sequence selected from the group consisting of SEQ ID NO: 2, SEQ ID NO. 4, SEQ ID NO. 6, SEQ ID NO. 8, SEQ ID NO. 14, SEQ ID NO. 16, SEQ ID NO. 18, SEQ ID NO. 20. conservatively modified SEQ ID NO: 4, conservatively modified SEQ ID NO: 6, conservatively modified SEQ ID NO: 8, conservatively modified SEQ ID NO: 14, conservatively modified SEQ ID NO: 16, conservatively modified SEQ ID NO: 18, and conservatively modified SEQ ID NO: 20. In other embodiments, contacting the test agent with the isolated mosquito olfaction molecule further comprises contacting under native conditions. In alternate embodiments, detecting specific binding of the test agent to the isolated mosquito olfaction molecule further comprises immunoprecipitation.

The present invention also presents a screening method for identifying a compound that inhibits binding of mosquito arrestin to a mosquito odorant receptor. The method includes the following steps: (a) providing an antibody that binds to an isolated mosquito olfaction molecule; (b) providing a mosquito olfaction molecule binding compound; (c) providing a test sample comprising the mosquito arrestin polypeptide and mosquito odorant receptor; (d) combining the mosquito olfaction molecule binding compound, the antibody, and the test sample in reaction conditions that allow a complex to form in the absence of the mosquito olfaction molecule binding compound., wherein the complex includes the antibody, mosquito arrestin and mosquito odorant receptor; and (e) determining whether the mosquito olfaction molecule binding compound decreases the formation of the complex, wherein a decrease indicates that the mosquito olfaction molecule binding compound is a compound that inhibits the binding of mosquito arrestin to mosquito odorant receptor. In certain embodiments, the mosquito odorant receptor further comprises a polypeptide having any of the following sequences: SEQ ID NO: 4, SEQ ID NO: 6, SEQ ID NO: 8, SEQ ID NO: 14, SEQ ID NO: 16, SEQ ID NO: 18, SEQ ID NO: 20, conservatively modified SEQ ID NO: 4, conservatively modified SEQ ID NO: 6, conservatively modified SEQ ID NO: 8, conservatively modified SEQ ID NO: 16, conservatively modified SEQ ID NO: 18, conservatively modified SEQ ID NO: 20 or conservatively modified SEQ ID NO: 14.

The present invention also provides an isolated DNA comprising a nucleotide sequence that encodes the arrestin 2 polypeptide (e.g., SEQ ID NO: 25). In certain embodiments, the arrestin 2 nucleotide sequence comprises a DNA molecule that hybridizes under stringent conditions to a DNA having a nucleotide sequence consisting of SEQ ID NO: 26, or the complement of SEQ ID NO: 26. Preferably the isolated DNA encodes naturally-occurring *Anopheles gambiae* arrestin 2 polypeptide. In certain embodiments, the nucleotide sequence may be that of SEQ ID NO: 26. In alternate embodiments, the nucleotide sequence may encode a fragment of SEQ ID NO: 25 at least 20 residues in length. One of ordinary skill in the art knows that a polypeptide fragment having a length of 20 residues is capable of functioning as an immunogen. In certain embodiments, the nucleotide sequence may encode a polypeptide having a conservatively modified amino acid sequence of SEQ ID NO: 25.In certain embodiments, the isolated polynucleotide comprises a complement to a sequence that encodes a polypeptide having an amino acid sequence selected from the group consisting of SEQ ID NO: 25, and conservatively modified SEQ ID NO: 25. In other alternate embodiments, the nucleotide sequence may be that of degenerate variants of above-mentioned sequences. The invention also includes operably linking one or more expression control sequences to any of the above-mentioned nucleotide sequences. The invention also includes a cell comprising any of the above-mentioned nucleotide sequences operably linked to one or more expression control sequences.

The present invention provides a substantially pure arrestin 2 polypeptide that includes amino acid sequence that contains at least a conservatively modified identity with SEQ ID NO: 25 and is reasonably believed to bind to odorant receptors. The amino acid sequence of arrestin 2 protein can differ from SEQ ID NO: 25 by non-conservative substitutions, deletions, or insertions located at positions that do not destroy the function of the arrestin 2 polypeptide. In alternate embodiments, the polypeptide has an amino acid sequence consisting of SEQ ID NO: 25. The purified polypeptide is a polypeptide that binds specifically to an antibody that binds specifically to mosquito arrestin. In other alternate embodiments, the polypeptide comprises fragments of SEQ ID NO: 25, having at least 20 consecutive residues.

The present invention also presents a method of producing arrestin 2 protein. The method includes the following steps: (a) providing a cell transformed with an isolated DNA comprising a nucleotide sequence that encodes an amino acid sequence of SEQ ID NO: 2; (b) culturing the cell; and (c) collecting from the cell or the medium of the cell the polypeptide encoded by the polynucleotide sequence. Certain alternatives to SEQ ID NO: 25 are described above (e.g. conservative variants and hybridization variants).

Various features and advantages of the invention will be apparent from the following detailed description and from the claims.

BRIEF DESCRIPTION OF THE DRAWINGS

FIG. 1 is the nucleotide sequence (SEQ ID NO: 9) of odorant receptor 1 isolated from *Anopheles gambiae*.

FIG. 2 the nucleotide sequence (SEQ ID NO: 10) of odorant receptor 2 isolated from *Anopheles gambiae*.

FIG. 3 is the nucleotide sequence (SEQ ID NO: 11) of odorant receptor 3 isolated from *Anopheles gambiae*.

FIG. 4 is the nucleotide sequence (SEQ ID NO: 12) of odorant receptor 4 isolated from *Anopheles gambiae*.

FIG. 5 is a table of preferred codons used to deduce amino acid sequences from nucleotide sequences for *Anopheles gambiae*.

FIG. 6 is a table listing cDNA and polypeptide sequences with corresponding SEQ ID numbers.

FIG. 7 is the nucleotide sequence (SEQ ID NO: 21) of odorant receptor 5 isolated from *Anopheles gambiae*.

FIG. 8 is the nucleotide sequence (SEQ ID NO: 22) of odorant receptor 6 isolated from *Anopheles gambiae*.

FIG. 9 is the nucleotide sequence (SEQ ID NO: 23) of odorant receptor 7 isolated from *Anopheles gambiae*.

FIG. 10 is the nucleotide sequence (SEQ ID NO: 24) of arrestin 2 isolated from *Anopheles gambiae*.

FIG. 11 is an alignment of *Anopheles gambiae* arrestin 2 (SEQ ID NO: 25) with *D. melanogaster* arrestin 2 (SEQ ID NO: 27), also called ArrB. Clustal W alignment of predicted amino acid sequences of arrestin 2 genes from *A. gambiae* and *D. melanogaster*. Overall homology is indicated by the use of three characters. "*" indicates positions which have a single, fully conserved residue. ":" indicates that one of the following strong groups is fully conserved: STA; NEQK; NHQK; NDEQ; QHRK; MILV; MILF; HY; FYW. "." indicates that one of the following weaker groups is fully conserved: CSA; ATV; SAG; STNK; STPA; SGND; SNDEQK; NDEQHK; NEQHRK; FVLIM; HFY. Thompson, et al., 1994, Nucleic Acids Res., 22:4673–4680.

DETAILED DESCRIPTION OF THE INVENTION

Arrestins interact with odorant receptors to cause changes in cellular function. Interruption of normal arrestin function will lead to over stimulation of the olfaction do system. Consequently, substances that block the arrestin-odorant receptor interaction can interfere with a mosquito's ability to home in on sources of bloodmeal, such as humans. Screening for substances that modulate arrestin-odorant receptor interaction is therefore useful for identifying pest control agents and for treatment of malaria. The deduced amino acid sequence and arrestin contains several domains implicated in arrestin function. The motifs include consensus Src homology 3 (SH3) binding sites. Cohen, et al., 1995, Cell, 80:237. Sequence comparisons with the DDBJ/EMBL/GenBank and SWISSPROT databases were performed using the GCG software. Devereux, et al., 1984, Nucleic Acids Res., 12:387–395. Protein alignment was also performed using the Clustal W software package. Thompson, et al., 1994, Nucleic Acids Res, 22:4673–4680. Additionally, arrestin 1 has been submitted to the GenBank database with accession No. AY017417. FIG. 13 shows an alignment of *Anopheles gambiae* arrestin 2 with the arrestin 2 from *Drosophila melanogaster*, accesion number P19107 (genbank-swissprot). Yamada, et al., 1990, Science, 248:483–486. Additional information regarding arrestins is found in Merrill, et al., 2002, Proc. Natl. Acad. Sci. USA, 99:1633–1638; Nighorn and Hildebrand, 2002, Proc. Natl. Acad. Sci. USA, 99:1113–1114.

As used herein, "native conditions" means natural conditions as found within the ordinary conditions found within *Anopheles gambiae*.

As used herein, "stringent conditions" means the following: hybridization at 42° C. in the presence of 50% formamide; a first wash at 65° C. with about 2×SSC containing 1% SDS; followed by a second wash at 65° C. with 0.1×SSC. Salt concentrations and temperature may be modified. Such modifications may be found in Sambrook et al., 1989, Molecular Cloning: A Laboratory Manual (2nd Edition), Cold Spring Harbor Press, Cold Spring Harbor, N.Y. The hybridizing part of the nucleic acid is generally at least 15 nucleotides in length.

As used herein, "purified polypeptide" means a polypeptide that is substantially free from compounds normally associated with the polypeptide in the natural state. The absence of such compounds may be determined by detection of protein bands subsequent to SDS-PAGE. Purity may also be assessed in other ways known to those of ordinary skill in the art. The term, as defined herein, is not intended to exclude (1) synthetic or artificial combinations of the polypeptides with other compounds, (2) polypeptides having minor impurities which do not interfere with biological activity.

As used herein, "isolated polynucleotide" means a polynucleotide having a structure that is not identical to any naturally occurring nucleic acid or of any fragment of a naturally occurring genomic nucleic acid spanning more than three separate genes. Thus, the term includes (1) a nucleic acid incorporated into a vector or into the genomic DNA of a prokaryote or eukaryote in a manner such that the resulting molecule is not identical to any naturally occurring vector or genomic DNA; (2) a separate molecule of a cDNA, a genomic fragment, a fragment produced by polymerase chain reaction (PCR), or a restriction fragment; and (3) a recombinant nucleotide sequence that is part of a gene encoding a fusion protein. This definition of "isolated polynucleotide" supersedes and controls all other definitions known in the art.

As used herein, "hybridization probe" means nucleic acid that is labeled for detection, such as labeling with radiation. Hybridization probes are well known in the art.

As used herein, "culturing the cell" means providing culture conditions that are conducive to polypeptide expression. Such culturing conditions are well known in the art.

As used herein, "operably linked" means incorporated into a genetic construct so that expression control sequences effectively control expression of a gene of interest.

As used herein, "protein" means any peptide-linked chain of amino acids, regardless of length or post-translational modification, e.g., glycosylation or phosphorylation.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, "mosquito olfaction molecule" means a polypeptide that is involved in the modulation of the mosquito olfaction system. By way of illustration, and not limitation, mosquito olfaction molecules have the following characteristics: (1) G protein-coupled seven-transmembrane domain receptors, (2) sequence conservation regarding positions of a subset of introns and the length of the deduced protein, (3) they are selectively expressed in olfactory receptor neurons, and (4) they have highly conserved structural motifs. Odorant receptors 3, 4 and 5 are clustered tightly together within the *A. gambaie* genome. Odorant receptor 5 and odorant receptor 4 are separated by 310 bp while odorant receptor 4 and odorant receptor 3 No are separated by 747 bp. An additional characteristic of odorant and taste receptor genes is the close chromosomal linkage. Such linkage has been demonstrated in the *D. melanogaster* and odorant receptor genes from *C. elegans* and mouse. Clyne, et al., 1999, Neuron, 22:327–338; Vosshall, et al., 1999, Cell, 96:725–736; Vosshall, et al., 2000, Cell, 102:147–159; Clyne, et al., 2000, Science, 287:1830–1834; Gao and Chess 1999, Genomics, 60:31–39; Troemel, et al., 1995, Cell, 83:207–218; Xie, et al., 2000, Genome, 11:1070–1080. Fox et. al., 2001, PNAS 98:14693–14697. This group of molecules includes odorant receptor 1 (SEQ ID NO: 4), odorant receptor 2 (SEQ ID NO: 6), odorant receptor 3 (SEQ ID NO: 8), odorant receptor 4 (SEQ ID NO: 14), odorant receptor 5 (SEQ ID NO: 16), odorant receptor 6 (SEQ ID NO: 18), odorant receptor 7 (SEQ ID NO: 20), arrestin 1 (SEQ ID NO: 2), arrestin 2 (SEQ ID NO: 25) and variants thereof as described herein.

As used herein, "odorant receptor" means any molecule performing the functional role of an odorant receptor, as described herein and in the scientific literature. Examples of odorant receptors included, but are not limited to, odorant receptor 1, odorant receptor 2, odorant receptor 3, odorant receptor 4, odorant receptor 5, odorant receptor 6, and odorant receptor 7.

As used herein, "mosquito olfaction molecule binding compound" means a compound that specifically binds to a mosquito olfaction molecule. Mosquito olfaction molecules additionally include polypeptides having the characteristics noted in the definition of the term.

As used herein, "mosquito olfaction molecule-specific antibody" means an antibody that binds to a mosquito olfaction molecule. The term includes polyclonal and monoclonal antibodies.

As used herein, "substantially pure protein" means a protein separated from components that naturally accompany it. Typically, the protein is substantially pure when it is at least 60%, by weight, free from the proteins and other naturally-occurring organic molecules with which it is naturally associated. In certain embodiments, the purity of the preparation is at least 75%, more preferably at least 90%, 95% and most preferably at least 99%, by weight. A substantially pure mosquito olfaction molecule protein can be obtained, for example, by extraction from a natural source, by expression of a recombinant nucleic acid encoding a mosquito olfaction molecule polypeptide, or by chemical synthesis. Purity can be measured by any appropriate method, e.g., column chromatography, polyacrylamide gel electrophoresis, or HPLC analysis. A chemically-synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in *E. coli* or other prokaryotes.

As used herein, "fragment", as applied to a polypeptide (e.g., arrestin 1 polypeptide), means at least about 10 amino acids, usually about 20 contiguous So amino acids, preferably at least 40 contiguous amino acids, more preferably at least 50 amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

As used herein, "test sample" means a sample that contains arrestin 1, or conservatively modified variant thereof, or arrestin 2, or conservatively modified variant thereof in combination with at least one of the following: odorant receptor 1, odorant receptor 2, odorant receptor 3, odorant receptor 5, odorant receptor 6, odorant receptor 7, odorant receptor 4, conservatively modified variants of the above, or other odorant receptors known in the art. A test sample is also a sample that contains any fragment, having at least 20 consecutive residues, of any of the above mentioned arresting or odorant receptors.

As used herein, "vector" means a replicable nucleic acid construct, e.g., a plasmid or viral nucleic acid. Preferably, expression is controlled by an expression control sequence.

As used herein, "conservatively modified" applies to both amino acid and nucleic acid sequences. Regarding nucleic acid sequences, conservatively modified refers to those nucleic acids which encode identical or conservatively modified variants of the amino acid sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Every nucleic acid sequence herein which encodes a polypeptide also describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide So sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W.H. Freeman and Company.

As used herein, "immunogenic fragment" means the fragment of a polypeptide that is capable of eliciting an immunogenic response.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Structure and Function

The genes disclosed herein have homology to corresponding arrestin and odorant receptor *Drosophila melanogaster* genes. Fox, et al., 2001, PNAS 98:14693–14697. The genes disclosed herein have the utility disclosed within this patent application.

A full-length *Anopheles gambiae* arrestin 1 cDNA has been cloned and sequenced. The arrestin 1 cDNA clone contains 1964 bp and includes a complete open reading frame that encodes a protein 383 amino acids in length. The open reading frame from the methionine includes 383 amino acids, yielding a slightly basic polypeptide (PI=8.0) with a predicted molecular weight of 42.8 KD.

A full-length *Anopheles gambiae* arrestin 2 cDNA has been cloned and sequenced. The arrestin 2 cDNA clone contains 1190 bp and includes a complete open reading frame that encodes a protein 398 amino acids in length.

Expression Control Sequences and Vectors

The mosquito olfaction molecules of this invention can be used in a method to identify a mosquito olfaction molecule binding compound. If desired, the mosquito olfaction molecule binding compounds may be further tested for ability to inhibit binding of arrestin to an odorant receptor. Methods for this test are described herein. In certain embodiments, the DNA that encodes the arrestin 1 polypeptide ("ARR1 DNA") may be cloned into an expression vector, i.e., a vector wherein ARR1 DNA is operably linked to expression control sequences. The need for expression control sequences will vary according to the type of cell in which the ARR1 DNA is to be expressed. Generally, expression control sequences include a transcriptional promoter, enhancer, suitable mRNA ribosomal binding sites, and sequences that terminate transcription and translation. One of ordinary skill in the art can select proper expression control sequences. Standard methods can be used by one skilled in the art to construct expression vectors. See generally, Sambrook et al., 1989, Molecular Cloning: A Laboratory Manual (2nd Edition), Cold Spring Harbor Press, Cold Spring Harbor, N.Y. Vectors useful in this invention include, but are not limited to plasmid vectors and viral vectors.

All other nucleic acid sequences disclosed herein may also be operably linked to expression control sequences. The expression control sequences described above may be used. As mentioned above, methods known to those of ordinary skill in the art may be used to insert nucleic acid sequences into expression control sequences. Methods known to those of ordinary skill in the art may be used to introduce the nucleic acid and expression control sequence into eukaryotic and/or prokaryotic cells. An example of prokaryotic cells is BL21 (DE3)pLysS bacteria. An example of eukaryotic cells is Sf9.

In certain embodiments of the invention, ARR1 DNA is introduced into, and expressed in, a prokaryotic cell, e.g., BL21 (DE3)pLysS bacteria. In other embodiments of the invention, DNA encoding the arrestin 2 polypeptide (SEQ ID NO: 25) is introduced into, and expressed in, a prokaryotic cell, e.g., BL21 (DE3)pLysS bacteria.

In certain embodiments of the invention, the ARR1 DNA is introduced into, and expressed in, a eukaryotic cell in vitro. In other emobidments of the present invention, DNA encoding the arrestin 2 polypeptide (SEQ ID NO: 25) is introduced into, and expressed in, a eukaryotic cell in vitro. Eukaryotic cells useful for expressing such DNAs in vitro include, but are not limited to Sf9 cells. Transfection of the eukaryotic cell can be transient or stable.

Mosquito Olfaction Molecule-Specific Antibody

An animal is immunized with a mosquito olfaction molecule (e.g., arrestin 1 polypeptide). The animal produces antibodies to the mosquito olfaction molecule. The production and collection of the polyclonal antibodies was performed by Lampire Biological Laboratories, Inc. of Pipersville, Pa. 18947, using techniques known in the art.

Mosquito Olfaction Molecule Antibody Label

In some embodiments of the invention, the mosquito olfaction molecule-specific antibody includes a detectable label. Many detectable labels can be linked to, or incorporated into, an antibody of this invention. The following are examples of useful labels: radioactive, non-radioactive isotopic, fluorescent, chemiluminescent, paramagnetic, enzyme, or colorimetric.

Examples of useful enzyme labels include malate hydrogenase, staphylococcal dehydrogenase, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, and glucoamylase, acetylcholinesterase. Examples of useful radioisotopic labels include $^3H$, $^{131}I$, $^{125}I$, $^{32}P$, $^{35}S$, and $^{14}C$. Examples of useful fluorescent labels include fluorescein, rhodamine, phycoerythrin, phycocyanin, allophycocyanin, and fluorescamine. Examples of useful chemiluminescent label types include luminal, isoluminal, aromatic acridinium ester, imidazole, acridinium salt, oxalate ester, luciferin, luciferase, and aequorin.

Antibody labels can be coupled to, or incorporated into antibodies by use of common techniques known to those of ordinary skill in the art. Typical techniques are described by Kennedy et al., 1976, Clin. Chim. Acta, 70:1–31; and Schurs et al., 1977, Clin. Chim. Acta, 81: 1–40. Useful chemical coupling methods include those that use glutaraldehyde, periodate, dimaleimide and m-maleimido-benzyl-N-hydroxy-succinimide ester.

Screening assays

The present invention provides, in part, a screen for mosquito olfaction molecule binding compounds with the ability to interrupt the interaction of arrestin with an odorant receptor. Identifying that a test agent will bind a mosquito olfaction molecule is one part. Once a test agent has demonstrated its ability to bind a mosquito olfaction molecule, it is properly called a mosquito olfaction molecule binding compound. Since it is possible for a mosquito olfaction molecule binding compound to bind without necessarily interrupting the arrestin-odorant receptor interaction, it is proper to further assay in order to determine that the interaction is disrupted. The ability of the mosquito olfaction molecule binding compound to interrupt the arrestin-odorant receptor interaction may be assayed.

In certain embodiments, a test agent is identified as a mosquito olfaction molecule binding compound by the following method. One of the mosquito olfaction molecules is immobilized (e.g., arrestin 1). Polypeptides can be immobilized using methods known in the art. Such methods include the use of Affigel (Biorad) or activated agarose or sepharose to which significant amounts of polypeptides can be directly coupled. The immobilized polypeptide (e.g., arrestin 1) is contacted with the test agent. Unbound test agent can be removed by washing with binding buffer. Then, the bound test agent is eluted by a salt gradient. The material that is bound to the immobilized polypeptide may be purified by SDS-PAGE. Other methods known by one of ordinary skill in the art for identifying an interaction between two proteins include affinity purification, co-immunoprecipitation, and far-western blotting.

In certain embodiments, the following method is used to screen for substances capable of interrupting arrestin-odorant receptor interaction. The following method of detecting protein-protein interaction will also provide information regarding the lack of protein-protein interactions. The two-hybrid method is a well known genetic assay used to detect protein-protein interactions in vivo. See, e.g., Bartel et al., 1993, In Cellular Interactions in Development: A Practical Approach, Oxford University Press, Oxford, pp. 153–179; Chien et al., 1991, Proc. Natl. Acad. Sci. USA, 88:9578–9582; Fields et al., 1989, Nature, 340:245–247; Fritz et al., 1992, Curr. Biol., 2:403–405; Guarente, L., 1993, Proc. Natl. Acad. Sci. USA, 90:1639–1641. There are multiple combinations available between arrestin and the seven odorant receptors. A GAL4 binding domain is linked to an So arrestin fragment (e.g., arrestin 1 polypeptide) and a GAL4 transactivation domain is linked to an odorant receptor fragment (e.g., odorant receptor 1 polypeptide). A GAL4 binding site is linked to a reporter gene such as lacZ. All three elements are contacted in the presence and absence of a mosquito olfaction molecule binding compound. The level of expression of the reporter gene is monitored. A decrease in the level of expression of lacZ means that the mosquito olfaction molecule binding compound interrupts the interaction of arrestin with the odorant receptor.

In an alternate embodiment, the following is a method that will identify whether a mosquito olfaction molecule binding compound will interrupt the interaction between arrestin and an odorant receptor. The following method of co-immunoprecipitation may make use of the available panel of antibodies to any arrestin or odorant receptor. Since this method makes use of antibodies that demonstrate the ability to immunoprecipitate the mosquito olfaction molecule and other proteins to which it is bound, the ability of a mosquito olfaction molecule binding compound to inhibit the interaction of the mosquito olfaction molecule will serve as the measure of the compound's interruption ability.

Also disclosed herein is a method of modulating arrestin biological activity. In certain embodiments, the method comprises administering an arrestin biological activity-modulating amount of a mosquito olfaction molecule binding compound. Upon administration, arrestin 1, or arrestin 2, is contacted with the mosquito olfaction molecule binding compound. Such contact results in modulating arrestin 1, Do or arrestin 2, biological activity. The mosquito olfaction molecule binding compound may be administered as an aerosol, solid, or liquid, such that delivery occurs through contact with the body of the target subject. For example, administration may occur by absorption through the exterior surfaces of the target subject, ie. mosquitoes, or by intake through other apertures of the target subject [proboscis (or other feeding aperture), or spiracles (or other respiratory apertures]. An activity-modulating amount of mosquito olfaction molecule binding compound is an amount that is sufficient to prohibit at least about 50% of the arrestin molecules, meaning arrestin 1 (SEQ ID NO: 2), arrestin 2 (SEQ ID NO: 25), or variants thereof, from interacting with any odorant receptors.

All citations and references described in this patent application are hereby incorporated herein by reference, in their entirety. Also incorporated in this specification are the exhibits filed herewith. The present invention is further illustrated by the following specific examples. The examples are provided for illustration only and are not to be construed as limiting the scope or content of the invention in any way.

EXAMPLE 1

Protein Expression

A cDNA encoding arrestin 2 is subcloned into the pBlueScript II (KS) vector (Novagen, Madison, Wis.) at the BamHI/NdeI restriction sites for DNA sequencing. The cDNA encoding arrestin 2 is subsequently subcloned into the bacterial expression plasmid pET15b (Novagen, Madison, Wis.). The bacterial expression plasmid containing the arrestin 2 cDNA is transformed into BL21 (DE3)pLysS bacteria (Novagen, Madison, Wis.) for high levels of arrestin 2 expression. Methods are known in the art for isolating the expressed protein.

Expression of other nucleic acids disclosed herein is achieved by using the above-referenced method. Once the odorant receptor is in protein form, it may be used as described within this application.

EXAMPLE 2

Mosquito Olfaction Molecule Specific Antibody

The cDNA encoding arrestin 2 is subcloned into the bacterial expression plasmid pET15b (Novagen, Madison, Wis.). The vector is transformed into BL21 (DE3)pLysS bacteria (Novagen, Madison, Wis.) for high levels of arrestin 2 expression. Rapid purification is performed using His-Bind affinity Resin (Novagen, Madison, Wis.). Native recombinant arrestin 2 is then denatured using gel purification on SDS-polyacrylamide gel electrophoresis followed by staining with 0.05% Coomassie Brilliant Blue (Sigma-Aldrich, St. Louis, Mo.). Polyclonal antibodies were generated in rabbits by Lampire Biological Laboratories, Inc. of Pipersville, Pa. 18947. Polyclonal antibodies may be generated for any of the odorant receptors disclosed herein.

EXAMPLE 3

Identification of a Mosquito Olfaction Molecule Binding Compound

Arrestin 2 polypeptide is expressed in and purified from BL21 (DE3)pLysS bacteria (Novagen, Madison, Wis.). Arrestin 2 is incubated with a test agent in Phosphate Buffered Saline (pH 7.5), 0.1% Tween-20, and 0.1% broad spectrum protease inhibitors for 90 minutes at 4° C. Anti-arrestin 2 polyclonal sera is added to the reaction at a dilution of 1:2000 and incubated for an additional 60 minutes. The complexes, consisting of either polypeptide-antibody or test agent-polypeptide-antibody are isolated by the addition of $1 \times 10^7$ Dynalbeads M280 (sheep anti-Rabbit IgG) followed by incubation at the same temperature for an additional 60 minutes. Isolation of the complexes is completed by using the DYNAL Magnetic Particle Concentrator (Dynal Inc., Lake Success, N.Y.). The complexes are washed three times with broad spectrum protease inhibitors. Content of the complexes is assayed by SDS-PAGE followed by silver staining and western blotting. Common methods are known by those of ordinary skill in the art for silver staining and western blotting. See generally, Sambrook et al., 2001, Molecular Cloning: A Laboratory Manual (3rd Edition), Cold Spring Harbor Press, Cold Spring Harbor, N.Y. Obviously, the presence of the test agent, polypeptide, and antibody indicates that the test agent binds to the polypeptide.

EXAMPLE 4

Identification of a Compound That Inhibits Binding of Arrestin to an Odorant Receptor Arrestin 2 polypeptide and odorant receptor 1 polypeptide are expressed in and purified from BL21 (DE3)pLysS bacteria (Novagen, Madison, Wis.). Arrestin 2 polypeptide and odorant receptor 1 polypeptide are incubated with a mosquito olfaction molecule binding compound in Phosphate Buffered Saline (pH 7.5), 0.1% Tween-20, and 0.1% broad spectrum protease inhibitors for 90 minutes at 4° C. Anti-arrestin 2 polyclonal sera is added to the reaction at a dilution of 1:2000 and incubated for an additional 60 minutes. The complexes, consisting of either antibody-arrestin 2-odorant receptor 1 or antibody-arrestin 2, are isolated by the addition of $1 \times 10^7$ Dynalbeads M280 (sheep anti-Rabbit IgG) followed by incubation at the same temperature for an additional 60 minutes (Dynal Inc., Lake Success, N.Y.). Once the isolation of the complexes is completed by using the DYNAL Magnetic Particle Concentrator, (Dynal Inc., Lake Success, N.Y.), the complexes are washed three times with broad spectrum protease inhibitors. The content of the complexes is assayed by SDS-PAGE followed by silver staining and western blotting. Common methods are known by those of ordinary skill in the art for silver staining and western blotting. See generally, Sambrook et al., 2001, Molecular Cloning: A Laboratory Manual (3rd Edition), Cold Spring Harbor Press, Cold Spring Harbor, N.Y.

EXAMPLE 5

Far Western Blotting to Analyze Components of a Protein Mixture

The protein sample is fractionated on an SDS-PAGE gel. After electrophoresis at a voltage and time that is known in the art, the proteins are transferred from the gels onto a solid support membrane by electroblotting. Transferred membranes may be stained with Ponceau S to facilitate location and identification of specific proteins. Nonspecific sites on the membranes are blocked with standard blocking reagents, and the membranes are then incubated with a radiolabeled non-antibody protein probe. After washing, proteins that bind to the probe are detected by autoradiography.

The content of the solutions used within this protocol are disclosed in Wiley's Current Protocols in Cell Biology.

The protein sample to be analyzed is resuspended in 1×SDS sample buffer. Approximately 50 to 100 ug can be loaded in each lane of the gel. The samples are separated with SDS-PAGE. The proteins are transferred to nitrocellulose by electroblotting.

After transfer, stain the membrane for 5 min in ~100 ml freshly diluted 1× Ponceau S staining solution. The membrane is then destained by washing it in several changes of deionized water until the proteins are clearly visible. Continue to destain for an additional 5 min in water until the red staining fades.

The membrane is then blocked for 2 hr in 200 ml blocking buffer I at room temperature with gentle agitation. Incubate the membrane in 200 ml of blocking buffer II for 2 hours and rinse the membrane briefly in 100 ml of 1×PBS.

Prior to probing, the membrane is preincubated for 10 min in 50 ml of 1× probe dilution buffer without the probe at room temperature. The probe is added to the membrane and incubated for 2 hours at room temperature. The membrane is washed with 200 ml 1×PBS for 5 min, room temperature.

Repeat the wash step three additional times. Air dry the filter and expose to x-ray film with intensifying screen. An overnight exposure is typically sufficient.

cDNA Nucleic Acid Sequence
1964 nucleotides
Mosquito arrestin 1

ACAGGAACGACGGTTGTGATCCCTCCACTGGTGGTGACA SEQ ID NO:1
CGAATCATAAGCATTATTTCATACCTAAAAAACAAAATC
TACAAAAAAAAGCTTCATTCCCATCGAAAAAACTTTCTT
GTGAAATCAACCGAGCTAACAAACAACATCCTGTGCAAA
ATCTAGCAGTGAAAGTGTGATATCGTATACCTGTACCTG
TAAACCGTTGTGCGCGTGTGTGCCTTTGTGTATCAATTT
TGTGGAAAACAGAAAATACATCAAAATGGTTTACAATTT
CAAAGTCTTCAAGAAGTGCGCCCCTAATGGAAAGGTTAC
GCTGTACATGGGCAAGCGTGACTTTGTAGACCACGTTTC
CGGCGTTGAACCGATCGATGGTATCGTCGTCCTCGATGA
TGAGTACATTCGTGACAACCGTAAGGTATTCGGTCAGAT
TGTCTGCAGTTTCCGCTACGGCCGCGAAGAGGACGAGGT
GATGGGACTAAACTTCCAGAAGGAGTTATGCCTCGCTTC
CGAACAGATCTACCCGCGTCCGGAAAAGTCGGACAAGGA
GCAGACCAAGCTCCAGGAGCGACTGCTGAAGAAGCTGGG
TTCGAACGCCATCCCGTTCACGTTCAACATCTCGCCGAA
TGCTCCGTCTTCGGTCACGCTGCAGCAGGGCGAAGATGA
TAATGGAGACCCGTGCGGTGTGTCGTACTACGTGAAGAT
CTTTGCCGGTGAGTCGGAAACCGATCGTACGCACCGTCG
CAGCACCGTTACGCTCGGCATACGCAAGATCCAGTTCGC
ACCGACCAAGCAGGGCCAGCAGCCGTGCACGCTGGTGCG
CAAGGACTTTATGCTAAGCCCGGGAGAGCTGGAGCTCGA
GGTCACACTAGACAAGCAGCTGTACCTGCACGGGGAGCG
AATAGGCGTCAACATCTGCATCCGCAACAACTCGAACAA
AATGGTCAAGAAGATTAAGGCCATGGTCCAGCAGGGTGT
GGATGTGGTGCTGTTCCAGAATGGTAGCTACCGCAACAC
AGTGGCATCGCTGGAGACTAGCGAGGGTTGCCCAATTCA
GCCCGGCTCCAGTCTGCAGAAGGTAATGTACCTCACGCC
GCTGCTGTCCTCGAACAAGCAGCGACGTGGCATCGCCCT
GGACGGTCAGATCAAGCGTCAGGATCAGTGTTTGGCCTC
GACAACCCTCTTGGCTCAACCGGATCAGCGAGATGCTTT
CGGCGTTATCATATCGTATGCCGTAAAGGTTAAGCTTTT
CCTCGGCGCACTCGGCGGCGAGCTGTCGGCGGAACTTCC
ATTTGTGCTGATGCACCCAAAGCCCGGCACCAAGGCTAA
GGTCATCCATGCCGACAGCCAGGCCGACGTAGAAACTTT
CCGACAGGATACAATCGACCAGCAGGCATCAGTTGACTT cDNA Nucleic Acid Sequence
1964 nucleotides
Mosquito arrestin 1
-continued TGAATAGACGACGCAACGGTTTGGAAATGCTACCTACTA
CCCCAGGCATGGGCTAACACGACGAACGAACTACTACTA
CTAAGCATAAAAAACAGGAAAAAAAATGGAAAACTTAAA
AAATGGATCATACAACCGAACGCAAACGACCTACGACGA
TCGATCTCACTTCCCCGTCTTTTTCATCCTAAGCAATAG
AACGATGGTAGAAAAGGAAGATAAAGATGGAGAGAAAGT
CACGTGTATCAATGACGACGACTACCAAAACTGAAGACG
TAACACATGTTCCCCAGCGAGCGGTAACTGTTCTGTTCT
GACACCTTCCGCTCGACAATGTACCTTTTAAAAACATAC
AAATTAGAAGTCGTCTTCACTACCTTCAACCAATCCAGC
CACTTTGGTATATACTTTTCATAGAATCCTTCTGAGCGC
AAGGACCCTATTGAAATTCAGTGTTATTTTGTAACTGCG
ACCAAATGCCTAGCTGAATGTTGTTGAACGAGTTATGTA
CATCAAAAGATTGAATAAAACAAAAAAAAAAAAAAAAAA
AAAAAAAAAAAAAA

Amino Acid Sequence
383 residues
Mosquito arrestin 1

MVYNFKVFKKCAPNGKVTLYMGKRDFVDHVSGVEPIDGI SEQ ID NO:2
VVLDDEYIRDNRKVFGQIVCSFRYGREEDEVMGLNFQKE
LCLASEQIYPRPEKSDKEQTKLQERLLKKLGSNAIPFTF
NISPNAPSSVTLQQGEDDNGDPCGVSYYVKIFAGESETD
RTHRRSTVTLGIRKIQFAPTKQGQQPCTLVRKDFMLSPG
ELELEVTLDKQLYLHGERIGVNICIRNNSNKMVKKIKAM
VQQGVDVVLFQNGSYRNTVASLETSEGCPIQPGSSLQKV
MYLTPLLSSNKQRRGIALDGQIKRQDQCLASTTLLAQPD
QRDAFGVIISYAVKVKLFLGALGGELSAELPFVLMHPKP
GTKAKVIHADSQADVETFRQDTIDQQASVDFE cDNA Nucleic Acid Sequence
1239 nucleotides
Mosquito odorant receptor 1

ATGAAGCTGAACAAACTGAACCCACGGTGGGATGCGTAC SEQ ID NO:3
GATCGACGGGATTCGTTCTGGTTGCAGTTGCTTTGTTTG
AAATATTTAGGCCTATGGCCACCGGAAGATACGGATCAG
GCAACGCGGAACCGGTACATCGCGTACGGTTGGGCTTTG cDNA Nucleic Acid Sequence
1239 nucleotides
Mosquito odorant receptor 1

CGGATCATGTTTCTACATCTGTACGCTCTAACGCAAGCC

CTATACTTCAAGGATGTGAAGGATATTAATGACATCGCA

AATGCATTGTTCGTGCTTATGACTCAAGTGACGTTGATC

TACAAGCTGGAAAAGTTTAACTACAACATCGCACGGATT

CAGGCTTGTCTGCGCAAGCTTAACTGCACACTGTATCAC

CCGAAACAGCGCGAAGAATTCAGCCCCGTTTTACAATCG

ATGAGTGGAGTGTTTTGGCTGATGATCTTTCTCATGTTT

GTGGCTATCTTCACCATCATCATGTGGGTTATGTCGCCA

GCCTTCGACAATGAACGTCGTCTGCCCGTGCCGGCCTGG

TTCCCGGTGGACTATCACCATTCGGACATAGTGTACGGT

GTACTGTTCCTGTATCAAACCATTGGAATCGTCATGAGC

GCAACGTACAACTTCTCGACCGATACCATGTTTTCCGGC

TTGATGCTACACATAATGGACAAATTGTGCGGCTTGGTA

GTATGGTTAAAAAGCTTGGACATGACGTCCCTCCCGAAC

GCCAATTGGTCGCAACGGATGCGGAATGGAAAGAGATGC

GAAAGCGCATCGACCATCACTCCAAAGTGTACGGTACGA

TGTACGCTAAAGTAACGGAGTGTGTGCTGTTTCACAAGG

ACATCTTAAGGATCTATCTTCGCGCAAGTATGCGCGTCT

GTAATTATCATTTGTATGACACTGCTGCAACTACCGGGG

GCGATGTTACGATGGCCGATCTGCTGGGCTGTGGGGTCT

ATTTGCTAGTAAAGACATCGCAAGTGTTTATTTTCTGTT

ACGTAGGGAATGAAATCTCCTATACGACGGATAATTTAC

AGAGTTTGTTGGGTTTTCCAACTACTTCAAGTTCGATAA

GCGTACCAGCCAAGCAATGATATTTTTCTGCAAATGAC

TCTTAAAGATGTTCACATCAAGGTGGGAAGTGTCTTGAA

GGTTACGCTAAATCTTCACACATTTTTGCAGATTATGAA

GCTATCGTACTCCTATCTGGCCGTACTTCAGAGCATGGA

ATCAGAGTAATGGTGTTAATATCCTTAA

Amino Acid Sequence
394 residues
Mosquito odorant receptor 1

MKKDSFFKMLNKHRWILCLWPPEDTDQATRNRYIAYGWA  SEQ ID NO:4

LRIMFLHLYALTQALYFKDVKDINDIANALFVLMTQVTL

IYKLEKFNYNIARIQACLRKLNCTLYHPKQREEFSPVLQ

SMSGVFWLMIFLMFVAIFTIIMWVMSPAFDNERRLPVPA

WFPVDYHHSDIVYGVLFLYQTIGIVMSATYNFSTDTMFS

GLMLHINGQIVRLGSMVKKLGHDVPPERQLVATDAEWKE

MRKRIDHHSKVYGTMYAKVTECVLFHKDILRIYLRASMR

VCNYHLYDTAATTGGDVTMADLLGCGVYLLVKTSQVFIF

CYVGNEISYTDKFTEFVGFSNYFKFDKRTSQAMIFFLQM

TLKDVHIKVGSVLKVTLNLHTFLQIMKLSYSYLAVLQSM

ESEZ cDNA Nucleic Acid Sequence
1142 nucleotides
Mosquito odorant receptor 2

ATGCTGATCGAAGAGTGTCCGATAATTGGTGTCAATGTG  SEQ ID NO:5

CGAGTGTGGCTGTTCTGGTCGTATCTGCGGCGGCCGCGG

TTGTCCCGCTTTCTGGTCGGCTGCATCCCGGTCGCCGTG

CTGAACGTTTTCCAGTTCCTGAAGCTGTACTCGTCCTGG

GGCGACATGAGCGAGCTCATCATCAACGGATACTTTACC

GTGCTGTACTTTACCTCGTCCTCCGAACCTCCTTTCTCG

TGATCAATCGACGGAAATTTGAGACATTTTTTGAAGGCG

TTGCCGCCGAGTACGCTCTCCTCGAGAAAAATGACGACA

TCCGACCCGTGCTGGAGCGGTACACACGGCGGGGACGCA

GGCTATCGATATCGAATCTGTGGCTCGGCGCCTTCATTA

GTGCCTGCTTTGTGACCTATCCTCTGTTTGTGCCCGGGC

GCGGCCTACCGTACGGCGTCACGATACCGGGCGTGGACG

TGCTGGCCACCCCGACCTACCAGGTCGTGTTTGTGCTGC

AGGTTTACCTTACCTTCCCCGCCTGCTGCATGTACATCC

CGTTCACCAGCTTCTACGCGACCTGCACGCTGTTTGCGC

TCGTCCAGATAGCGGCCCTAAAGCAACGGCTCGGACGCT

TGGGGCGCCACAGCGGCACGATGGCTTCGACCGGACACA

GCGCCGGCACACTGTTCGCCGAGCTGAAGGAGTGTCTAA

AGTATCACAAACAAATCATCCAATATGTTCATGATCTCA

ACTCACTCGTCACCCATCTGTGTCTGCTGGAGTTCCTGT

CGTTCGGGATGATGCTGTGCGCACTGCTGTTTCTGCTAA

GCATTAGCAATCAGCTGGCACAGATGATAATGATTGGAT

CGTACATCTTCATGATACTCTCGCAGATGTTTGCCTTCT

ATTGGCATGCGAACGAGGTACTGGAGCAGAGCCTAGGCA

TTGGCGATGCCATTTACAATGGAGCGTGGCCGGACTTTG

AGGAACCGATAAGGAAACGGTTGATTCTAATTATTGCAC

GTGCTCAGCGACCGATGGTGGTAAGATTAAAGTCGGCAA cDNA Nucleic Acid Sequence
1142 nucleotides
Mosquito odorant receptor 2

CGTGTACCCGATGACGTTGGAAATGTTTCAAAAATTGCT

CAACGTGTCCTACTCCTATTTCACACTGCTGCGCCGAGT

GTACAACTAA

Amino Acid Sequence
380 residues
Mosquito odorant receptor 2

MLIEECPIIGVNVRVWLFWSYLRRPRLSRFLVGCIPVAV   SEQ ID NO:6
LNVFQFLKLYSSWGDMSELIINGYFTVLYFNLVLRTSFL
VINRRKFETFFEGVAAEYALLEKNDDIRPVLERYTRRGR
MLSISNLWLGAFISACFVTYPLFVPGRGLPYGVTIPGVD
VLATPTYQVVFVLQVYLTFPACCMYIPFTSFYATCTLFA
LVQIAALKQRLGRLGRHSGTMASTGHSAGTLFAELKECL
KYHKQIIQYVHDLNSLVTHLCLLEFLSFGMMLCALLFLL
SISNQLAQMIMIGSYIFMILSQMFAFYWHANEVLEASLG
IGDAIYNGAWPDFEEPIRKRLILIIARAQPTDGGKIKVG
NVYPMTLEMFQKLLNVSYSYFTLLRRVYN cDNA Nucleic Acid Sequence
1236 nucleotides
Mosquito odorant receptor 3

ATGCCTTCTGAGCGGCTTCGTCTCATTACTTCCTTCGGA   SEQ ID NO:7
ACTCCTCAAGACAAACGCACGATGGTACTGCCAAAATTA
AAGGATGAAACAGCAGTGATGCCGTTTCTGCTGCAAATT
CAAACCATTGCCGGACTGTGGGGTGACCGTTCCCAGCGG
TACCGTTTTTATCTCATCTTTTCCTACTTCTGCGCGATG
GTGGTTCTACCCAAAGTGCTGTTCGGTTATCCAGATCTC
GAGGTTGCGGTACGCGGCACGGCCGAGCTGATGTTCGAA
TCGAACGCATTCTTCGGCATGCTAATGTTTTCCTTTCAA
CGCGACAACTACGAGCGATTGGTGCATCAGCTGCAGGAT
CTGGCAGCTCTAGTCCTCCAAGACCTACCCACAGAGCTG
GGAGAGTACCTGATCTCAGTGAACCGACGGGTCGATCGG
TTCTCCAAAATTTACTGCTGCTGTCACTTTTCCATGGCA
ACGTTCTTTTGGTTCATGCCCGTCTGGACGACCTATTCC
GCCTACTTTGCTGTGCGCAACAGCACGGAACCGGTCGAG
CACGTGTTGCACCTCGAGGAAGAGCTGTACTTCCTGAAC
ATTCGGACTTCGATGGCGCACTATACGTTTTATGTGGCC cDNA Nucleic Acid Sequence
1236 nucleotides
Mosquito odorant receptor 3

ATTATGTGGCCCACGATCTATACGCTCGGGTTTACCGGT
GGCACAAAGCTGCTGACCATTTTCAGCAATGTTAAGTAC
TGTTCGGCCATGCTGAAGCTCGTTGCACTCCGAATCCAC
TGTCTAGCGAGAGTAGCGCAAGACCGAGCGGAAAAGGAG
CTGAACGAGATTATTTCCATGCATCAGCGGGTACTCAAC
TGCGTGTTCCTGCTGGAGACGACATTCCGCTGGGTATTT
TTCGTGCAGTTCATTCAGTGTACAATGATCTGGTGCAGT
CTCATCCTCTACATAGCGGTGACGGGGTTCAGCTCGACG
GTAGCGAATGTATGTGTCCAGATCATTTTGGTGACGGTG
GAAACTTACGGCTACGGCTACTTCGGAACAGATCTAACC
ACGGAGGTGCTTTGGAGCTATGGCGTTGCCCTCGCCATT
TACGATAGCGAGTGGTACAAGTTTTCCATTTCGATGCGC
CGCAAACTTCGACTGCTACTGCAACGATCCCAAAAACCG
CTCGGCGTAACGGCGGGAAAGTTTCGCTTCGTCAATGTG
GCCCAGTTTGGCAAGATGCTCAAGATGTCCTATTCATTT
TACGTAGTACTGAAGGAGCAGTTTTAG

Amino Acid Sequence
411 residues
Mosquito odorant receptor 3

MPSERLRLITSFGTPQDKRTMVLPKLKDETAVMPFLLQI   SEQ ID NO:8
QTIAGLWGDRSQRYRFYLIFSYFCAMVVLPKVLFGYPDL
EVAVRGTAELMFESNAFFGMLMFSFQRDNYERLVHQLQD
LAALVLQDLPTELGEYLISVNRRVDRFSKIYCCCHFSMA
TFFWFMPVWTTYSAYFAVRNSTEPVEHVLHLEEELYFLN
IRTSMAHYTFYVAIMWPTIYTLGFTGGTKLLTIFSNVKY
CSAMLKLVALRIHCLARVAQDRAEKELNEIISMHQRVLN
CVFLLETTFRWVFFVQFIQCTMIWCSLILYIAVTGFSST
VANVCVQIILVTVETYGYGYFGTDLTTEVLWSYGVALAI
YDSEWYKFSISMRRKLRLLLQRSQKPLGVTAGKFRFVNV
AQFGKMLKMSYSFYVVLKEQF

Genomic Nucleic Acid Sequence
3895 nucleotides
Mosquito odorant receptor 1

AGCTTTGTTCATTTATGTTGAAATCTAGCCCATTTTGTA   SEQ ID NO:9
TAGTGCTGAACGACGAAGAACATACGAAAGTACCTCGTC

-continued

| Genomic Nucleic Acid Sequence |
| :---: |
| 3895 nucleotides |
| Mosquito odorant receptor 1 |

CGAACACTATCAACATTAATTATACCAAGCTAGAAGAAG

ATATTTATAGTCAAGCCTCAACATCATAGGAAACTTTAG

CAAAACCATTTAATTTACATGATGATAAGTCCCACCTCT

TACCCCAGCACAGGTTTGAGAAGGACGAAAGTATCTTTA

CGATAATATTACTCTAAGGTAGTTTTTGAATAAAATAAA

AATTTACGTGCAAGTGGTGGCATCGGACATCATTCGAAA

GAATCTACTAAGTCATACACACACCCAAGACGACCGACG

TAGTTTCATCTAGAAAAAACGGGTCAGCTCCATCGAACA

CGTCAGGACATAACTGCGACATGCGTATGGTCAGTTCCA

CTAGTGCCAACACTGGTTCCAGGGCACTACCTTCCGAAG

CAGTAGAACCTAATGTATTGGAAATTATTAGGACATACT

GCAACATGCATATGGCTAGTTCCGCTGGTACCAACGATG

GCACCAGGACACTATCTGCGGCCTTGTAAAATCACTGTA

AAAATCTATACAAAAACGGCTTTACCCATACTTTATCAC

AAAACGGCAGGTGAGGGCTGGATTGCTTCAAAGCATTAG

AAATATATAATTTCAAAGTCCATAATCTCCTTAAAAGAT

AGACAaCAGTAGAGAACACATTTAGTGCTCTTTTCGTTC

GAGTTAGTTGCCTTCTCAAGTAAGCGTTTAATGCTCAAT

TGTTGTAGATTCGTTGGATGACTCTCGCTACGTGCTATA

GTGGTCAATACTTCCAATTAGATTTCATAATTAGTTTCC

AATTGTCCACGGAAAACCCaCAAAAGAAAAAAAAACTTG

TATCTAGGGTGGAATTTTTCGAGAACAATTGGACACTTC

ATATGAAAAAGGACAGCTTTTTCAAAATGTTAAATAAAC

ACCGTTGGATCCTTTgttggatttcaattctccaaattc tgcagaataattctgcaaattttacaaaactgctcaacc accaataattccaattaatcatctgaacatttaaaactg ataattaagatgagtaattgcttcgtcatcacctaagaa atcgattagtttggataaaaagaacaaattgaaatacaa taaagtccctgaatttattcgaataacggcttgaactc atttatttcaaaacctttgagaaattcctcgttgaaaa ttggtctcctatagttctgctaacgggccacttcaaaag caagaactaacaaaatcataattatggtgcaagtaacta tcagtaccagtaatcgccattaaaaacttttcctcaatt tgcggctcgttaccggctaaatacagagcagagtaacgg gaagtgatcaacgtcgctattagtataacgaggaacgcc ctccgaaggtgtgttgaaggaccttttcaaattgaaacc aagtactgtttccagttttaaattggatagttataaaat -continued

| Genomic Nucleic Acid Sequence |
| :---: |
| 3895 nucleotides |
| Mosquito odorant receptor 1 | gagccgttcaacgatcgggcatcatttgagtttcatctt cgaggagaaatagatcagtgccactgtttaaccgaaagt aatgaagctgaacaaactgaacccacggtgggatgcgta cgatcgacgggattcgttctggttgcagttgctttgttt gaaatatttagGCCTATGGCCACCGGAAGATACGGATCA

GGCAACGCGGAACCGGTACATCGCGTACGGTTGGGCTTT

GCGGATCATGTTTCTACATCTGTACGCTCTAACGCAAGC

CCTATACTTCAAGgATGTGAAGGATATTAATgtgagtct ctagttagctattagtgttccacctgtccataatctgtc ttttattgggtagGACATCGCAAATGCATTGTTCGTGCT

TATGACTCAAGTGACGTTGATCTACAAGCTGGAAAAGTT

TAACTACAACATCGCACGGATTCAGGCTTGTCTGCGCAA

GCTTAACTGCACACTGTATCACCCGAAACAGCGCGAAGA

ATTCAGgtaagcctgctgggaaatatgactaaaaagagt gctaacaaacgactctcctccaaatgtagCCCCGTTTTA

CAATCGATGAGTGGAGTGTTTTGGCTGATGATCTTTCTC

ATGTTTGTGGCTATCTTCACCATCATCATGTGGGTTATG

TCGCCAGCCTTCGACAATGAACGTCGTCTGCCcGTGCCG

GCCTGGTTCCCGGTGGACTATCACCATTCGGACATAGTG

TACGGTGTACTGTTCCTGTATCAAACCATTGGAATCGTC

ATGAGCGCAACGTACAACTTCTCGACCGATACCATGTTT

TCCGGCTTGATGCTACACATAAATGGACAAATTGTGCGG

CTTGGTAGTATGGTTAAAAAGgtgagttacggcgactac ttgcctccagtaaggacagggagtttgtttccgttatga tatcattttatcagCTTGGACATGACGTCCCTCCCGAAC

GCCAATTGGTCGCAACGGATGCGGAATGGAAAGAGATGC

GAAAGCGCATCGACCATCACTCCAAAGTGTACGGTACGA

TGTACGCTAAAGTAACGGAGTGTGTGCTGTTTCACAAGG

ACATCTTAAGgtacgaattgggccaattaattgtgtcat ttaaaaagcttgacccaacttttcacagcttcggcgatg aagtgcaggacattttccaagGATCTATCTTCGCGCAAG

TATGCGCGTCTGTAATTATCATTTGTATGACACTGCTGC

AAcTACCGGGGcGATGTTACGATgGCCGATCTGCTGGG

CTGTGGGTCTATTTGCTAGTAAaGACATCGCAAGTGTT

TATTTTCTGTTACGTAGGGAATGAAATCTCCTATACGgt aggttggacacgtagaggaattaaatgtttgggaagaat atcaataccaaatagtatgatgtttcgttacagACGGAT

AAATTTACAGAGTTTGTTGGGTTTTCCAACTACTTCAAG

-continued

| Genomic Nucleic Acid Sequence |
| --- |
| 3895 nucleotides |
| Mosquito odorant receptor 1 |

TTCGATAAGCGTACCAGCCAAGCAATGATATTTTTTCTG

CAAATgtgagatagcggtgtatttgtgcagtcagtacat taaatacgttctctatttcagGACTCTTAAAGATGTTCA

CATCAAGGTGGGAAGTGTCTTGAAGGTTACGCTAAATCT

TCACACATTTTTGCAGgtatgtaattatgctgtggtatt tagcttgaaataagctacaaactttgaaagtaatttcaa tctgttttgtagATTATGAAGCTATCGTACTCCTATCTG GCCGTACTTCAGAGCATGGAATCAGAGTAATGGtGtTAA TATCCtTAATGTTGAAATTATATTTTGTTAGATTTATTG CATAAAGTAaTaTTTAATTTTATACATCAAACGTAAGCC CGCtaGTTTTCAATTAGCCTTTTCCAAAATTTATCAAAT

TGATTTCGAATTGATTGCAGAGTTTCAGGAATTTAATCT

GATAGGATATCTTGTTTATCCAATAGAGGTGTGGAAGCG

TTCCCAAGCCATTCGTTTGATAGTTTATAGCACCGTCGA

GCAGTTGATCGCTGTGATCGCTAGGCGCACCTGATTTTA

TCTTTATCTCGCACCTGTTATGGCAAGGGCGCTTTTCAC

ACGTTTCACACAATATAATGCACATGTATAATGCATTCT

TACTTTAGCATTTTTGTTACATATAATACCAAAATTATG

CATTTTTATTCTCACGCAACGATTAGAGGATGACTTcAC

AAAGGTCCATCTAGTGGTAGGAGGTATACAATTATACCT

CTCAAAATCTCACAGCAtAATGAGAAACAAAAGGATACC

AAGCATACCCTTTTTTTACTTGACAATTTCATTTGATTT

ATGTAATAAAGCACTGCaCGTCGACTTCCTAAAA

| Genomic Nucleic Acid Sequence |
| --- |
| 4985 nucleotides |
| Mosquito odorant receptor 2 |

GGGATCCTCTAGAGTCGACCTGCAGGCATGCAAGCTT  SEQ ID NO:10

CCCTCACCGTGACGTGCTAGAAATGGTTCAACATACT

CGTCCGGCAGAGCGAAGACGACGAACAGCGGAATGTC

CCAGGAAATGTAATGAGATATCACAGCAAGTGAACCC

AAACCGAGCTGTGCGCTTTGTGTTGCGCTTTAAAAAT

GGCCCTTCCTTCGCCGCATCTGCTTGGTTTCACACGC

TTTCCCAGGAAATCCACTGACCACTGGCCACACATCA

ACCACCGGAGCGGGAGCCTCAGTGCCCAGCGAAGCAT

ATAATTTGCTCAAAAAGTCACGGTACTCAATTAATTT

GATTATAATCAATTTCGTGGCTTCCAACACACCCTTC

| Genomic Nucleic Acid Sequence |
| --- |
| 4985 nucleotides |
| Mosquito odorant receptor 2 |

TTCCACAATCCATCGCCGAGTGAGCGAGTATAAAGGT

GAAGAAACGTACCTTGCGCTTGCTCACTAACTGAACC

GGATTTCAAAAAGGAACATAAACCGCAACCCACAGCC

GAAAATGCTGATCGAAGAGTGTCCGATAATTGGTGTC

AATGTGCGAGTGTGGCTGTTCTGGTCGTATCTGCGGC

GGCCGCGGTTGTCCCGCTTTCTGGTCGGCTGCATCCC

GGTCGCCGTGCTGAACGTTTTCCAGTTCCTGAAGCTG

TACTCGTCCTGGGGCGACATGAGCGAGCTCATCATCA

ACGGATACTTTACCGTGCTGTACTTTAACCTCGTCGt acgtgggcgaggggagggcaataaccttcccacttg gtggatattttcataccttttccatgtgttttttttat tctctgtttgttgccatccagCTCCGAACCTCCTTTC

TCGTGATCAATCGACGGAAATTTGAGACATTTTTTGA

AGGCGTTGCCGCCGAGTACGCTCTCCTCGAGgtaagt cattggttttctagttttttgggggagttgtttacac cataaccaccccgacggtaacatttgatcgtcccgc gaaaatgtttgtacagAAAAATGACGACATCCGACCC

GTGCTGGAGCGGTACACACGGCGGGGACGCATGCTAT

CGATATCGAATCTGTGGCTCGGCGCCTTCATTAGTGC

CTGCTTTGTGACCTATCCTCTGTTTGTGCCCGGGCGC

GGCCTACCGTACGGCGTCACGATACCGGGCGTGGACG

TGCTGGCCACCCCGACCTACCAGGTCGTGTTTGTGCT

GCAGGTTTACCTTACCTTCCCCGCCTGCTGCATGTAC

ATCCCGTTCACCAGCTTCTACGCGACCTGCACGCTGT

TTGCGCTCGTCCAGATAGCGGCCCTAAAGCAACGGCT

CGGACGCTTGGGGCGCCACAGCGGCACGATGGCTTCG

ACCGGACACAGCGCCGGCACACTGTTCGCCGAGCTGA

AGGAGTGTCTAAAGTATCACAAACAAATCATCCAGta agtagacgctagtagactcgaccggattgcccttccc tcggggaggggaggtttgctatttcgggatgcggcag cacgcatacacacaaaccggaagccattaattctccc gttttcatgcccgcacgggcactgggtcatgtttcac atccttccttccttccaaacacacacacgcgcgcgt gcacgtacagATATGTTCATGATCTCAACTCACTCGT

CACCCATCTGTGTCTGCTGGAGTTCCTGTCGTTCGGG

ATGATGCTGTGCGCACTGCTGTTTCTGCTAAGCATTG taagtaaaatcgaccgacgtgcggtcgctagtccgtc

-continued

| Genomic Nucleic Acid Sequence |
| --- |
| 4985 nucleotides |
| Mosquito odorant receptor 2 | tccggactctcatttcgggactcaatcgttccatctc tcaatagAGCAATCAGCTGGCACAGATGATAATGATT

GGATCGTACATCTTCATGATACTCTCGCAGATGTTTG

CCTTCTATTGGCATGCGAACGAGGTACTGGAGCAGGt aatggcgctgaagctgagtttggttgagcggttcgct atagatcggctgtcttacattgttgtgtttctgcatg gggatcggttttgttttcctctccatttcagAGCCT

AGGCATTGGCGATGCCATTTACAATGGAGCGTGGCCG

GACTTTGAGGAACCGATAAGGAAACGGTTGATTCTAA

TTATTGCACGTGCTCAGCGACCGATGTGGTAAGttt ggctgatcgatgctctgttcaatgaacatggcacaga aggctgtgtaaatagctgttcattaataagttttttc agaatgtatcgttttttagttgatttaaacgcattgtt ctatgcaatggtagcaacaatagaccgcctttattaa tccaagcttcctttaggattgattttttattttaagag aaagataaaccattttttagtaaccaatttagttacag gaaccaaaatacagaatttattattattattattatt attattattattattattattattattattattatta ttattattattattattattattattataattat tattattattattattattattattattattattatt aatattattattattattattattactattatta ttataattattacttttattattattattattat tattattattattattattattattattattattatt attataattatgattattattattattattatta ttattattattataacaataataattattattattat ttattattaattaattaatttattattattaattatt attattgttattcattattatacattattatcataat aataatttatttatgattattattattattattatta ttattattattattattattattcttattattat tattattattattattaatattatttttaatatt attattattattactattcttattataattatttt ttttttattattattattattattattattatta ttattattattattgctattgttattattattct tattattgctattgttattattattattcttattatt gttgttgttgttgttcttattattgttgttgttgtta ttcttattattgtttattattattgtttttttttatt ctctaattattccagtaatccataataaaaaataata aagtaaataaatagtaaatagtaaataattccagtaa ctgtagtaatacacaataatctctaagaattaaaatt gcattttgtaatgaaatatgttgattgttcgaatagt tcagaaaaacttaaaaatgcctcagcattaaacagtt ttgaggttgttcagggcatttagtttagatattttag tatttttaaagcatttgttttcattactacaaaaaagc aaatttatgagtgaattactttcagttcttctaaacg cctatgtgtatgcaattacataacaatagctctcttt tttattgcatttttccttagtaatctaaatccaatct cttctttccctcttgcagATTAAAGTCGGCAACGTGT

ACCCGATGACGTTGGAAATGTTTCAAAAATTGCTCAA

CGTGTCCTACTCCTATTTCACACTGCTGCGCCGAGTG

TACAACTAAACTTAACCGGTAAACAAACAAAAATCCC

CTCATCACTATGCAAAGACAGCAAGCAGCCGATCATC

AAACACCATTAGCAGCCACAAAGTTACCAGCCGCTTA

TCCCACGGGATTTGGTGGAAAGTTATTGCACTGAAGC

TCTTTCACCCAAATTTTCATGGAGGTTCCCTCTCAAC

CAACCCATTGAAGCGAATAAAAGTATCAGCAACCAGG

CGACGGTGAAAAAACGCTGCATTATTGTGCTTGCTTC

AGCATTCCAGCGAATGACTCTTAAACTTTTCCATTCA

AAAGTCGCGATGCTCACGATACGGAGCGGTGTGTTGT

TCGATCCGCCGAGTGCACTCGCAAGCCGGTGATGTTG

CCGGTGGAAATGCACAGATCGACACAGCGATAGATAA

TCGTTTGTTCGCGTAAATGGGAGGGAAAAAAGTAAGC

TGCCAGCTACTTCATTTCCATGTTAATTGAAACTCAA

GCCAACGAACATGCAGAACCCGGTTGGTTGTGTGTCT

CCGCTCCGGGAAAGGTCTCTGCTCCGGGCATGGATT

CTTTCCCCCTCCGGGTGGTTGGGGTATTGTTTAGGT

TTTTATTTTACAAATTCATATCCTTCCGCTTCCGCAT

CAGCCGACCCGGTGGGTGCGCCAGACAGATGTGCGGC

GGGCAACAAAACTATGCACGAACATGGCCAACAAACA

CAGCTTCTATCTCATCTCTGTGTCGCACTGTCTCGCT

TTCCCGCTGCGTTGCTTGTAGTACTATCATTGTTTTA

GTCCACGGGTTTACTTCTAATTCCATTGCACCACGCA

AAAAGGCTCATCCTTTGCTCGTTCCGGTTGCAACTTC

GACAAGCGCATGGTTGGGATACGAACAAAAAACCAAC

TACTCCACCCACTACTACTACTACTGCCACCACCACT

AACAACACTACACTTGGTTGGGAGCTTGCAGACCCAC

-continued

| Genomic Nucleic Acid Sequence |
| :---: |
| 4985 nucleotides |
| Mosquito odorant receptor 2 |

AAGCAAACAACGATACAAGCTAGCTAGCTGCTGTGTG

CGCTCGAGTCAGCCGACGGTACAAGGTTTAACCGGTA

CAAGCAACTCCCGGACCGATCCCAAAACTCTGACAAG

GCACGGGCCGCATCCGGCAGTACGGTCGGAAAACAT

GGAAAATGTTTAATTAAAACTGTAATTGTCAATCGCT

GCTACAAGTTGTGACACAGGGAGAGAGAGAGACAGAG

CGCGCCCGATGGTGATGGTGTAAAAGATAGATACAGG

AAAAGAGCGAGAAACATTGGTACGATTTGGTGTGGTT

AGCAAATTTGATTTCCACTGATTTTGAGTGCAAATTT

AATGCATCGAAAATTTGCCATTCAGGGTAAAGTTGCT

CGTGGACGGATCCCCCGGGCTGCAGGAATTCGATATC

AAGCTTATCGATACCGTCGACCTCGAGGGGGGGCCCG

GTACCCAGCTTTTGTTCCCTTTAGTGGA

| Genomic Nucleic Acid Sequence |
| :---: |
| 2083 nucleotides |
| Mosquito odorant receptor 3 |

AAGCAGAACACATCAAGAAGCAATTAGGTGTGTCGTA SEQ ID NO:11

CGTTAGCAAGTAGTTCGCGAGGAGGAATAAAATAGAT

GCCTTCTGAGCGGCTTCGTCTCATTACTTCCTTCGGA

ACTCCTCAAGACAAACGCACGATGGTACTGCCAAAAT

TAAAGGATGAAACAGCAGTGATGCCGTTTCTGCTGCA

AATTCAAACCATTGCCGGACTGTGGGTGACCGTTCC

CAGCGGTACCGTTTTTATCTCATCTTTTCCTACTTCT

GCGCGATGGTGGTTCTACCCAAAGTGCTGTTCGGTTA

TCCAGATCTCGAGGTTGCGGTACGCGGCACGGCCGAG

CTGATGTTCGAATCGAACGCATTCTTCGGCATGCTAA

TGTTTTCCTTTCAACGCGACAACTACGAGCGATTGGT

GCATCAGCTGCAGGATCTGGCAGCTCTAGgtgagtat gcagccaatcgattgttccaaaccttcgcaacatcct tcgtaacactgctacactttcagTCCTCCAAGACCTA

CCCACAGAGCTGGGAGAGTACCTGATCTCAGTGAACC

GACGGGTCGATCGGTTCTCCAAAATTTACTGCTGCTG

TCACTTTTCCATGGCAACGTTCTTTTGGTTCATGCCC

GTCTGGACGACCTATTCCGCCTACTTTGCTGTGCGCA

ACAGCACGGAACCGGTCGAGCACGTGTTGCACCTCGA

GGAAGAGCTGTACTTCCTGAACATTCGGACTTCGATG

-continued

| Genomic Nucleic Acid Sequence |
| :---: |
| 2083 nucleotides |
| Mosquito odorant receptor 3 |

GCGCACTATACGTTTTATGTGGCCATTATGTGGCCCA

CGATCTATACGCTCGGGTTTACCGGTGGCACAAAGCT

GCTGACCATTTTCAGCAATGTTAAGTACTGTTCGGCC

ATGCTGAAGCTCGTTGCACTCCGAATCCACTGTCTAG

CGAGAGTAGCGCAAGACCGAGCGGAAAAGGAGCTGAA

CGAGATTATTTCCATGCATCAGCGGGTACTCAAgtaa gtaaattcaaattgaaagttttgcagggaataacttg agtgtgtctgacccgtgcacatcctagCTGCGTGTTC

CTGCTGGAGACGACATTCCGCTGGGTATTTTCGTGC

AGTTCATTCAGTGTACAATGATCTGGTGCAGTCTCAT

CCTCTACATAGCGGTGACGgtaatagcattttcgtca tttcgttagccttattcaatccatttttgtgaacgtg aatttcccccagGGGTTCAGCTCGACGGTAGCGAATG

TATGTGTCCAGATCATTTTGGTGACGGTGGAAACTTA

CGGCTACGGCTACTTCGGAACAGATCTAACCACGGAG

GTGCTTTGGtacccttttggatgaagcttcaaaaagt aattccaaattctgttttcgattttttccccttttcca ctagAGCTATGGCGTTGCCCTCGCCATTTACGATAGC

GAGTGGTACAAGTTTTCCATTTCGATGCGCCGCAAAC

TTCGACTGCTACTGCAACGATCCCAAAAACCGCTCGG

CGTAACGGCGGGAAAGTTTCGCTTCGTCAATGTGGCC

CAGTTTGGCAAGgtaacattaattacagttttgaaaat tctgaagaatgcatcttacttgccttacttgttgttc cagATGCTCAAGATGTCCTATTCATTTTACGTAGTAC

TGAAGGAGCAGTTTTAGGAGCTGCTGTTTCCCACCCT

GGAAATGGCCTTTTCGCACTGTCTTCTGTTTGTTGGA

CGCACGCAGCACCGAGAGCGCCCCTGCACGCACTGAC

GTATTTTGGCTACTTTGACGTTTGCACCTTTGACAGC

TGAAGGACAGGGTACAATTTTTGCTGCTGTTATTACG

CGCAGCGCATTGGATACGAAAACATTGGCCACAAGTT

CTACGATTTTAGCGTTTATTTACTGTTCGTAGCAGCT

TTTTTCCaCAATAAACACACACAATAACGTACCGACA

GTATTCTTTTCATTGTAGGATAGAGAAGCCGCCGGCC

AGCAGCCAAAACGCGCCGCAAAACGAAAGGCGGCACC

ACCGGGGAAAAACACGGGAGCAAAACGAGAACAGAA

CGCAGTAAACAACAAAACCGGCCGGAACAACAACGGT

GCCGGAAACGA

| Genomic Nucleic Acid Sequence |
| 2374 nucleotides |
| Mosquito odorant receptor 4 |
|---|
| GGGGAACTCCCCCACCCGACCAGACGACGGAAAGCTA SEQ ID NO:12 |
| ACGATGTGCAATTGAATAGTCATTAGTAGCGTTTTTG |
| CTCGCAAACGAACTAACCCTTTGACTTTTTAAGTTCA |
| CTACGGTGAGGACAAAAATCAATAAATTAAATCGAGA |
| CCGTTGATGAGCAAAAGAAAAAAAAAATATTTTACTGA |
| TTTTCATTTCGTTCCATCGACTACATAATCATAATTA |
| TATGCCACATTTTATTATAAGTTTTTGTATCATTTTT |
| AAACAACACAAAAATGCATCCTTTCGAATATTAGTCA |
| GGTTGTATCAACAATGAAGTTTGAACTGTTTCAAAAA |
| TATTCCTCCCCGGACACGGTCTTATCCTTCGTGCTAA |
| GGCTTTTGCATATCGTGGGCATGAATGGGGCAGGATT |
| TCGGTCGCGAATTCGAGTTGGTGGCATTTTTCTGTTC |
| TATTTAATCTTTCTTGTAATACCGCCACTAACGGGCG |
| GGTACACCGATGGTCACCAGCGTGTACGCACCAGTGT |
| GGAATTCCTGTTTAATTGCAATATTTACGGCGGCAGT |
| ATGTTCTTTGCCTACGATGTGGCCACTTTCCAAGCGT |
| TCATCCAGGAACTGAAGAGCCTTTCGGTTTTGGtaa |
| tatttaattaattaaaattgcgtttattgcatcatca |
| tttgtttctctttgcagTATGCTCACATTCGTACAGA |
| CTAAAGTATAAGCTGACCCGGTTCAACCGTCGAGCGG |
| ATATTATCGCCAAAGTGCAAACGACCTGCATGGGTGC |
| TGTAACGCTTTTCTACTGGATTGCACCGATACCTTCC |
| ATCTGTGCGCACTACTACAGGTCGACCAATTCCACCG |
| AACCCGTGCGGTTTGTGCAACATTTAGAGGTGAAGTT |
| CTATTGGCTCGAGAATCGCACCTCAGTCGAGGACTAC |
| ATAACCTTCGTGCTGATCATGCTACCCGTCGTGGTTA |
| TGTGTGGTTACGTATGCAATTTGAAGGTGATGACCAT |
| CTGCTGCAGCATTGGACACTGTACACTGTACACCAGG |
| ATGACTATAGAGATGGTAGAGCAGTTGGAAAGCATGG |
| CATCAGCGGAACGAACTGCCAGCGCCATACGCAACGT |
| GGGGCAGATGCACAGTGGTTTACTGAAATGCATTAGG |
| CTTTTGAACACGTCAATCCGATCGATGCTGATGCTGC |
| AGTGGTTGACCTGCGTGTTAAACTGGAGCATTTCTCT |
| CATCTATCTAACGAACGTGgttagttttgtcttgttt |
| ggaaatccaaaaacaaaaagatggctataattgaact |
| ttctattacagGGCATCTCGCTACAATCGGTTACCGT |
| GGTGGTAATGTTTTTCTTGCCACTGCGGAAACTTTC |
| CTGTATTGTTTACTTGGGACGCGGCTTGCGACACAAC |

| Genomic Nucleic Acid Sequence |
| 2374 nucleotides |
| Mosquito odorant receptor 4 |
|---|
| AGCAGCTGCTGGAGCACGCACTCTATGCTACACGGTG |
| GTACAACTACCCAATAGCCTTTCGCAGCAGCATTAGG |
| ATGATGTTGAGACAGTCGCAAAGGCATGCACACATAA |
| CGGTGGGGAAGTTTTTTCGCGTTAATTTGGAAGAATT |
| TAGCAGGATTGTCAACTTATCCTACTCTGCTTACGTC |
| GTACTTAAGGATGTAATAAAGATGGATGTACAGTGAA |
| TGTTTTTTTTTTGGCTTGGCAACGAATGAAGTTTTC |
| CGAATCTATATTAGATCTAGAATTTAATCTAGATGTC |
| ATAATATGATCTTGGCCATGACCGGTTCCTGGTTTTG |
| GAACCAATTCTCAAAACAATTTTGAACTTAGGGCGAG |
| GCATGAAATGTCCCAAGAACCTATCCAAGTTCTGGAA |
| CTACATATTACCGAATCTATCCCATTATTGCCTCGGA |
| ACTGGTTTGGTGCTAAATATTTGTCCAAATGTTGGTC |
| CTGGACCTATCCAGACAAAGATCTTCAATTATTCCTA |
| CCACTGGAACTGATTAATTGATGTAGGAAGTCATGGA |
| GGTGTTCAGGGAGAATTTAAACACTAATGTTCCAACT |
| CATTATTTCAAGGGCAATTCTATTTTTTATATGCCCC |
| TACGGATTGATACGTATGTATTACTCCATTTCCTGGA |
| CTTTGTCTTATTCTTGCTGCTGATTGGACGTGAAATG |
| TTGAGAAAAAGATTCTTATTTATGAGTGATACAGAGC |
| CTTTAAATACTCCTACGTTGTTTGCTATTTAAGTATG |
| GCCAGGCTAATCACAATCGCTACTAATGAACAGAATC |
| TCTTCTAATTAAACCCTTTCGATTGATAGTGTCAATG |
| TCAATGTCGAGATAATTGAACTGCAAACgATACCTAC |
| CTTAAACGGAGCAGAACACATCAAGAAGCAATTAGGT |
| GTGTCGTACGTTAGCAAGTAGTTCGCGAGGAGGAATA |
| AAATAG |

| cDNA Nucleic Acid Sequence |
| 1194 nucleotides |
| Mosquito odorant receptor 4 |
|---|
| ATGAAGTTTGAACTGTTTCAAAAATATTCCTCCCCGG SEQ ID NO:13 |
| ACACGGTCTTATCCTTCGTGCTAAGGCTTTTGCATAT |
| CGTGGGCATGAATGGGGCAGGATTTCGGTCGCGAATT |
| CGAGTTGGTGGCATTTTTCTGTTCTATTTAATCTTTC |
| TTGTAATACCGCCACTAACGGGCGGGTACACCGATGG |
| TCACCAGCGTGTACGCACCAGTGTGGAATTCCTGTTT | cDNA Nucleic Acid Sequence
1194 nucleotides
Mosquito odorant receptor 4

```
AATTGCAATATTTACGGCGGCAGTATGTTCTTTGCCT
ACGATGTGGCCACTTTCCAAGCGTTCATCCAGGAACT
GAAGAGCCTTTCGGTTTTGGTATGCTCACATTCGTAC
AGACTAAAGTATAAGCTGACCCGGTTCAACCGTCGAG
CGGATATTATCGCCAAAGTGCAAACGACCTGCATGGG
TGCTGTAACGCTTTTCTACTGGATTGCACCGATACCT
TCCATCTGTGCGCACTACTACAGGTCGACCAATTCCA
CCGAACCCGTGCGGTTTGTGCAACATTTAGAGGTGAA
GTTCTATTGGCTCGAGAATCGCACCTCAGTCGAGGAC
TACATAACCTTCGTGCTGATCATGCTACCCGTCGTGG
TTATGTGTGGTTACGTATGCAATTTGAAGGTGATGAC
CATCTGCTGCAGCATTGGACACTGTACACTGTACACC
AGGATGACTATAGAGATGGTAGAGCAGTTGGAAAGCA
TGGCATCAGCGGAACGAACTGCCAGCGCCATACGCAA
CGTGGGGCAGATGCACAGTGGTTTACTGAAATGCATT
AGGCTTTTGAACACGTCAATCCGATCGATGCTGATGC
TGCAGTGGTTGACCTGCGTGTTAAACTGGAGCATTTC
TCTCATCTATCTAACGAACGTGGGCATCTCGCTACAA
TCGGTTACCGTGGTGGTAATGTTTTTTCTTGCCACTG
CGGAAACTTTCCTGTATTGTTTACTTGGGACGCGGCT
TGCGACACAACAGCAGCTGCTGGAGCACGCACTCTAT
GCTACACGGTGGTACAACTACCCAATAGCCTTTCGCA
GCAGCATTAGGATGATGTTGAGACAGTCGCAAAGGCA
TGCACACATAACGGTGGGGAAGTTTTTTCGCGTTAAT
TTGGAAGAATTTAGCAGGATTGTCAACTTATCCTACT
CTGCTTACGTCGTACTTAAGGATGTAATAAAGATGGA
TGTACAGTGA
```

Amino Acid Sequence
412 residues
Mosquito odorant receptor 4

```
MKFELFQKYSSPDTVLSFVLRLLHIVGMNGAGFRSRI    SEQ ID NO:14
RVGGIFLFYLIFLVIPPLTGGYTDGHQRVRTSVEFLF
NCNIYGGSMFFAYDVATFQAFIQELKSLSVLVCSHSY
RLKYKLTRFNRRADIIAKVQTTCMGAVTLFYWIAPIP
SICAHYYRSTNSTEPVRFVQHLEVKFYWLENRTSVED
YITFVLIMLPVVVMCGYVCNLKVMTICCSIGHCTLYT
RMTIEMVEQLESMASAERTASAIRNVGQMHSGLLKCI
RLLNTSIRSMLMLQWLTCVLNWSISLIYLTNVGISLQ
SVTVVVMFFLATAETFLYCLLGTRLATQQQLLEHALY
ATRWYNYPIAFRSSIRMMLRQSQRHAHITVGKFFRVN
LEEFSRIVNLSYSAYVVLKDVIKMDVQNVSYSYFTLL
RRVYN
``` cDNA Nucleic Acid Sequence
1176 nucleotides
Mosquito odorant receptor 5

```
ATGGTGCTACCGAAGCTGTCCGAACCGTACGCCGTGA    SEQ ID NO:15
TGCCGCTTCTACTACGCCTGCAGCGTTTCGTTGGGCT
GTGGGGTGAACGACGCTATCGCTACAAGTTCCGGTTG
GCATTTTTAAGCTTCTGTCTGCTAGTAGTTATTCCGA
AGGTTGCCTTCGGCTATCCAGATTTAGAGACAATGGT
TCGCGGAACAGCTGAGCTGATTTTCGAATGGAACGTA
CTGTTTGGGATGTTGCTGTTTTCTCTCAAGCTAGACG
ACTATGATGATCTGGTGTACCGGTACAAGGACATATC
AAAGATTGCTTTCCGTAAGGACGTTCCCTCGCAGATG
GGCGACTATCTGGTACGCATCAATCATCGTATCGATC
GGTTTTCCAAGATCTACTGCTGCAGCCATCTGTGTTT
GGCCATCTTCTACTGGGTGGCTCCTTCGTCCAGCACC
TACCTAGCGTACCTGGGGCACGAAACAGATCCGTCC
CGGTCGAACATGTGCTACACCTGGAGGAGGAGCTGTA
CTGGTTTCACACCCGCGTCTCGCTGGTAGATTACTCC
ATATTCACCGCCATCATGCTGCCTACAATCTTTATGC
TAGCGTACTTCGGTGGACTAAAGCTGCTAACCATCTT
CAGCAACGTGAAGTACTGTTCGGCAATGCTCAGGCTT
GTGGCGATGAGAATCCAGTTCATGGACCGGCTGGACG
AGCGCGAAGCGGAAAAGGAACTGATCGAAATCATCGT
CATGCATCAGAAGGCGCTAAAATGTGTGGAGCTGTTG
GAAATCATCTTCGGTGGGTTTTTCTGGGACAGTTCA
TACAGTGCGTAATGATCTGGTGCAGCTTGGTTCTGTA
CGTCGCCGTTACGGGTCTCAGCACAAAAGCGGCAAAC
GTGGGTGTACTGTTTATACTGCTAACAGTGGAAACCT
ACGGATTCTGCTACTTTGGCAGTGATCTTACCTCGGA
GGCAAGTTGTTATTCGCTGACACGTGCTGCGTACGGT
``` cDNA Nucleic Acid Sequence
1176 nucleotides
Mosquito odorant receptor 5

AGCCTCTGGTATCGCCGTTCGGTTTCGATTCAACGGA

AGCTTCGAATGGTACTGCAGCGTGCCCAGAAACCGGT

CGGCATCTCGGCTGGGAAGTTTTGCTTCGTCGACATT

GAGCAGTTTGGCAATATGGCAAAAACATCATACTCGT

TCTACATCGTTCTGAAGGATCAATTTTAA

Amino Acid Sequence
391 residues
Mosquito odorant receptor 5

MVLPKLSEPYAVMPLLLRLQRFVGLWGERRYRYKFR   SEQ ID NO:16

LAFLSFCLLVVIPKVAFGYPDLETMVRGTAELIFEWN

VLFGMLLFSLKLDDYDDLVYRYKDISKIAFRKDVPSQ

MGDYLVRINHRIDRFSKIYCCSHLCLAIFYWVAPSSS

TYLAYLGARNRSVPVEHVLHLEEELYWFHTRVSLVDY

SIFTAIMLPTIFMLAYFGGLKLLTIFSNVKYCSAMLR

LVAMRIQFMDRLDEREAEKELIEIIVMHQKALKCVEL

LEIIFRWVFLGQFIQCVMIWCSLVLYVAVTGLSTKAA

NVGVLFILLTVETYGFCYFGSDLTSEASCYSLTRAAY

GSLWYRRSVSIQRKLRMVLQRAQKPVGISAGKFCFVD

IEQFGNMAKTSYSFYIVLKDQF

Partial cDNA Nucleic Acid Sequence
474 nucleotides
Mosquito odorant receptor 6

TTATGCTTACCGGATGTTGCGATCGCGCACGTGCTTT   SEQ ID NO:17

TCCGCATACGCCAGTGCACACTTGATGGCGGTGGTGA

TGACGTCTGCTGCGCACCGTTTTCTGCTCGTGAGTCA

GACCTTTTCATTTCCTGCAATATCCTGTTTCTTTCCC

GACCCCACAGACGGTTAGACGGATATATGCTGGTAAA

GTTTGTCCTCTTCATGCTGTGCTTTCTGATCGAGCTG

CTGATGCTGTGTGCGTACGGTGAGGATATTGTGGAAT

CGCCTTGGGGTGATTGATGCCGCTTACGGTTGCGAAT

GGTACCGGGAAGGGTCGGTGGCGTTCCATCGATCCGT

GCTGCAAATTATACACCGCAGCCAGCAGTCCGTCATA

CTGACCGCATGGAAAATTTGGCCCATCCAAATGAGTA

Partial cDNA Nucleic Acid Sequence
474 nucleotides
Mosquito odorant receptor 6

CTTTCAGTCAGATCCTGCAAGCTTCCTGGTCCTACTT

TACCCTCCTGAAGACCGTCTACGGGAATAA

Partial Amino Acid Sequence
157 residues
Mosquito odorant receptor 6

LCLPDVAIAHVLFRIRQCTLDGGGDDVCCAPFSARES   SEQ ID NO:18

DLFISCNILFLSRPHRRLDGYMLVKFVLFMLCFLIEL

LMLCAYGEDIVESPWGDZCRLRLRMVPGRVGGVPSIR

AANYTPQPAVRHTDRMENLAHPNEYFQSDPASFLVLL

YPPEDRLRE cDNA Nucleic Acid Sequence
1206 nucleotides
Mosquito odorant receptor 7

ATGGTGCTGATCCAGTTCTTCGCCATCCTCGGCAACC   SEQ ID NO:19

TGGCGACGAACGCGGACGACGTGAACGAGCTGACCGC

CAACACGATCACGACCCTGTTCTTCACGCACTCGGTC

ACCAAGTTCATCTACTTTGCGGTCAACTCGGAGAACT

TCTACCGGACGCTCGCCATCTGGAACCAGACCAACAC

GCACCCGCTGTTTGCCGAATCGGACGCCCGGTACCAT

TCGATTGCGCTCGCCAAGATGCGGAAGCTGCTGGTGC

TGGTGATGGCCACCACCGTCCTGTCGGTTGTCGCCTG

GGTTACGATAACATTTTTCGGCGAGAGCGTCAAGACT

GTGCTCGATAAGGCAACCAACGAGACGTACACGGTGG

ATATACCCCGGCTGCCCATCAAGTCCTGGTATCCGTG

GAATGCAATGAGCGGACCGGCGTACATTTTCTCTTTC

ATCTACCAGGTACGTTGGCGGAATGGTATTATGCGAT

CGTTGATGGAGCTTTCGGCCTCGCTGGACACCTACCG

GCCCAACTCTTCGCAACTGTTCCGAGCAATTTCAGCC

GGTTCCAAATCGGAGCTGATCATCAACGAAGAAAAGG

ATCCGGACGTTAAGGACTTTGATCTGAGCGGCATCTA

CAGCTCGAAGGCGGACTGGGGCGCCCAGTTCCGTGCG

CCGTCGACGCTGCAAACGTTCGACGAGAATGGCAGGA

ACGGAAATCCGAACGGGCTTACCCGGAAGCAGGAAAT

GATGGTGCGCAGCGCCATCAAGTACTGGGTCGAGCGG

CACAAGCACGTTGTACGTCTCGTTTCAGCAATCGGAG cDNA Nucleic Acid Sequence
1206 nucleotides
Mosquito odorant receptor 7

ATACGTACGGTCCTGCCCTGCTGCTACACATGCTGAC

CTCCACCATCAAGCTGACGCTGCTCGCCTACCAGGCA

ACGAAAATCGACGGTGTCAACGTGTACGGATTGACCG

TAATCGGATATTTGTGCTACGCGTTGGCTCAGGTTTT

CCTGTTTTGCATCTTTGGCAATCGGCTCATCGAGGAG

AGCTCATCCGTGATGAAGGCGGCCTATTCCTGCCACT

GGTACGACGGGTCCGAGGAGGCAAAAACCTTCGTCCA

GATCGTTTGTCAGCAGTGCCAGAAGGCGATGACTATT

TCCGGAGCCAAGTTTTTCACCGTTTCGCTCGATCTGT

TTGCTTCGGTTCTTGGAGCCGTTGTCACCTACTTCAT

GGTGCTGGTGCAGCTGAAGTAA

Amino Acid Sequence
401 residues
Mosquito odorant receptor 7

MVLIQFFAILGNLATNADDVNELTANTITTLFFTHSV  SEQ ID NO:20

TKFIYFAVNSENFYRTLAIWNQTNTHPLFAESDARYH

SIALAKMRKLLVLVMATTVLSVVAWVTITFFGESVKT

VLDKATNETYTVDIPRLPIKSWYPWNAMSGPAYIFSF

IYQVRWRNGIMRSLMELSASLDTYRPNSSQLFRAISA

GSKSELIINEEKDPDVKDFDLSGIYSSKADWGAQFRA

PSTLQTFDENGRNGNPNGLTRKQEMMVRSAIKYWVER

HKHVVRLVSAIGDTYGPALLLHMLTSTIKLTLLAYQA

TKIDGVNVYGLTVIGYLCYALAQVFLFCIFGNRLIEE

SSSVMKAAYSCHWYDGSEEAKTFVQIVCQQCQKAMTI

SGAKFFTVSLDLFASVLGAVVTYFMVLVQLK

Genomic Nucleic Acid Sequence
2272 nucleotides
Mosquito odorant receptor 5 tctagacttgaacccatgacgggcattttattgagtc  SEQ ID NO:21 gttcgagttgacgactgtaccacgggaccacccgttt atcactatcactattaattaattataatatgcttttg tagcgatcagcctaccgggttttgtttctctggatat cttaagttcccatttgattatcaagatagaacaacaa cttgtaccttaaataatcattacgtacccttaatcaa cctgtgcatcaaggagttttcgcgaaagcaaaaatcc

Genomic Nucleic Acid Sequence
2272 nucleotides
Mosquito odorant receptor 5 gattgtctgatgttgtcttgattccatccgattcgtt actggttctgcaaaatcgtccaataatacggcaatgt ccttatcgatgcttgaatcaacatcacattgtttgca tttcgttttagcgtgcaaatatgttatttgcaaaga aggcaaggtaatgtgcttaagagtaaatacaattcgc tgtccattttttgtccaccagtgtgccagaacccgtg ccttttagtccttcgaatacatccgaccagtcagcaa gcaagtgcatcATGGTGCTACCGAAGCTGTCCGAACC

GTACGCCGTGATGCCGCTTCTACTACGCCTGCAGCGT

TTCGTTGGGCTGTGGGGTGAAGGACGCTATCGCTACA

AGTTCCGGTTGGCATTTTTAAGCTTCTGTCTGCTAGT

AGTTATTCCGAAGGTTGCCTTCGGCTATCCAGATTTA

GAGACAATGGTTCGCGGAACAGCTGAGCTGATTTTCG

AATGGAACGTACTGTTTGGGATGTTGCTGTTTTCTCT

CAAGCTAGACGACTATGATGATCTGGTGTACCGGTAC

AAGGACATATCAAAGATTGgtgcgtgataatgattga taaaaggaacctttgagcaactcctatccctttcaag

CTTTCCGTAAGGACGTTCCCTCGCAGATGGGCGACTA

TCTGGTACGCATCAATCATCGTATCGATCGGTTTTCC

AAGATCTACTGCTGCAGCCATCTGTGTTTGGCCATCT

TCTACTGGGTGGCTCCTTCGTCCAGCACCTACCTAGC

GTACCTGGGGGCACGAAACAGATCCGTCCCGGTCGAA

CATGTGCTACACCTGGAGGAGGAGCTGTACTGGTTTC

ACACCCGCGTCTCGCTGGTAGATTACTCCATATTCAC

CGCCATCATGCTGCCTACAATCTTTATGCTAGCGTAC

TTCGGTGGACTAAAGCTGCTAACCATCTTCAGCAACG

TGAAGTACTGTTCGGCAATGCTCAGGCTTGTGGCGAT

GAGAATCCAGTTCATGGACCGGCTGGACGAGCGCGAA

GCGGAAAAGGAACTGATCGAAATCATCGTCATGCATC

AGAAGGCGCTAAAGtaaggtctgccggtatgttgtgg atagaatacatttctagctgcttttcagATGTGTGGAG

CTGTTGGAAATCATCTTTCGGTGGGTTTTTCTGGGAC

AGTTCATACAGTGCGTAATGATCTGGTGCAGCTTGGT

TCTGTACGTCGCCGTTACGgtaactaaaagcactgta gtgatctgtctgccacaccattcactgctgtgtcttg ttttgtcactcttcccagGGTCTCAGCACAAAAGCGG

CAAACGTGGGTGTACTGTTTATACTGCTAACAGTGGA

Genomic Nucleic Acid Sequence
2272 nucleotides
Mosquito odorant receptor 5

```
AACCTACGGATTCTGCTACTTTGGCAGTGATCTTACC
TCGGAGGCAAGTTGTTATTCGCTGAgtttcagttact
tttccgttccctctaaccgtaccacttgtaccattt
gtttgagacagagcttgagcgtagCACGTGCTGCGTA
CGGTAGCCTCTGGTATCGCCGTTCGGTTTCGATTCAA
CGGAAGCTTCGAATGGTACTGCAGCGTGCCCAGAAAC
CGGTCGGCATCTCGGCTGGGAAGTTTTGCTTCGTCGA
CATTGAGCAGTTTGGCAATgtatggggagaccttcca
ctgtggcaagaaagatttctttattaatgcatctt
taatttacagATGGCAAAAACATCATACTCGTTCTAC
ATCGTTCTGAAGGATCAATTTTAAggggaactcccc
cacccgaccagacgacggaaagctaacgatgtgcaat
tgaatagtcattagtagcgttttgctcgcaaacgaa
ctaacccttgacttttaagttcactacggtgagga
caaaaatcaataaattaaatcgagaccgttgatgagc
aaaagaaaaaaaatattttactgattttcatttcgt
tccatcgactacataatcataattatatgccacattt
tattataagttttg
```

Genomic Nucleic Acid Sequence
931 nucleotides
Mosquito odorant receptor 6

```
aacacccatcttatcggcaaaattagtatttaccgtt    SEQ ID NO:22
tgaaagcggcttcccttcctggctgtttctcactctc
tctctctctgtctctcttattgatgccgtatgcgccg
cgtgctataggctagTTATGCTTACCGGATGTTGCGA
TCGCGCACGTGCTTTTCCGCATACGCCAGTGCACACT
TGATGGCGGTGGTGATGACGTCTGCTGCGCACCGTTT
TCTGCTCGTGAGTCAGACCTTTTCATTTCCTGCAATA
TCCTGTTTCTTTCCCGACCCCACAGACGGTTAGACGG
ATATATGCTGGTAAAGTTTGTCCTCTTCATGCTGTGC
TTTCTGATCGAGCTGCTGATGCTGTGTGCGTACGGTG
AGGATATTGTGGAATCGgtaaggcaccaggcggtgat
gagcgagtcgcgagtaattgaagcttttgcttttaaa
acacatcagagCCTTGGGGTGATTGATGCCGCTTACG
GTTGCGAATGGTACCGGGAAGGGTCGGTGGCGTTCCA
TCGATCCGTGCTGCAAATTATACACCGCAGCCAGCAG
```

Genomic Nucleic Acid Sequence
931 nucleotides
Mosquito odorant receptor 6

```
TCCGTCATACTGACCGCATGGAAAATTTGGCCCATCC
AAATGAGTACTTTCAGTCAGgtgagttgccaattgat
tgccgtttgcgttaatatttcagtaagagtgcgctct
ttcccttagATCCTGCAAGCTTCCTGGTCCTACTTTA
CCCTCCTGAAGACCGTCTACGGGAATAAgtaagcgcg
agagagagagagagagcagtatcgttcaccctttgga
tgaatcaatagatttctaatcatgaaccattgaaaaa
tgaatcaacattttcgctagttgcacaatattgtacc
attctatacagcttcaccacgaccaagcgtttgttgc
atcaggaccaaacacgtttcgacaagccgcgtcacct
gctggc
```

Genomic Nucleic Acid Sequence
11,103 nucleotides
Mosquito odorant receptor 7

```
ccgcccgggcaggtgacttacgcggtctgacttgctg    SEQ ID NO:23
gtgcgctgctttgtacggcaaacggctacacaagcga
atcgaattattttcctatcacgctgcgcttaccagcg
cctgctggtaggcaaagaatgtgcaaagtttcatttg
gcttggttcgtctgctttgctgtgaacgtgtgcacgg
ttgcatcgctaaggtttcggtgtgagccgagaagttg
cagatcgaaatctcttttgtgtgtgtgtgtgtgca
gtgggaagcattgtgtttagtgagaagtgaaaagaaa
agtgctgaaaaatgcaagtccagccgaccaagtacgt
cggccttcgttgccgacctgatgccgaacattcgggt
tgatgcaggccagcggtcaactttctgttccggctac
gtcaccggcccgatactgatccgcaaggtgtactcct
ggtggacgctcgcccATGGTGCTGATCCAGTTCTTCG
CCATCCTCGGCAACCTGGCGACGAACGCGGACGACGT
GAACGAGCTGACCGCCAACACGATCACGACCCTGTTC
TTCACGCACTCGGTCACCAAGTTCATCTACTTTGCGG
TCAACTCGGAGAACTTCTACCGGACGCTCGCCATCTG
GAACCAGACCAACACGCACCCGCTGTTTGCCGAATCG
GACGCCCGGTACCATTCGATTGCGCTCGCCAAGATGC
GGAAGCTGCTGGTGCTGGTGATGGCCACCACCGTCCT
GTCGGTTGTCGgtatgtgtgtatgtgtgtggccgttt
gggaaagtgtctttgcggcagaaccccaatctactgt
```

Genomic Nucleic Acid Sequence
11,103 nucleotides
Mosquito odorant receptor 7 tacgcttgactggttttgttttttctcggtggag ggacgggataaaatatctgaaagaataattgagtcaa cccacaggggatgcaagacatcgcaggcagagagtt tgggtttgatttataccgcacaccgaatatcttcac ggttcataagcttaccgcggtgaaaagggaactccc catttccctgttttcttttttttcttcctctcgataa attactcatcgcttttcgtttttttttttttgttgtt gcttctttcttctttcatccctactagCCTGGGTTAC

GATAACATTTTTCGGCGAGAGCGTCAAGACTGTGCTC

GATAAGGCAACCAACGAGACGTACACGGTGGATATAC

CCCGGCTGCCCATCAAGTCCTGGTATCCGTGGAATGC

AATGAGCGGACCGGCGTACATTTTCTCTTTCATCTAC

CAGGTACGTTGGCGGAATgtcctgcgcgtcacagttg gcagtcagtgagcggcaacacggcgaaaaaatgggac taaaaccggtcttcacagagccaacacattcctacag caattgcataccttcgggcggtcgggactgggcaatg cagctacaacatcctcgcctaaagttatgcaattcga gcgacaaatgttgccgtgttagggcttttttgtgataa tagtcgttttttgtcctctcgcttatcaaactctatc aacggaggaaatccattttcgctacaatgcctacagc tcaagtttcaaggtcaatcgagcgggtggggatcaac ttttttattcatttgctaacgccccatcaacaaatt ctatgttctcaatggcaaagattactgcccgcaccaa tcgcccaacgaaacggcaaaagaaaagcgacgattat gaagatgtccaaaccattgcccgcccgacgctttatc tgatgatttgcgggatggcttttacttgtctgctact ttcaggcacaaaaggaaatgaaaccagcgcaggctcg tttgccggcttgcggaggttcttcaggcactgaggct gagtacttaaatcgaacgattttttacgattctggatc cagttttatgatgtggcctgcattacagtggcaatta taccctgatgttcatttcattgcattttgtaagtttg tgctggtaacgcccgtaacgattaattcttttcaaag agattctttcaaagagattcaaatgtgtataacaaa tgctaacgaatggaccgtacttggagggttgcggaaa gtaacgttttaaaatattcatcacaatcctctgcaaa cttgtgcttaattaattggtgcacaataagtttaaac tgtggcggcagatgtgtcgctgtccgcttccttcctt cccagcaagctcgtgcgaaataatttattccatcatt ttaatacagccgtttgtgcatttttaattagcaaagca atataaaaagcagctaaccatccccattaaaacaaag tgcttccgggcccaattgttatggcggtggaaagtaa tggttttaccagtggaagtgtcctttcccatcgtggg tacttcgcgatattcttgtcttatacaagtgcataca gaaaaaaaggacaaatcctccttgctatggtctaagg ccagcttcggtaccgcttccgctccgggatgtcataa agtttgatgggtgtttttaacattacttccgctctta accacctaatggacttttcatgcttgagctaaagtta aaccagccaccagcggtacgcaccgagccacggttga tttcggcggcggcctcatccccagttttgcgccacca atattgccttcattaatctgtaccctcggagcgttag ggccccgcggacgagtcctcgttgtaatgcaccgccat gccacgggacgggataatccgttgggacggcgcgaaa gcgactatcgcggacggattggttcgaccgtgctaca acacattttatgcttcacagatttacttcctgctgtt ttcgatggtccagagcaacctcgcggatgtcatgttc tgctcctggttgctgctagcctgcgagcagctgcaac acttgaaggtaggtacggtagcaaacgtggttgtctt tacatccgcgtgcagcattatccttatcgacgtgtag tgttaacggtaaaagaggaagcgataaaaaagcaaca ttctctcacaccctcgatctctctttattttctctct ctctctctctctctctctctctctctctctctctctc tctctctctctctccatctcctcgggcagGGTATTAT

GCGATCGTTGATGGAGCTTTCGGCCTCGCTGGACACC

TACCGGCCCAACTCTTCGCAACTGTTCCGAGCAATTT

CAGCCGGTTCCAAATCGGAGCTGATCATCAACGAAGg tatgtgaaacgtgtgctcgtggcagacggactcaaag agagcataacacaatcccctggtagttcatttcaatg accttaacactcggcaagctaagcgagacagtgggga cagtgagaaagagagaacaagaaaaaaaaccatcatc cgtacgacatcatcgctacgtaccggtatttcaggat gaggaaataaaacgctaggggaatgaaagtgcgacag aatgataaaacaatccccacccaggcccccagcctgg acgaacggatgtagtgtgcgaagcgagcaaaaaaagt caaataaattgaagtttaaaaatagattttcccgtc catccgtggtggagcgtaaagcccggcggacaacttc

| Genomic Nucleic Acid Sequence
11,103 nucleotides
Mosquito odorant receptor 7 |
| --- |
| gagcacggcgaccgtgcacagtactgtgccacagttg |
| tagggacggataagctccgttcctttttatcctttt |
| tttttggagatttgtttgcgttcgcatcgttagacga |
| gcttagtgccgtgttgctctaattgctatttattata |
| aagcgcttccaaatagaagatcggttctctccattta |
| atctatcgcgcctgtacgcctgaaactatgcactgtg |
| ctgtgaaaccgtcaagctcgagcacgacgaatggccc |
| accgtaccacgcccgtggtgcccaaagcgcaacgcga |
| attgcatgttaacaaacctttgcctaccatccaatcc |
| gtgtgaaattgcccgctctctttctctcttttgcgct |
| ttcggtgtatcgaacggttttgtccctttttttttact |
| ttgctcttgatctcttgctgtgctcactttcatctca |
| tgttttgcctgacggtggtgggttttcgaaaaaagag |
| cgatttcttctgcgtgtgtgtgtggtttttttaaata |
| accgctccaggtcgtgttgaacgctgcaggaccgatc |
| ggagctagtttattatcagctttagtgtttatcccac |
| ccatgccccacatcacgtctgtggagagtgggggaag |
| cttaagtccaatgtaatttaccgtgtttctgttcgtc |
| accttcttcgtcgatggagattggtgcggttggcacg |
| ataaaagcccactgcacgttacggaccgagggaaagg |
| tcttttttgtaggcctagcaacggtcctcattcaccgc |
| atgggggtgtagctcagatggtagagcgctcgcttag |
| catgtgagaggtaccgggatcgatacccggcatctcc |
| aacccacacaaaacgttttttaagaagattttaggg |
| aagatattaacgcgggtacactgtgctcctctaagtt |
| ggaagagtagatgagatgatgacaaggggagaaggaac |
| atgtgtacgtgtttgatagcaaacacacaaacaacaa |
| tatcatctcgataataatctgatgtgtgatgtgtgtg |
| tattgttgttatgctgcctttgccatcttgtccctct |
| ctctcctgttcaactcctaaaagaattgtttggagtc |
| ctctcagttcctcgtaaagatcctttcgagattcttc |
| tttccttttttattatttattccacgagcctctgacat |
| aagtagccttccgcttatttccttctccttgcacttg |
| tcagttccgtgtagagcgtcattttgaggtttacaca |
| tttcccaccgacgcctgattgttacattgtcatctac |
| attgctttccgtttaccgttccgcccttttttttaa |
| cgctaccacagAAAAGGATCCGGACGTTAAGGACTTT |
| GATCTGAGCGGCATCTACAGCTCGAAGGCGGACTGGG |

| Genomic Nucleic Acid Sequence
11,103 nucleotides
Mosquito odorant receptor 7 |
| --- |
| GCGCCCAGTTCCGTGCGCCGTCGACGCTGCAAACGTT |
| CGACGAGAATGGCAGGAACGGAAATCCGAACGGGCTT |
| ACCCGGAAGCAGGAAATGATGGTGCGCAGCGCCATCA |
| AGTACTGGGTCGAGCGGCACAAGCACGTTGTACGgta |
| ggtatggtaatttctaaggtgtggtgtaaagcctcca |
| ggttccatgaaaaagggatactttaccacagtaagag |
| tttgttttgctggacttacattctttggagcattgtt |
| tggtgttgtgctgaaaccggttgcaatatcgttttgc |
| gaagaaattatgtgtaaagcgtattacaatctcattc |
| ctctgttaatctgtaccaattgtgtcagccccgaccg |
| aaagcaggcctaattcgtaccagaaaaaccacaagct |
| gtttgtaagcatcgatacgcccgaagctttcaatcca |
| gccaaggcgccacctactattgacgtgacttttgca |
| cgttcacactctccctctcccattctttctataacca |
| atcgtcgctcagccagcatcgcccggagtgaagtttt |
| tatttgaacgatatcacccgtatcgattttccactaa |
| acatgcttaaatcgtttcacaaagctccccaaaatcc |
| catttcaccaatccaccaatttgaagtccgtcgtcct |
| ttgtgtccttgtgtttgtgtgtttgtgtgagctggag |
| acatgggggagtgagtaaccgaacaacctcttgccgc |
| tgcttcacgatatcgaacagcaccaagataagcatcc |
| cttttttccctagccgatgtctccgatatctcgattcc |
| gcttccagcgaggcaaagaaaaaggcgaactggctga |
| cctcacccggggcgaggaaaaagcgtagggattacgt |
| cgagcagcacgagttgtgatttcttcttcttctggtt |
| ccataaatcgctgacggtttccattaccgcctgcgga |
| gtgcacacacgtgaaggggaaagcgaaaacgtttagat |
| tccagcagcaacggcagcaccagaagcagcagcagcg |
| cggcaaattgaatcatcctgacgcgatgagttgtctg |
| ggttttcgggtcggtggcttacagcaccacaccatct |
| gctgcagctaatacagctgtaaatttcgttagacata |
| gacttgattttacaatattacacacacacttacacac |
| acagctatagatttgtcgcttggcgtatggctctgta |
| cggcgtgccgtacatgccgcgagccgtgttgctgctg |
| gttgcgatacggatcacgtccgattcgattcagcctg |
| cgtgttttggtgaagatccttatcggtgacccactt |
| tcagtgtgtcgagagcgagggtcactatggcgcctgt |

Genomic Nucleic Acid Sequence
11,103 nucleotides
Mosquito odorant receptor 7 cagttggaaagctaggctcgattcaaagggccattgt
gccagtgttctttttaagatagcgataagcttttgat
cgaaatagtaaatcaaacattgtttctttttttcctat
tccaaactgttgccaacctcattattacgttttgcag
cgggtgtatagtaaattgcatactttaaggcgtgatt
ttcaaatgtagcgttccgtatgcagaaacgccatgga
ttatgcaatttaaacaatgctgcttccttaacattca
aataacggcttattaaggaacttttttgtgcaatttgt
ttttaacagcaaatagttagctcagaacgatcacatt
tagtatcgcttcaacaaagaactcttttaaacacaca
atttgtaatgccattccctcgagaaagtttcttgtca
gtcctcctctgcatcacagcaacaaccaaacctgctc
atgtttcctgctcgtttcctagctgttttgaacgtta
tttccgattcctgtgcttgcccgcttttcttacaatc
aaccacaatggttcagatttcgctcttatttattga
cccactgctttcgtgctgaagcccgtggaaacaatgc
gccaagctcagcatccagccatgcatgtaaaatgagc
cacgcgacagattttagacatcgctttcgctctgcac
cggaggtggttttattcttgtttccgattcccacgtc
cattcgtcctgggtccgtccgccgggcccgaaaccgt
aagccgtgcggggaattacgcaatcgaaacgagccag
aaaatgagcacgccaaatgcaaagaaaatcccctttt
gagtggtgctcctgccaccactcatctccccaactgg
tgggtgaaaaaccttgtgcgcccccttctcttccaga
aaaaaaacgcctcgctcgcacaaaaacatgctcgccc
ggtgaagctgcgtatgtcgcagaagctcaaaccaacg
ccgccagcaagcatcaacaatttctattcaaacaccc
aacgcagcgcccaaaccgggtgcactgtactcagtag
cgaagatgctcagattgtcccgtgcgctgctttcgat
gcccgtttcggagcgggaagccatcgcttgccaacgt
tggcgatgtcttttagccgtggatttgaattttctga
atatcacaggcgggcgcggtttgcctgcaaggttgtt
gcttcccacacgagcattgctttccgtaccgcggtgg
ggcgagttttcaacgcaaccttctacaagcaacgcca
caacgcctgggagcgatatttaacagaaacaagaaca
tcccgaacttcagcacatgccgtgatttgcctgttgg
aaaagctttgtgagcgtgtgagttgaacgagctcta
ttttcccagcgatgggtggcatttgtgtggcatgcta
tcgtcagcttttcttgaatctttacctctccattcgc
ctccattagtacacgcgtatggaaatgggtgcaacg
gatcagaacggattttccgcgacagacttaataaagg
gaaagcaacgcgttttttgcatgtgtagtgtttatga
gctttatgccgttactttgcaattaaaaatagcaaaa
aataacagtttttttttgtaagcggattacaaagaat
gtatcagaatattacgtgaaacattcatttcatgctg
ttaacgctcaaatagaatagttttgtaacacggattg
cataccttgccggtatcggttacattttcgcctaaca
gtatgcaatctgtttagctttgttgtttaatgactgc
gttggtagtacaatatttatttacaccgcgtaattta
tctcacaaattgcaaaaaaatgtcaatctgtatcgat
tattcacacaaatcagatcccggaaccagtgtagccc
aatgtgctcttattgaattaccacgaacaaatcaacc
tgatgcccgggtccgttggcaaacagcttgcgccgaa
gccgctcagtgtttcgtgcactaccgtgctgccatt
tgctgccctcatcgaacagataaacagaagggcaact
cttgtgagcatcgcaatgcccgtctgaagttccgtcg
aaaatgggcctaaattcaatttgacgcatttacccgc
gaacaattgcgcgaaggctgtcaagtgtgttccacga
actgcgacaacaagcacacacacaaacacaaatgtta
tcgtttcggcatgtttctcggtacaaagcgtgtggcg
ctatgtggcatgccgattcccagacagagtgatcgat
agtaaatgtagcctatccggtagcattcaatttcctt
ttctatcctcgcaaacaaagcccattctggggaggcg
tggtgaagctttcaaaggcattgtgaaacaaatgtcc
tggttcggagggatgctggggaaagcaaacacggtgc
cgccatcgctgctaccgtcaatcgatcatgcatgatg
tgattaatatttgtgttattcacctgcgtatctatgc
gtccgtcgtgtcgttcggatttccggaagtcaaggaa
aaagcgactccatttgggattggttttgcagcgaaa
aatcaaaacattcgcacaaaaccgtcctccatttcaa
atgcctacacttgtcactgtatatctctctttctctc
gttttgccacgttgcagTCTCGTTTCAGCAATCGGAG
ATACGTACGGTCCTGCCCTGCTGCTACACATGCTGAC
CTCCACCATCAAGCTGACGCTGCTCGCCTACCAGGCA
ACGAAAATCGACGGTGTCAACGTGTACGGATTGACCG -continued Genomic Nucleic Acid Sequence
11,103 nucleotides
Mosquito odorant receptor 7

TAATCGGATATTTGTGCTACGCGTTGGCTCAGGTTTT

CCTGTTTTGCATCTTTGGCAATCGGCTCATCGAGGAG gtacgtgcgctcggcgtgttgccgtgggaaagcattc tccctgcccatatcgcttcattctcccagatcacac atttgcatcacaaagccagcacacttttgcttcgccg ctgccactcggcttctgaatgttttcacttctcccat acttctcccgtgcagAGCTCATCCGTGATGAAGGCGG

CCTATTCCTGCCACTGGTACGACGGGTCCGAGGAGGC

AAAAACCTTCGTCCAGATCGTTTGTCAGCAGTGCCAG

AAGGCGATGACTATTTCCGGAGCCAAGTTTTTCACCG

TTTCGCTCGATCTGTTTGCTTCGgtaagtgtagcctg gtggctggcacagaacaggctggcaaaacagggactt tggctctagcctgatgggtggtatatgtgtgtctatt ttttgctaccattctcgcatcccttcctttccagGTT

CTTGGAGCCGTTGTCACCTACTTCATGGTGCTGGTGC

AGCTGAAGTAAacagccgtggcccggaaggatgtgtt ttttttcgctcgttcggttgtttgtttgtgcacactt tctcttggacattttctctactgcaaaggtttaacaa acagcaacaacaaataatcccaagttttcttttacag atctttgcaaaatgattagatttaatagattaacag tgcttgattatctgtcctgtagcaaccggggctgaag aacgttgatttggtaaaagtacaaaagggacgttgga aattgaaccaccagaagagtgatatttatgcaaagct caccaagggaaatctatgtatgtgtgatttgcgctca tcaagcactgtatgtgcctttcaactagtgcagcaat aaagagtacaaatgtttcttagcgcaccgtacattgt cgtttcggcgttttaaccgttgttgataatacacaaa agatgataaaataataataacaaaatgttaatatg agtaagtactaaatagagaaatcgttttagtatgatc atacctccaatcatttgtttgaaattaactttaattt taactcaaattaaaccgatgttttactttctgtgaga attattgtggaagaacttaatggaagtataattaaat tgattgctaactttatgcgttttcaatttacgaacg ctagtcttcaaacatcgcttcaaaagtattactacca cattattcatttacttatagttatatttattgcctct tcatctttccatggccagaactactgcagaaaagctt cttttttgctcgctttccgatggttggttggacgaag ttggtaacaaacggcaagcaattagcataaactattt -continued Genomic Nucleic Acid Sequence
11,103 nucleotides
Mosquito odorant receptor 7 tcgcatcgagatgaaatgaatgtaccactagaaccg agtgaaatgaattacttttcaacttgcacgccaaaac cattatctaaagtacgcacaacttaaaaacaaacccc aaattgtcgtccaccccttcattccactttcttgctac actttccgaccgagttctgtagcgccagcagcaaaaa aatacatataaaaccttcatcactcaagctgtatcga gccagcgtgggttgtgtttgactgtgctgtgaaagaa agaagaaaaaaaaaacacttccacgggaagctagcaa ttggaaatgcataaattaaccggaagaaattcgcaaa accccgcaccgacgtaccgcaccgcatccgtaccgat accggaacaaacggtgtgcgcgaaagaatccgctagc agccccactggcacgggtatttgcttttggttctgtg tttttcttccactggtttgggtgcctgggcgaaggct agctcggctactttcccggggccgcaattttctgcag cccaaggcggcgtgctcgtggggccaaaagaat Genomic Nucleic Acid Sequence
5,543 nucleotides
Mosquito arrestin 2

GGTAAAGGGCTGGATGAGGAGAGGAGACTTATATTTT    SEQ ID NO:24

TGGAAGCCTTTGGTAGGTGACAAGGGGGAGTTAGTGA

TAGGGGAGTGGGGCCAAAATAGGGAGGAGGTAAAATT

TATGGTACGCCCCATAGGGGAAGAGGAAAGTGACCAG

AGCAGGCCAGTGTCCCCGCTGGGGGGCTCAACGGTGA

GCCGGCTGTCCCTCGGCGGGGAATGAAACCCTTACA

AAATAAAAACTAGCGTTTTTCTACTCTCTCAAATGTC

CAAAGCTGTTGCTCAACTGGGTGCTGAAAACCCCTGC

GTTATGCAAAGCATTAGTCAGCTGAAGGTGCAAAATC

TTCCACAGCTTGCATAAAGGAGCTGCTGATCCGTAGC

TTGTCCGTGCAAGATCATACGATCTTTATAATTCGCA

AATTCGCCTTCCCTTCTTAATCCTTTATGACGCCCGT

GTTGGTTCGCTCTTTCCTGCGACACACGGTGCTCAGC

CAAACGTGACCTAAACACGCACCCCACAGCGTACGCG

TGACGTCACGACCTTTGCGTTTTCGCGGGGAAATAA

GATTAACGTTCGCTGCCGACGCCCGTTGACCGTTGCA

TCGTAATTTCGTATACCGTTCTGCGCGTGTACCCCTG

CGTACGTCCAGGCTGTTGCGTATCGCACCATCGTACG

-continued

Genomic Nucleic Acid Sequence
5,543 nucleotides
Mosquito arrestin 2

CGAACGGAAGGCATCGGGGAAAGGGACGCAAGGATGG

GCATGAATTAGCTGACACTATTTGTCCCCTCCCCCGT

AATGCAGGCGCAACCACCTGGCAGCTCGTCGGTGGCA

GTAGCTCGAGCCTAATTCAGTTAATGGCAATCGGGCA

AGCGTCGATCGATTTTCCCGCTGCAAAAGCCCGCACG

SKKWYSGTCCGGGAAACCTTTTCGGTGTTTTCAGTGT

ACGGTCCACCACACGGGCGGTAAAAAGGTATAAAACT

GTCCACCAGCCGACCGTTCGATCGCACTTCTGGTTGT

TCTTTCAAACCATACAATACCCGAAACTAGCTGAGAA

CTTTGTAGTTCAAGCAATTGAAAAAACGCAAGAAAAC

AGCGCTCCGTAGAACGACCCCGGAGAATAGACACGCA

ATTTTGTACGACCAATCTCGAAGCGAGTGAATTGAGG

GAGTGAGCTACCGTGTGTGAGAATACTCGTGATACAT

TTCGAAAGTTCTATCTGATTGTTTGCTCTGTGTTTGC

GAAGACACAAACTAACGCGCAGTGATGGTTGTCGCAG

TGAAAGTGTTTAAAAAATCCGCCCCGAATGGCAAACT

GACCGTCTATCTCGGCAAGCGTGACTTCATCGACCAC

ACCGACTACTGTGACCCGATCGATGGCGTTATCGTGC

TGGACGAGGAGTACCTGCGAGGCCGCAAGGTCTTCGG

CCAGGTTGGTTTACTGGAAGATCTCGATCCTCGATGA

CTGCAGTTCAGGAAGTCTTTAAGAACTTGTTAAGTGA

MCAGATATGATTCTTTCGAGTGTCTACTTACTAGATG

AGTGAATATGTGTGCAATTTGGAATGAACTCTCAAAT

GCCTGGAGCAGAAGCAGAGTATCGATAACTTGGAATT

ACAATCAAGCCTCGTTAATTAGCCAATACTCATGTTG

CCATGTTCTGAATTTATCAGATCTTTGAAAGGTTCGA

GGATATTATGAAGATAATAGTGCAGACGGCCAATACA

AAGGACCTATTATCGTTCTATTGCTGAACCACAATGT

TACAGCGTTTGATGAATATCATCCGATTAGTTTCAAT

ACAATCCAATTAGTGAGGTGACATACTAGAAGGACAC

ACAACTGATGTCATAATGTAGTTGAAATGAATGCTAA

TATCAAGGGTATTAAAGGTTTTTAATGAACTCCAACT

CATTGGATAACTCTTTCGAAGAACTTTGATGTCTCAG

AATAGCCGAATTCTTATCTTTTACTAACATAGTTGCA

AGTTCTCAGCATGTAACTGTTCTCCAACCCACTTCAA

TGTTCCATTTCTCTCTCTCTCTCTCTCTCTCCCCG

CAGCTCATCACCACCTACCGCTATGGCCGGGAAGAGG

-continued

Genomic Nucleic Acid Sequence
5,543 nucleotides
Mosquito arrestin 2

ATGAGGTGATGGGCGTGAAGTTCTCCAAGGAGATGGT

GCTGACCAAGGAACAGATCTACCCGATGGAGAACGCC

AACATGGAGATGACGCCCATGCAGGAGCGGCTGGTGA

AGAAGCTGGGCGCGAACGCGTTCCCGTTCACCTTCCA

CTTCCCGAGCATGGCGCCGAGCTCGGTGACGCTGCAG

GCCGGTGAGGACGACACGGGCAAACCGCTCGGCGTCG

AGTACGCGATCAAGGCGCACGTCGGCGAGGACGAGAG

CGACAAGGGCCACAAGCGCAGCGCCGTCACGCTGACG

ATCAAGAAGCTCCAGTACGCGCCGGTGTCCCGCGGTC

GTCGTCTTCCTCGTCGCTCGTCAGCAAGGGCTTCAC

CTTCTCGCAGGGCAAGATCAACCTGGAGGTAACGCTC

GATCGGGAGATCTACTACCACGGCGAGAAGATTGCGG

CCAACATCGTCGTGACGAACAACTCGCGCAAGACTGT

CAAGAGCATCAAGTGCTTCGTTGTGCAGCACTGTGAG

GTTAGTAGTGATGGAGCATTCCTGGGAGGGGGCACCT

AGATGTGATGATCGGGTTAATTTAACTCCCTAATCAT

TCCCTCCTGCATTYTAGGTCAGCGATGGTGAATGCAC

AGTTCAGCAAGCACATCGCCTCGCTGGAGACSCSCGA

GGGTTGCCCGATCACGCCCGGGGCGAGCTTCACGAAA

TCGTTCTTCCTGGTCCCGCTCGCCTCCAGCAACAAGG

ACCGCCGGGCATTGCGCTCGACGGCCACCTGAAGGA

GGATGACGTCAACCTGGCCTCGTCCACGCTGATCAGC

GAGGGCAAGTGTCCGTCGGATGCGATGGGTATTGTCA

TCTCGTACTCGCTGCGCGTCAAGCTCAATTGTGGCAC

GCTCGGTGGCGAACTCCAGACGGACGTACCGTTCAAG

CTGATGAACCCAGCACCTGGTAAGTGTCGTAAGGGAG

CGAACTTCGTACATCATCGAATATCTGGTGCTAATGC

ATATTTTTTTCCTATTTCTCTATTATCAGGATCTGTC

GAGCGAGAGCGCGTGAACGCCCTGAAGAAGATGAAGT

CGATAGAGCGTCACCGTTACGAGAACTCGCACTACGC

CGACGATGACGACAACATCGTGTTCGAAGACTTTGCC

CGCCTGCGGATGAACGAGCCGGAGTAAGCCTGTCCCG

CCTGATGCGGCATTCACYKRCAACCATCCTTCACCCC

AAGGGCGAACGGCTTTAATCCGGAGAGGGGACAGCAA

ATGCCATGTCTTCTGTTCCATTTCCTCCACCGAGCAC

CCGAGCAGGCAGCAAACGCAAACATGAAGAAAACACA

CACGCCCCAAAAATCCTCCCAATGCTTTTCCGCGCCA

AGTATGCTTTCTTTCATGCCCTTTTAATGCTCCCAGG

Genomic Nucleic Acid Sequence
5,543 nucleotides
Mosquito arrestin 2

AGCGGTACGAGCGTGCGTGTGATGGCTGGGCGGGAC
GAACGAGTGTCCCTCGGGGGGACCCTTCGTCTAGGCT
AGCGGCTAGAGTGGTGGTCACCTGAGAGACGCTCATC
AGCCTTTCCCAGCCGTAACCACACGTAACMATGTCCA
ATGTGATAACACTGATGATGCTATTTAAATTATTAAA
CGCAAAAAACACGGCGCCGCTAAGCAACGAACACTAG
AGCGCGCGATAAGGAAACAGCAAGAAGAAGAAGAAGA
AGAAGTAGTAGAGAAAAAACCTATCTAGTGAAGGAAC
AACCTACCCTATAAGTGCTCCCCCAAAAACTATAACG
ATATATGAAGTAACGAGAGAAAAACGACATGAAAATG
AGGAGTGTTAATGGTAGCCTCCGCCAAAAAACAAACA
AACGACTAACGAAGCCAAAACCCCCTTCCTAAAATCA
CAACAAGCAAACTAACGATTATGAAATGGTCAACACC
AAATAGACAACAAATTTGATTCATCGATTAATTCCCT
GCCGAGAAACTGTGCCGAGAAGTTCCCGAGAAGAAA
ACCAGAACATCAACGACTGCGCAGTCAAGAGGTGGGG
CAACGCGAACCAGCAACTCCCTTGGGAATGCAGAATC
CCCAACTGGGGGTGCGATGGTTACAATCCTCCTCAAT
CGAAGAACACGCACATGAGTAACGTGCAGCAATTAAT
CGATCAATCGAAGAGCAACTTACATCGAAAAATGTTT
AAAAACGAACAAAAAAAATATCATAACCATACACAA
GAACCAAGCCCCAAAMCCCAAGCAAACACCAGAAGT
GAACGAAATCGACGATAATCTAGTGCAGCTCCGGKTC
GTACGTGGACGCTTTTCCCCGGKTTGGCTATGGTGRA
AACCGGCCMCATCCGAACCGCTGGCGACAGCAGCCTT
AGAGTGTAAGACGTTTTATGTTTCTGTTTTGTTTTTC
GTGGTGAGACAGCAATTGGAGCAGGCAATTTAAGGGA
AACGAGCAAACGATTTAGGCAAATGGAAGCTAGAAGC
AACAAAGACGCGCGCAGAGGAAGAAAAAAAACAGACAA
GAAGATAAAAACAAAACCACACGAGCAATGAATGCAA
CGAATGCGGTTGGGAAGTGAAGAGCTAAGGAAAACGG
TGCGGAGAAATGGACATGAAGATGTCCTTTTCCCGGT
ACCGTTTTCACTTCCGATTCATTCACCCCAACTCGTT
CAGCGCTCCTTACTGCGAGTCAATTATTGTTTCAGAT
TGTGTTCGATTGGTTGATATAAGCTTGTTCATGCAAA
ATGGGGTTTTTCTTATCTAAGGAAACCATGCTATAT
TATTACCTGCAAATGCAATAGGAACAGAGCAGAAAGG
AAACTTTATAATCMACTAAAATYWAACCMAATTAATT
GGAAAAGAGAAAAAAAACCCACAACTTCAAACCAATG
CAACGACCTATTGATACATTTGAAACAAACCCAAAGG
TCACGCAACACATAGAGTCAGTTTTGAGTTTTGCGAT
GTACAGTGGACTGTTAGTAGCTGTGTTTATTTTGTAT
AAATCTAATTTGGCTATGTTATTATTGTAATTGGAGA
AAAAATGCTGAGCAACCAAAAAAAAAACTAACTTACAA
ACAAACCAGCAACTATTGAATTTGTTTTTATTTGTTC
CAATTTGTACTGTTTTTTCAGGTTTCTTTTTTTGCGT
TTGGTCGGGAGGCTTTCGGCCAACGGTCCACAGGTAG
TAGAGGGGGAAAGAAATAACTGGTTGATGGAAGAAAA
AAAAAAAGCAACCCTTACCCTAACTCTTTGTAAAGAT
ATGTATACGAATGCACCGGTATTTGCTCAATTAGAAT
GTATTCCCTTTTTGCTGGAAGATAGGGGAAGGATTGG
GATGGACCGTTTTCTGTTTCTAGAGAACAATTTACTG
CAACGAGTGTGATATTCAAGGATGTGATAATGCATTT
TCCAGCAGAGAGTTGGAGTTGGCACTATTGTGATTGT
AATTTGAAACTTTGAAACTATTACAAATACCAAACTT
TCCTTATAAAGGGGGAAATTCTGAAAAGAAAAATCAT
ATTTCACCCCAGTTGGGCTAAAACCATTTG

Amino Acid Sequence
398 residues
Mosquito arrestin 2

MVVAVKVFKKSAPNGKLTVYLGKRDFIDHTDYCDPID   SEQ ID NO:25
GVIVLDEEYLRGRKVFGQLITTYRYGREEDEVMGVKF
SKEMVLTKEQIYPMENANMEMTPMQERLVKKLGANAF
PFTFHFPSMAPSSVTLQAGEDDTGKPLGVEYAIKAHV
GEDESDKGHKRSAVTLTIKKLQYAPVSRGRRLPSSLV
SKGFTFSQGKINLEVTLDREIYYHGEKIAANIVVTNN
SRKTVKSIKCFVVQHCEVTMVNAQFSKHIASLETREG
CPITPGASFTKSFFLVPLASSNKDRRGIALDGHLKED
DVNLASSTLISEGKCPSDAMGIVISYSLRVKLNCGTL
GGELQTDVPFKLMNPAPGSVERERVNALKKMKSIERH
RYENSHYADDDDNIVFEDFARLRMNEPE

| cDNA Nucleic Acid Sequence
1,190 nucleotides
Mosquito arrestin 2 |
|---|
| ATGGTTGTCGCAGTGAAAGTGTTTAAAAAATCCGCCC SEQ ID NO:26 |
| CGAATGGCAAACTGACCGTCTATCTCGGCAAGCGTGA |
| CTTCATCGACCACACCGACTACTGTGACCCGATCGAT |
| GGCGTTATCGTGCTGGACGAGGAGTACCTGCGAGGCC |
| GCAAGGTCTTCGGCCAGCTCATCACCACCTACCGCTA |
| TGGCCGGGAAGAGGATGAGGTGATGGGCGTGAAGTTC |
| TCCAAGGAGATGGTGCTGACCAAGGAACAGATCTACC |
| CGATGGAGAACGCCAACATGGAGATGACGCCCATGCA |
| GGAGCGGCTGGTGAAGAAGCTGGGCGCGAACGCGTTC |
| CCGTTCACCTTCCACTTCCCGAGCATGGCGCCGAGCT |
| CGGTGACGCTGCAGGCCGGTGAGGACGACACGGGCAA |
| ACCGCTCGGCGTCGAGTACGCGATCAAGGCGCACGTC |
| GGCGAGGACAGAGCGACAAGGGCCACAAGCGCAGCGC |
| CGTCACGCTGACGATCAAGAAGCTCCAGTACGCGCCG |
| GTGTCCCGCGGTCGTCGTCTTCCTTCGTCGCTCGTCA |
| GCAAGGGCTTCACCTTCTCGCAGGGCAAGATCAACCT |
| GGAGGTAACGCTCGATCGGGATCTACTACCACGGCGA |
| GAAGATTGCGGCCAACATCGTCGTGACGAACAACTCG |
| CGCAAGACTGTCAAGAGCATCAAGTGCTTCGTTGTGC |

| cDNA Nucleic Acid Sequence
1,190 nucleotides
Mosquito arrestin 2 |
|---|
| AGCACTGTGAGGTTACATGGTGAATGCACAGTTCAGC |
| AAGCACATCGCCTCGCTGGAGACGCGCGAGGGTGCCC |
| GATCACGCCCGGGGCGAGCTTCACGAAATCGTTCTTC |
| CTGGTCCCGCTCGCCTCCAGCAACAAGGACCGCCGGG |
| CATTGCGCTCGACGGCCACCTGAAGGAGGATGACGTC |
| AACCTGGCCTCGTCCACGCTGATCAGCGAGGGCAAGT |
| GTCCGTCGGATGCGATGGGTATTGTCATCTCGTACTC |
| GCTGCGCGTCAAGCTCAATTGTGGCACGCTGGTGGCG |
| AACTCCAGACGGACGTACCGTTCAAGCTGATGAACCC |
| AGCACCTGGATCTGTCGAGCGAGAGCGCGTGAACGCC |
| CTGAAGAAGATGAAGTCGATAGAGCGTCACCGTTACG |
| AGAACTCGCACTACGCCGACGATGACGACAACATCGT |
| GTTCGAAGACTTTGCCCGCCTGCGGATGAACGAGCCG |
| GAGTAA |

What is claimed is:

1. A purified polypeptide comprising the amino acid sequence of SEQ ID NO: 25.

2. A purified polypeptide comprising a fragment of at least 40 consecutive amino acids of SEQ ID NO:25.

* * * * *

SEQUENCE LISTING

<160> NUMBER OF SEQ ID NOS: 27

<210> SEQ ID NO 1
<211> LENGTH: 1964
<212> TYPE: DNA
<213> ORGANISM: Anopheles gambiae

<400> SEQUENCE: 1

```
acaggaacga cggttgtgat ccctccactg gtggtgacac gaatcataag cattatttca    60
ytacctaaaaa acaaaatcta caaaaaaaag cttcattccc atcgaaaaaa ctttcttgtg   120
yaaatcaaccg agctaacaaa caacatcctg tgcaaaatct agcagtgaaa gtgtgatatc   180
ytataccctgt acctgtaaac cgttgtgcgc gtgtgtgcct ttgtgtatca attttgtgga   240
yaaacagaaaa tacatcaaaa tggtttacaa tttcaaagtc ttcaagaagt gcgcccctaa   300
ytggaaaggtt acgctgtaca tgggcaagcg tgactttgta gaccacgttt ccggcgttga   360
yaccgatcgat ggtatcgtcg tcctcgatga tgagtacatt cgtgacaacc gtaaggtatt   420
ycggtcagatt gtctgcagtt tccgctacgg ccgcgaagag gacgaggtga tgggactaaa   480
ycttccagaag gagttatgcc tcgcttccga acagatctac ccgcgtccgg aaaagtcgga   540
ycaaggagcag accaagctcc aggagcgact gctgaagaag ctgggttcga acgccatccc   600
```

-continued

```
ygttcacgttc aacatctcgc cgaatgctcc gtcttcggtc acgctgcagc agggcgaaga    660
ytgataatgga gacccgtgcg gtgtgtcgta ctacgtgaag atctttgccg gtgagtcgga    720
yaaccgatcgt acgcaccgtc gcagcaccgt tacgctcggc atacgcaaga tccagttcgc    780
yaccgaccaag cagggccagc agccgtgcac gctggtgcgc aaggacttta tgctaagccc    840
ygggagagctg gagctcgagg tcacactaga caagcagctg tacctgcacg gggagcgaat    900
yaggcgtcaac atctgcatcc gcaacaactc gaacaaaatg gtcaagaaga ttaaggccat    960
ggtccagcag ggtgtggatg tggtgctgtt ccagaatggt agctaccgca acacagtggc   1020
atcgctggag actagcgagg gttgcccaat tcagcccggc tccagtctgc agaaggtaat   1080
gtacctcacg ccgctgctgt cctcgaacaa gcagcgacgt ggcatcgccc tggacggtca   1140
gatcaagcgt caggatcagt gtttggcctc gacaaccctc ttggctcaac cggatcagcg   1200
agatgctttc ggcgttatca tatcgtatgc cgtaaaggtt aagcttttcc tcggcgcact   1260
cggcggcgag ctgtcggcgg aacttccatt tgtgctgatg cacccaaagc ccggcaccaa   1320
ggctaaggtc atccatgccg acagccaggc cgacgtagaa actttccgac aggatacaat   1380
cgaccagcag gcatcagttg actttgaata gacgacgcaa cggtttggaa atgctaccta   1440
ctaccccagg catgggctaa cacgacgaac gaactactac tactaagcat aaaaaacagg   1500
aaaaaaaatg gaaaacttaa aaaatggatc atacaaccga acgcaaacga cctacgacga   1560
tcgatctcac ttccccgtct ttttcatcct aagcaataga acgatggtag aaaaggaaga   1620
taaagatgga gagaaagtca cgtgtatcaa tgacgacgca taccaaaact gaagacgtaa   1680
cacatgttcc ccagcgagcg gtaactgttc tgttctgaca ccttccgctc gacaatgtac   1740
cttttaaaaa catacaaatt agaagtcgtc ttcactacct tcaaccaatc cagccacttt   1800
ggtatatact tttcatagaa tccttctgag cgcaaggacc ctattgaaat tcagtgttat   1860
tttgtaactg cgaccaaatg cctagctgaa tgttgttgaa cgagttatgt acatcaaaag   1920
attgaataaa acaaaaaaaa aaaaaaaaaa aaaaaaaaaa aaaa                    1964
```

<210> SEQ ID NO 2
<211> LENGTH: 383
<212> TYPE: PRT
<213> ORGANISM: Anopheles gambiae

<400> SEQUENCE: 2

```
Met Val Tyr Asn Phe Lys Val Phe Lys Lys Cys Ala Pro Asn Gly Lys
  1               5                  10                  15

Val Thr Leu Tyr Met Gly Lys Arg Asp Phe Val Asp His Val Ser Gly
             20                  25                  30

Val Glu Pro Ile Asp Gly Ile Val Val Leu Asp Asp Glu Tyr Ile Arg
         35                  40                  45

Asp Asn Arg Lys Val Phe Gly Gln Ile Val Cys Ser Phe Arg Tyr Gly
     50                  55                  60

Arg Glu Glu Asp Glu Val Met Gly Leu Asn Phe Gln Lys Glu Leu Cys
 65                  70                  75                  80

Leu Ala Ser Glu Gln Ile Tyr Pro Arg Pro Lys Ser Asp Lys Glu
                 85                  90                  95

Gln Thr Lys Leu Gln Glu Arg Leu Leu Lys Lys Leu Gly Ser Asn Ala
            100                 105                 110

Ile Pro Phe Thr Phe Asn Ile Ser Pro Asn Ala Pro Ser Ser Val Thr
        115                 120                 125

Leu Gln Gln Gly Glu Asp Asp Asn Gly Asp Pro Cys Gly Val Ser Tyr
```

|   |   |   |   |   |   |   |   |   |   |
|---|---|---|---|---|---|---|---|---|---|
| | 130 | | | 135 | | | 140 | | |
| Tyr | Val | Lys | Ile | Phe | Ala | Gly | Glu | Ser | Glu | Thr | Asp | Arg | Thr | His | Arg |
| 145 | | | | 150 | | | | 155 | | | | 160 | | | |

Tyr Val Lys Ile Phe Ala Gly Glu Ser Glu Thr Asp Arg Thr His Arg
145                 150                 155                 160

Arg Ser Thr Val Thr Leu Gly Ile Arg Lys Ile Gln Phe Ala Pro Thr
                165                 170                 175

Lys Gln Gly Gln Gln Pro Cys Thr Leu Val Arg Lys Asp Phe Met Leu
                180                 185                 190

Ser Pro Gly Glu Leu Glu Leu Glu Val Thr Leu Asp Lys Gln Leu Tyr
                195                 200                 205

Leu His Gly Glu Arg Ile Gly Val Asn Ile Cys Ile Arg Asn Asn Ser
210                 215                 220

Asn Lys Met Val Lys Lys Ile Lys Ala Met Val Gln Gln Gly Val Asp
225                 230                 235                 240

Val Val Leu Phe Gln Asn Gly Ser Tyr Arg Asn Thr Val Ala Ser Leu
                245                 250                 255

Glu Thr Ser Glu Gly Cys Pro Ile Gln Pro Gly Ser Ser Leu Gln Lys
                260                 265                 270

Val Met Tyr Leu Thr Pro Leu Leu Ser Ser Asn Lys Gln Arg Arg Gly
                275                 280                 285

Ile Ala Leu Asp Gly Gln Ile Lys Arg Gln Asp Gln Cys Leu Ala Ser
290                 295                 300

Thr Thr Leu Leu Ala Gln Pro Asp Gln Arg Asp Ala Phe Gly Val Ile
305                 310                 315                 320

Ile Ser Tyr Ala Val Lys Val Lys Leu Phe Leu Gly Ala Leu Gly Gly
                325                 330                 335

Glu Leu Ser Ala Glu Leu Pro Phe Val Leu Met His Pro Lys Pro Gly
                340                 345                 350

Thr Lys Ala Lys Val Ile His Ala Asp Ser Gln Ala Asp Val Glu Thr
                355                 360                 365

Phe Arg Gln Asp Thr Ile Asp Gln Gln Ala Ser Val Asp Phe Glu
                370                 375                 380

<210> SEQ ID NO 3
<211> LENGTH: 1239
<212> TYPE: DNA
<213> ORGANISM: Anopheles gambiae

<400> SEQUENCE: 3

```
atgaagctga acaaactgaa cccacggtgg gatgcgtacg atcgacggga ttcgttctgg      60
ttgcagttgc tttgtttgaa atatttaggc ctatggccac cggaagatac ggatcaggca     120
acgcggaacc ggtacatcgc gtacggttgg gctttgcgga tcatgttcct acatctgtac     180
gctctaacgc aagccctata cttcaaggat gtgaaggata ttaatgacat cgcaaatgca     240
ttgttcgtgc ttatgactca agtgacgttg atctacaagc tggaaaagtt taactacaac     300
atcgcacgga ttcaggcttg tctgcgcaag cttaactgca cactgtatca cccgaaacag     360
cgcgaagaat tcagccccgt ttacaatcg atgagtggag tgttttggct gatgatcttt      420
ctcatgtttg tggctatctt caccatcatc atgtgggtta tgtcgccagc cttcgacaat     480
gaacgtcgtc tgcccgtgcc ggcctggttc ccggtggact atcaccattc ggacatagtg     540
tacggtgtac tgttcctgta tcaaaccatt ggaatcgtca tgagcgcaac gtacaacttc     600
tcgaccgata ccatgttttc cggcttgatg ctacacataa atggacaaat tgtgcggctt     660
ggtagtatgg ttaaaaagct tggacatgac gtccctcccg aacgccaatt ggtcgcaacg     720
```

-continued

```
gatgcggaat ggaaagagat gcgaaagcgc atcgaccatc actccaaagt gtacggtacg    780
atgtacgcta aagtaacgga gtgtgtgctg tttcacaagg acatcttaag gatctatctt    840
cgcgcaagta tgcgcgtctg taattatcat ttgtatgaca ctgctgcaac taccgggggc    900
gatgttacga tggccgatct gctgggctgt ggggtctatt tgctagtaaa gacatcgcaa    960
gtgtttattt tctgttacgt agggaatgaa atctcctata cgacggataa atttacagag   1020
tttgttgggt tttccaacta cttcaagttc gataagcgta ccagccaagc aatgatattt   1080
tttctgcaaa tgactcttaa agatgttcac atcaaggtgg aagtgtcttg aaggttacg   1140 ctaaatcttc acacatttttt gcagattatg aagctatcgt actcctatct ggccgtactt   1200
cagagcatgg aatcagagta atggtgttaa tatccttaa                         1239
```

<210> SEQ ID NO 4
<211> LENGTH: 394
<212> TYPE: PRT
<213> ORGANISM: Anopheles gambiae

<400> SEQUENCE: 4

```
Met Lys Lys Asp Ser Phe Phe Lys Met Leu Asn Lys His Arg Trp Ile
 1               5                  10                  15

Leu Cys Leu Trp Pro Pro Glu Asp Thr Asp Gln Ala Thr Arg Asn Arg
            20                  25                  30

Tyr Ile Ala Tyr Gly Trp Ala Leu Arg Ile Met Phe Leu His Leu Tyr
        35                  40                  45

Ala Leu Thr Gln Ala Leu Tyr Phe Lys Asp Val Lys Asp Ile Asn Asp
    50                  55                  60

Ile Ala Asn Ala Leu Phe Val Leu Met Thr Gln Val Thr Leu Ile Tyr
65                  70                  75                  80

Lys Leu Glu Lys Phe Asn Tyr Asn Ile Ala Arg Ile Gln Ala Cys Leu
                85                  90                  95

Arg Lys Leu Asn Cys Thr Leu Tyr His Pro Lys Gln Arg Glu Glu Phe
            100                 105                 110

Ser Pro Val Leu Gln Ser Met Ser Gly Val Phe Trp Leu Met Ile Phe
        115                 120                 125

Leu Met Phe Val Ala Ile Phe Thr Ile Ile Met Trp Val Met Ser Pro
    130                 135                 140

Ala Phe Asp Asn Glu Arg Arg Leu Pro Val Pro Ala Trp Phe Pro Val
145                 150                 155                 160

Asp Tyr His His Ser Asp Ile Val Tyr Gly Val Leu Phe Leu Tyr Gln
                165                 170                 175

Thr Ile Gly Ile Val Met Ser Ala Thr Tyr Asn Phe Ser Thr Asp Thr
            180                 185                 190

Met Phe Ser Gly Leu Met Leu His Ile Asn Gly Gln Ile Val Arg Leu
        195                 200                 205

Gly Ser Met Val Lys Lys Leu Gly His Asp Val Pro Pro Glu Arg Gln
    210                 215                 220

Leu Val Ala Thr Asp Ala Glu Trp Lys Glu Met Arg Lys Arg Ile Asp
225                 230                 235                 240

His His Ser Lys Val Tyr Gly Thr Met Tyr Ala Lys Val Thr Glu Cys
                245                 250                 255

Val Leu Phe His Lys Asp Ile Leu Arg Ile Tyr Leu Arg Ala Ser Met
            260                 265                 270

Arg Val Cys Asn Tyr His Leu Tyr Asp Thr Ala Ala Thr Thr Gly Gly
        275                 280                 285
```

```
Asp Val Thr Met Ala Asp Leu Leu Gly Cys Gly Val Tyr Leu Leu Val
        290                 295                 300

Lys Thr Ser Gln Val Phe Ile Phe Cys Tyr Val Gly Asn Glu Ile Ser
305                 310                 315                 320

Tyr Thr Asp Lys Phe Thr Glu Phe Val Gly Phe Ser Asn Tyr Phe Lys
                325                 330                 335

Phe Asp Lys Arg Thr Ser Gln Ala Met Ile Phe Phe Leu Gln Met Thr
            340                 345                 350

Leu Lys Asp Val His Ile Lys Val Gly Ser Val Leu Lys Val Thr Leu
                355                 360                 365

Asn Leu His Thr Phe Leu Gln Ile Met Lys Leu Ser Tyr Ser Tyr Leu
        370                 375                 380

Ala Val Leu Gln Ser Met Glu Ser Glu Glx
385                 390
```

<210> SEQ ID NO 5
<211> LENGTH: 1142
<212> TYPE: DNA
<213> ORGANISM: Anopheles gambiae

<400> SEQUENCE: 5

```
atgctgatcg aagagtgtcc gataattggt gtcaatgtgc gagtgtggct gttctggtcg    60
tatctgcggc ggccgcggtt gtcccgcttt ctggtcggct gcatcccggt cgccgtgctg   120
aacgttttcc agttcctgaa gctgtactcg tcctggggcg acatgagcga gctcatcatc   180
aacggatact ttaccgtgct gtactttaac ctcgtcctcc gaacctcctt tctcgtgatc   240
aatcgacgga aatttgagac attttttgaa ggcgttgccg ccgagtacgc tctcctcgag   300
aaaaatgacg acatccgacc cgtgctggag cggtacacac ggcggggacg catgctatcg   360
atatcgaatc tgtggctcgg cgccttcatt agtgcctgct tgtgacccta tcctctgttt   420
gtgcccgggc gcggcctacc gtacggcgtc acgataccgg gcgtggacgt gctggccacc   480
ccgacctacc aggtcgtgtt tgtgctgcag gtttaccta ccttccccgc ctgctgcatg   540
tacatcccgt tcaccagctt ctacgcgacc tgcacgctgt ttgcgctcgt ccagatagcg   600
gccctaaagc aacggctcgg acgcttgggg cgccacagcg gcacgatggc ttcgaccgga   660
cacagcgccg gcacactgtt cgccgagctg aaggagtgtc taaagtatca caaacaaatc   720
atccaatatg ttcatgatct caactcactc gtcacccatc tgtgtctgct ggagttcctg   780
tcgttcggga tgatgctgtg cgcactgctg tttctgctaa gcattagcaa tcagctggca   840
cagatgataa tgattggatc gtacatcttc atgatactct cgcagatgtt tgccttctat   900
tggcatgcga acgaggtact ggagcagagc ctaggcattg gcgatgccat ttacaatgga   960
gcgtggccgg actttgagga accgataagg aaacggttga ttctaattat tgcacgtgct  1020
cagcgaccga tggtggtaag attaaagtcg gcaacgtgta cccgatgacg ttggaaatgt  1080
ttcaaaaatt gctcaacgtg tcctactcct atttcacact gctgcgccga gtgtacaact  1140
aa                                                                  1142
```

<210> SEQ ID NO 6
<211> LENGTH: 380
<212> TYPE: PRT
<213> ORGANISM: Anopheles gambiae

<400> SEQUENCE: 6

Met Leu Ile Glu Glu Cys Pro Ile Ile Gly Val Asn Val Arg Val Trp

```
              1               5              10              15
Leu Phe Trp Ser Tyr Leu Arg Arg Pro Arg Leu Ser Arg Phe Leu Val
                 20                  25                  30

Gly Cys Ile Pro Val Ala Val Leu Asn Val Phe Gln Phe Leu Lys Leu
                 35                  40                  45

Tyr Ser Ser Trp Gly Asp Met Ser Glu Leu Ile Ile Asn Gly Tyr Phe
                 50                  55                  60

Thr Val Leu Tyr Phe Asn Leu Val Leu Arg Thr Ser Phe Leu Val Ile
 65                  70                  75                  80

Asn Arg Arg Lys Phe Glu Thr Phe Phe Glu Gly Val Ala Ala Glu Tyr
                 85                  90                  95

Ala Leu Leu Glu Lys Asn Asp Asp Ile Arg Pro Val Leu Glu Arg Tyr
                100                 105                 110

Thr Arg Arg Gly Arg Met Leu Ser Ile Ser Asn Leu Trp Leu Gly Ala
                115                 120                 125

Phe Ile Ser Ala Cys Phe Val Thr Tyr Pro Leu Phe Val Pro Gly Arg
                130                 135                 140

Gly Leu Pro Tyr Gly Val Thr Ile Pro Gly Val Asp Val Leu Ala Thr
145                 150                 155                 160

Pro Thr Tyr Gln Val Val Phe Val Leu Gln Val Tyr Leu Thr Phe Pro
                165                 170                 175

Ala Cys Cys Met Tyr Ile Pro Phe Thr Ser Phe Tyr Ala Thr Cys Thr
                180                 185                 190

Leu Phe Ala Leu Val Gln Ile Ala Ala Leu Lys Gln Arg Leu Gly Arg
                195                 200                 205

Leu Gly Arg His Ser Gly Thr Met Ala Ser Thr Gly His Ser Ala Gly
                210                 215                 220

Thr Leu Phe Ala Glu Leu Lys Glu Cys Leu Lys Tyr His Lys Gln Ile
225                 230                 235                 240

Ile Gln Tyr Val His Asp Leu Asn Ser Leu Val Thr His Leu Cys Leu
                245                 250                 255

Leu Glu Phe Leu Ser Phe Gly Met Met Leu Cys Ala Leu Leu Phe Leu
                260                 265                 270

Leu Ser Ile Ser Asn Gln Leu Ala Gln Met Ile Met Ile Gly Ser Tyr
                275                 280                 285

Ile Phe Met Ile Leu Ser Gln Met Phe Ala Phe Tyr Trp His Ala Asn
                290                 295                 300

Glu Val Leu Glu Ala Ser Leu Gly Ile Gly Asp Ala Ile Tyr Asn Gly
305                 310                 315                 320

Ala Trp Pro Asp Phe Glu Glu Pro Ile Arg Lys Arg Leu Ile Leu Ile
                325                 330                 335

Ile Ala Arg Ala Gln Pro Thr Asp Gly Gly Lys Ile Lys Val Gly Asn
                340                 345                 350

Val Tyr Pro Met Thr Leu Glu Met Phe Gln Lys Leu Leu Asn Val Ser
                355                 360                 365

Tyr Ser Tyr Phe Thr Leu Leu Arg Arg Val Tyr Asn
                370                 375                 380

<210> SEQ ID NO 7
<211> LENGTH: 1236
<212> TYPE: DNA
<213> ORGANISM: Anopheles gambiae

<400> SEQUENCE: 7
```

-continued

```
atgccttctg agcggcttcg tctcattact tccttcggaa ctcctcaaga caaacgcacg      60
atggtactgc caaaattaaa ggatgaaaca gcagtgatgc cgtttctgct gcaaattcaa     120
accattgccg gactgtgggg tgaccgttcc cagcggtacc gttttatct catcttttcc      180 tacttctgcg cgatggtggt tctacccaaa gtgctgttcg ttatccaga tctcgaggtt     240 gcggtacgcg gcacggccga gctgatgttc aatcgaacg cattcttcgg catgctaatg     300
ttttcctttc aacgcgacaa ctacgagcga ttggtgcatc agctgcagga tctggcagct     360
ctagtcctcc aagacctacc cacagagctg ggagagtacc tgatctcagt gaaccgacgg    420
gtcgatcggt tctccaaaat ttactgctgc tgtcactttt ccatggcaac gttcttttgg    480
ttcatgcccg tctggacgac ctattccgcc tactttgctg tgcgcaacag cacggaaccg    540
gtcgagcacg tgttgcacct cgaggaagag ctgtacttcc tgaacattcg gacttcgatg    600
gcgcactata cgttttatgt ggccattatg tggcccacga tctatacgct cgggtttacc    660
ggtggcacaa agctgctgac cattttcagc aatgttaagt actgttcggc catgctgaag    720
ctcgttgcac tccgaatcca ctgtctagcg agagtagcgc aagaccgagc ggaaaaggag    780
ctgaacgaga tatttccat gcatcagcgg gtactcaact gcgtgttcct gctggagacg     840
acattccgct gggtattttt cgtgcagttc attcagtgta caatgatctg gtgcagtctc    900
atcctctaca tagcggtgac ggggttcagc tcgacggtag cgaatgtatg tgtccagatc    960
attttggtga cggtggaaac ttacggctac ggctacttcg aacagatct aaccacggag    1020 gtgctttgga gctatggcgt tgccctcgcc atttacgata cgagtggta caagttttcc    1080 atttcgatgc gccgcaaact tcgactgcta ctgcaacgat cccaaaaacc gctcggcgta    1140
acggcgggaa agtttcgctt cgtcaatgtg gcccagtttg gcaagatgct caagatgtcc    1200
tattcatttt acgtagtact gaaggagcag ttttag                               1236
```

<210> SEQ ID NO 8
<211> LENGTH: 411
<212> TYPE: PRT
<213> ORGANISM: Anopheles gambiae

<400> SEQUENCE: 8

```
Met Pro Ser Glu Arg Leu Arg Leu Ile Thr Ser Phe Gly Thr Pro Gln
  1               5                  10                  15

Asp Lys Arg Thr Met Val Leu Pro Lys Leu Lys Asp Glu Thr Ala Val
                20                  25                  30

Met Pro Phe Leu Leu Gln Ile Gln Thr Ile Ala Gly Leu Trp Gly Asp
            35                  40                  45

Arg Ser Gln Arg Tyr Arg Phe Tyr Leu Ile Phe Ser Tyr Phe Cys Ala
        50                  55                  60

Met Val Val Leu Pro Lys Val Leu Phe Gly Tyr Pro Asp Leu Glu Val
 65                  70                  75                  80

Ala Val Arg Gly Thr Ala Glu Leu Met Phe Glu Ser Asn Ala Phe Phe
                85                  90                  95

Gly Met Leu Met Phe Ser Phe Gln Arg Asp Asn Tyr Glu Arg Leu Val
            100                 105                 110

His Gln Leu Gln Asp Leu Ala Ala Leu Val Leu Gln Asp Leu Pro Thr
        115                 120                 125

Glu Leu Gly Glu Tyr Leu Ile Ser Val Asn Arg Arg Val Asp Arg Phe
    130                 135                 140

Ser Lys Ile Tyr Cys Cys Cys His Phe Ser Met Ala Thr Phe Phe Trp
145                 150                 155                 160
```

Phe Met Pro Val Trp Thr Thr Tyr Ser Ala Tyr Phe Ala Val Arg Asn
                165                 170                 175

Ser Thr Glu Pro Val Glu His Val Leu His Leu Glu Glu Leu Tyr
            180                 185                 190

Phe Leu Asn Ile Arg Thr Ser Met Ala His Tyr Thr Phe Tyr Val Ala
            195                 200                 205

Ile Met Trp Pro Thr Ile Tyr Thr Leu Gly Phe Thr Gly Thr Lys
    210                 215                 220

Leu Leu Thr Ile Phe Ser Asn Val Lys Tyr Cys Ser Ala Met Leu Lys
225                 230                 235                 240

Leu Val Ala Leu Arg Ile His Cys Leu Ala Arg Val Ala Gln Asp Arg
                245                 250                 255

Ala Glu Lys Glu Leu Asn Glu Ile Ile Ser Met His Gln Arg Val Leu
            260                 265                 270

Asn Cys Val Phe Leu Leu Glu Thr Thr Phe Arg Trp Val Phe Phe Val
            275                 280                 285

Gln Phe Ile Gln Cys Thr Met Ile Trp Cys Ser Leu Ile Leu Tyr Ile
    290                 295                 300

Ala Val Thr Gly Phe Ser Ser Thr Val Ala Asn Val Cys Val Gln Ile
305                 310                 315                 320

Ile Leu Val Thr Val Glu Thr Tyr Gly Tyr Gly Tyr Phe Gly Thr Asp
                325                 330                 335

Leu Thr Thr Glu Val Leu Trp Ser Tyr Gly Val Ala Leu Ala Ile Tyr
            340                 345                 350

Asp Ser Glu Trp Tyr Lys Phe Ser Ile Ser Met Arg Arg Lys Leu Arg
            355                 360                 365

Leu Leu Leu Gln Arg Ser Gln Lys Pro Leu Gly Val Thr Ala Gly Lys
    370                 375                 380

Phe Arg Phe Val Asn Val Ala Gln Phe Gly Lys Met Leu Lys Met Ser
385                 390                 395                 400

Tyr Ser Phe Tyr Val Val Leu Lys Glu Gln Phe
                405                 410

<210> SEQ ID NO 9
<211> LENGTH: 3895
<212> TYPE: DNA
<213> ORGANISM: Anopheles gambiae

<400> SEQUENCE: 9
agctttgttc atttatgttg aaatctagcc cattttgtat agtgctgaac gacgaagaac      60
atacgaaagt acctcgtccg aacactatca acattaatta taccaagcta gaagaagata     120
tttatagtca agcctcaaca tcataggaaa ctttagcaaa accatttaat ttacatgatg     180
ataagtccca cctcttaccc cagcacaggt tgagaagga cgaaagtatc tttacgataa      240
tattactcta aggtagtttt tgaataaaat aaaaatttac gtgcaagtgg tggcatcgga     300
catcattcga aagaatctac taagtcatac acacacccaa gacgaccgac gtagtttcat     360
ctagaaaaaa cgggtcagct ccatcgaaca cgtcaggaca taactgcgac atgcgtatgg     420
tcagttccac tagtgccaac actggttcca gggcactacc ttccgaagca gtagaaccta     480
atgtattgga aattattagg acatactgca acatgcatat ggctagttcc gctggtacca     540
acgatggcac caggacacta tctgcggcct tgtaaaatca ctgtaaaatc tatacaaaaa     600
cggctttacc catactttat cacaaaaacg gcaggtgagg gctggattgc ttcaaagcat     660

-continued

| | | |
|---|---|---|
| tagaaatata taatttcaaa gtccataatc tccttaaaag atagacaaca gtagagaaca | 720 |
| catttagtgc tcttttcgtt cgagttagtt gccttctcaa gtaagcgttt aatgctcaat | 780 |
| tgttgtagat tcgttggatg actctcgcta cgtgctatag tggtcaatac ttccaattag | 840 |
| atttcataat tagtttccaa ttgtccacgg aaaacccaca aaagaaaaaa aaacttgtat | 900 |
| ctagggtgga attttcgag aacaattgga cacttcatat gaaaaaggac agctttttca | 960 |
| aaatgttaaa taaacaccgt tggatccttt gttggatttc aattctccaa attctgcaga | 1020 |
| ataattctgc aaattttaca aaactgctca accaccaata attccaatta atcatctgaa | 1080 |
| catttaaaac tgataattaa gatgagtaat tgcttcgtca tcacctaaga aatcgattag | 1140 |
| tttggataaa aagaacaaat tgaaatacaa taaagtccct gaattttatt cgaataacgg | 1200 |
| cttgaactca tttatttcaa aaacctttga gaaattcctc gttgaaaatt ggtctcctat | 1260 |
| agttctgcta acgggccact tcaaaagcaa gaactaacaa aatcataatt atggtgcaag | 1320 |
| taactatcag taccagtaat cgccattaaa aacttttcct caatttgcgg ctcgttaccg | 1380 |
| gctaaataca gagcagagta acgggaagtg atcaacgtcg ctattagtat aacgaggaac | 1440 |
| gccctccgaa ggtgtgttga aggaccttt caaattgaaa ccaagtactg tttccagttt | 1500 |
| taaattggat agttataaaa tgagccgttc aacgatcggg catcatttga gtttcatctt | 1560 |
| cgaggagaaa tagatcagtg ccactgttta accgaaagta atgaagctga acaaactgaa | 1620 |
| cccacggtgg gatgcgtacg atcgacggga ttcgttctgg ttgcagttgc tttgtttgaa | 1680 |
| atatttaggc ctatggccac cggaagatac ggatcaggca acgcggaacc ggtacatcgc | 1740 |
| gtacggttgg gcttttgcgga tcatgttttct acatctgtac gctctaacgc aagccctata | 1800 |
| cttcaaggat gtgaaggata ttaatgtgag tctctagtta gctattagtg ttccacctgt | 1860 |
| ccataatctg tcttttattg ggtaggacat cgcaaatgca ttgttcgtgc ttatgactca | 1920 |
| agtgacgttg atctacaagc tggaaaagtt taactacaac atcgcacgga ttcaggcttg | 1980 |
| tctgcgcaag cttaactgca cactgtatca cccgaaacag cgcgaagaat tcaggtaagc | 2040 |
| ctgctgggaa atatgactaa aaagagtgct aacaaacgac tctcctccaa atgtagcccc | 2100 |
| gttttacaat cgatgagtgg agtgtttgg ctgatgatct ttctcatgtt tgtggctatc | 2160 |
| ttcaccatca tcatgtgggt tatgtcgcca gccttcgaca atgaacgtcg tctgcccgtg | 2220 |
| ccggcctggt tcccggtgga ctatcaccat tcggacatag tgtacggtgt actgttcctg | 2280 |
| tatcaaacca ttggaatcgt catgagcgca acgtacaact tctcgaccga taccatgttt | 2340 |
| tccggcttga tgctacacat aaatggacaa attgtgcggc ttggtagtat ggttaaaaag | 2400 |
| gtgagttacg gcgactactt gcctccagta aggacaggga gtttgtttcc gttatgatat | 2460 |
| cattttatca gcttggacat gacgtccctc ccgaacgcca attggtcgca acggatgcgg | 2520 |
| aatggaaaga gatgcgaaag cgcatcgacc atcactccaa agtgtacggt acgatgtacg | 2580 |
| ctaaagtaac ggagtgtgtg ctgtttcaca aggacatctt aaggtacgaa ttgggccaat | 2640 |
| taattgtgtc atttaaaaag cttgacccaa cttttcacag cttcggcgat gaagtgcagg | 2700 |
| acattttcca aggatctatc ttcgcgcaag tatgcgcgtc tgtaattatc atttgtatga | 2760 |
| cactgctgca actaccgggg gcgatgttac gatggccgat ctgctgggct gtgggtcta | 2820 |
| tttgctagta aagacatcgc aagtgtttat tttctgttac gtagggaatg aaatctccta | 2880 |
| tacggtaggt tggacacgta gaggaattaa atgtttggga agaatatcaa taccaaatag | 2940 |
| tatgatgttt cgttcagac ggataaattt acagagtttg ttgggttttc caactacttc | 3000 |
| aagttcgata agcgtaccag ccaagcaatg atattttttc tgcaaatgtg agatagcggt | 3060 |

-continued

```
gtatttgtgc agtcagtaca ttaaatacgt tctctatttc aggactctta aagatgttca    3120
catcaaggtg ggaagtgtct tgaaggttac gctaaatctt cacacatttt tgcaggtatg    3180
taattatgct gtggtattta gcttgaaata agctacaaac tttgaaagta atttcaatct    3240
gttttgtaga ttatgaagct atcgtactcc tatctggccg tacttcagag catggaatca    3300
gagtaatggt gttaatatcc ttaatgttga aattatattt tgttagattt attgcataaa    3360
gtaatattta attttataca tcaaacgtaa gcccgctagt tttcaattag ccttttccaa    3420
aatttatcaa attgatttcg aattgattgc agagtttcag gaatttaatc tgataggata    3480
tcttgtttat ccaatagagg tgtggaagcg ttcccaagcc attcgtttga tagtttatag    3540
caccgtcgag cagttgatcg ctgtgatcgc taggcgcacc tgattttatc tttatctcgc    3600
acctgttatg gcaagggcgc ttttcacacg tttcacacaa tataatgcac atgtataatg    3660
cattcttact ttagcatttt tgttacatat aataccaaaa ttatgcattt ttattctcac    3720
gcaacgatta gaggatgact tcacaaaggt ccatctagtg gtaggaggta tacaattata    3780
cctctcaaaa tctcacagca taatgagaaa caaaaggata ccaagcatac cctttttta    3840 cttgacaatt tcatttgatt tatgtaataa agcactgcac gtcgacttcc taaaa        3895
```

<210> SEQ ID NO 10
<211> LENGTH: 4985
<212> TYPE: DNA
<213> ORGANISM: Anopheles gambiae

<400> SEQUENCE: 10

```
gggatcctct agagtcgacc tgcaggcatg caagcttccc tcaccgtgac gtgctagaaa      60
tggttcaaca tactcgtccg gcagagcgaa gacgacgaac agcggaatgt cccaggaaat     120
gtaatgagat atcacagcaa gtgaacccaa accgagctgt gcgctttgtg ttgcgcttta     180
aaaatggccc ttccttcgcc gcatctgctt ggtttcacac gctttcccag gaaatccact     240
gaccactggc cacacatcaa ccaccggagc gggagcctca gtgcccagcg aagcatataa     300
tttgctcaaa aagtcacggt actcaattaa tttgattata tcaatttcg tggcttccaa      360 cacacccttc ttccacaatc catcgccgag tgagcgagta taaggtgaa gaaacgtacc      420 ttgcgcttgc tcactaactg aaccggattt caaaaggaa cataaaccgc aacccacagc      480
cgaaaatgct gatcgaagag tgtccgataa ttggtgtcaa tgtgcgagtg tggctgttct     540
ggtcgtatct gcggcggccg cggttgtccc gctttctggt cggctgcatc ccggtcgccg     600
tgctgaacgt tttccagttc ctgaagctgt actcgtcctg gggcgacatg agcgagctca     660
tcatcaacgg atactttacc gtgctgtact ttaacctcgt cgtacgtggg cgaggggagg     720
ggcaataacc ttcccacttg gtggatattt tcatacctt tccatgtgtt ttttattct      780 ctgtttgttg ccatccagct ccgaacctcc tttctcgtga tcaatcgacg gaaatttgag    840 acatttttg aaggcgttgc cgccgagtac gctctcctcg aggtaagtca ttggttttc      900 tagttttgg gggagttgtt tacaccataa ccacccccga cggtaacatt tgatcgtccc     960
gcgaaaatgt ttgtacagaa aaatgacgac atccgacccg tgctggagcg gtacacacgg   1020
cggggacgca tgctatcgat atcgaatctg tggctcggcg ccttcattag tgcctgcttt   1080
gtgacctatc ctctgtttgt gcccgggcgc ggcctaccgt acggcgtcac gataccgggc   1140
gtggacgtgc tggccacccc gacctaccag gtcgtgtttg tgctgcaggt ttaccttacc   1200
ttccccgcct gctgcatgta catcccgttc accagcttct acgcgacctg cacgctgttt   1260
```

-continued

```
gcgctcgtcc agatagcggc cctaaagcaa cggctcggac gcttggggcg ccacagcggc      1320
acgatggctt cgaccggaca cagcgccggc acactgttcg ccgagctgaa ggagtgtcta      1380
aagtatcaca aacaaatcat ccagtaagta gacgctagta gactcgaccg gattgccctt      1440
ccctcgggga ggggaggttt gctatttcgg gatgcggcag cacgcataca cacaaaccgg      1500
aagccattaa ttctcccgtt ttcatgcccg cacgggcact gggtcatgtt tcacatcctt      1560
ccttcctttc caaacacaca cacgcgcgcg tgcacgtaca gatatgttca tgatctcaac      1620
tcactcgtca cccatctgtg tctgctggag ttcctgtcgt tcgggatgat gctgtgcgca      1680
ctgctgtttc tgctaagcat tgtaagtaaa atcgaccgac gtgcggtcgc tagtccgtct      1740
ccggactctc atttcgggac tcaatcgttc catctctcaa tagagcaatc agctggcaca      1800
gatgataatg attggatcgt acatcttcat gatactctcg cagatgtttg ccttctattg      1860
gcatgcgaac gaggtactgg agcaggtaat ggcgctgaag ctgagtttgg ttgagcggtt      1920
cgctatagat cggctgtctt acattgttgt gtttctgcat ggggatcggt tttgtttttc      1980
ctctccattt cagagcctag gcattggcga tgccatttac aatggagcgt ggccggactt      2040
tgaggaaccg ataaggaaac ggttgattct aattattgca cgtgctcagc gaccgatggt      2100
ggtaagtttg gctgatcgat gctctgttca atgaacatgg cacagaaggc tgtgtaaata      2160
gctgttcatt aataagtttt tcagaatgt atcgttttta gttgatttaa acgcattgtt      2220
ctatgcaatg gtagcaacaa tagaccgcct ttattaatcc aagcttcctt taggattgat      2280
ttttatttta agagaaagat aaaccatttt tagtaaccaa tttagttaca ggaaccaaaa      2340
tacagaattt attattatta ttattattat tattattatt attattatta ttattattat      2400
tattattatt attattatta ttattattat tattataatt attattatta ttattattat      2460
tattattatt attattatta atattattat tattattatt attattacta ttattattat      2520
aattattact tttattatta ttattattat tattattatt attattatta ttattattat      2580
tattattatt attataatta tgattattat tattattatt attattatta ttattattat      2640
aacaataata attattatta ttatttatta ttaattaatt aatttattat tattaattat      2700
tattattgtt attcattatt atacattatt atcataataa taattttatt atgattatta      2760
ttattattat tattattatt attattatta ttattattat tcttattatt attattatta      2820
ttattattat taatattatt tttaatatta ttattattat tattactatt cttattataa      2880 ttatttttt ttattattat tattattatt attattatta ttattattat tattattatt      2940
gctattgtta ttattattct tattattgct attgttatta ttattattct tattattgtt      3000
gttgttgttg ttcttattat tgttgttgtt gttattctta ttattgttta ttattattgt      3060 tttttttat tctctaatta ttccagtaat ccataataaa aataataaa gtaaataaat      3120 agtaaatagt aaataattcc agtaactgta gtaatacaca ataatctcta agaattaaaa      3180
ttgcattttg taatgaaata tgttgattgt tcgaatagtt cagaaaaact taaaaatgcc      3240
tcagcattaa acagttttga ggttgttcag ggcatttagt ttagatattt tagtatttta      3300
aagcatttgt tttcattact acaaaaaagc aaatttatga gtgaattact ttcagttctt      3360
ctaaacgcct atgtgtatgc aattacataa caatagctct ctttttttatt gcattttttcc      3420 ttagtaatct aaatccaatc tcttcttttcc ctcttgcaga ttaaagtcgg caacgtgtac      3480
ccgatgacgt tggaaatgtt tcaaaaattg ctcaacgtgt cctactccta tttcacactg      3540
ctgcgccgag tgtacaacta aacttaaccg gtaaacaaac aaaaatcccc tcatcactat      3600
gcaaagacag caagcagccg atcatcaaac accattagca gccacaaagt taccagccgc      3660
```

```
ttatcccacg ggatttggtg gaaagttatt gcactgaagc tctttcaccc aaattttcat    3720
ggaggttccc tctcaaccaa cccattgaag cgaataaaag tatcagcaac caggcgacgg    3780
tgaaaaaacg ctgcattatt gtgcttgctt cagcattcca gcgaatgact cttaaacttt    3840
tccattcaaa agtcgcgatg ctcacgatac ggagcggtgt gttgttcgat ccgccgagtg    3900
cactcgcaag ccggtgatgt tgccggtgga aatgcacaga tcgacacagc gatagataat    3960
cgtttgttcg cgtaaatggg agggaaaaaa gtaagctgcc agctacttca tttccatgtt    4020
aattgaaact caagccaacg aacatgcaga acccggttgg ttgtgtgtct ccgctccggg    4080
aaaggtctct gctccggggc atggattctt tccccctccg ggtggttggg ggtattgttt    4140
aggtttttat tttacaaatt catatccttc cgcttccgca tcagccgacc cggtgggtgc    4200
gccagacaga tgtgcggcgg gcaacaaaac tatgcacgaa catggccaac aaacacagct    4260
tctatctcat ctctgtgtcg cactgtctcg ctttcccgct gcgttgcttg tagtactatc    4320
attgttttag tccacgggtt tacttctaat tccattgcac cacgcaaaaa ggctcatcct    4380
ttgctcgttc cggttgcaac ttcgacaagc gcatggttgg gatacgaaca aaaaccaac    4440 tactccaccc actactacta ctactgccac caccactaac aacactacac ttggttggga    4500
gcttgcagac ccacaagcaa acaacgatac aagctagcta gctgctgtgt gcgctcgagt    4560
cagccgacgg tacaaggttt aaccggtaca agcaactccc ggaccgatcc caaaactctg    4620
acaaggcacg gggccgcatc cggcagtacg gtcggaaaac atggaaatgt ttaattaaaa    4680
ctgtaattgt caatcgctgc tacaagttgt gacacaggga gagagagaga cagagcgcgc    4740
ccgatggtga tggtgtaaaa gatagataca ggaaaagagc gagaaacatt ggtacgattt    4800
ggtgtggtta gcaaatttga tttccactga ttttgagtgc aaatttaatg catcgaaaat    4860
ttgccattca gggtaaagtt gctcgtggac ggatcccccg ggctgcagga attcgatatc    4920
aagcttatcg ataccgtcga cctcgagggg gggcccggta cccagctttt gttcccttta    4980
gtgga                                                                4985

<210> SEQ ID NO 11
<211> LENGTH: 2083
<212> TYPE: DNA
<213> ORGANISM: Anopheles gambiae

<400> SEQUENCE: 11
aagcagaaca catcaagaag caattaggtg tgtcgtacgt tagcaagtag ttcgcgagga      60
ggaataaaat agatgccttc tgagcggctt cgtctcatta cttccttcgg aactcctcaa     120
gacaaacgca cgatggtact gccaaaatta aaggatgaaa cagcagtgat gccgtttctg     180
ctgcaaattc aaaccattgc cggactgtgg ggtgaccgtt cccagcggta ccgtttttat     240
ctcatctttt cctacttctg cgcgatggtg gttctaccca aagtgctgtt cggttatcca     300
gatctcgagg ttgcggtacg cggcacggcc gagctgatgt tcgaatcgaa cgcattcttc     360
ggcatgctaa tgttttcctt tcaacgcgac aactacgagc gattggtgca tcagctgcag     420
gatctggcag ctctaggtga gtatgcagcc aatcgattgt tccaaacctt cgcaacatcc     480
ttcgtaacac tgctacactt tcagtcctcc aagacctacc cacagagctg ggagagtacc     540
tgatctcagt gaaccgacgg gtcgatcggt tctccaaaat ttactgctgc tgtcactttt     600
ccatggcaac gttctttggg ttcatgcccg tctggacgac ctattccgcc tactttgctg     660
tgcgcaacag cacggaaccg gtcgagcacg tgttgcacct cgaggaagag ctgtacttcc     720
```

-continued

```
tgaacattcg gacttcgatg gcgcactata cgttttatgt ggccattatg tggcccacga        780
tctatacgct cgggtttacc ggtggcacaa agctgctgac cattttcagc aatgttaagt        840
actgttcggc catgctgaag ctcgttgcac tccgaatcca ctgtctagcg agagtagcgc        900
aagaccgagc ggaaaaggag ctgaacgaga ttatttccat gcatcagcgg gtactcaagt        960
aagtaaattc aaattgaaag ttttgcaggg aataacttga gtgtgtctga cccgtgcaca       1020
tcctagctgc gtgttcctgc tggagacgac attccgctgg gtattttcg tgcagttcat        1080
tcagtgtaca atgatctggt gcagtctcat cctctacata gcggtgacgg taatagcatt       1140
ttcgtcattt cgttagcctt attcaatcca tttttgtgaa cgtgaatttc ccccaggggt       1200
tcagctcgac ggtagcgaat gtatgtgtcc agatcatttt ggtgacggtg gaaacttacg       1260
gctacggcta cttcggaaca gatctaacca cggaggtgct ttgggtaccc tttgatgaa        1320
gcttcaaaaa gtaattccaa attctgtttt cgattttcc ccttttccac tagagctatg        1380
gcgttgccct cgccatttac gatagcgagt ggtacaagtt ttccatttcg atgcgccgca       1440
aacttcgact gctactgcaa cgatcccaaa aaccgctcgg cgtaacggcg ggaaagtttc       1500
gcttcgtcaa tgtggcccag tttggcaagg taacattaat tacagtttga aaattctgaa       1560
gaatgcatct tacttgcctt acttgttgtt ccagatgctc aagatgtcct attcatttta       1620
cgtagtactg aaggagcagt tttaggagct gctgtttccc accctggaaa tggccttttc       1680
gcactgtctt ctgtttgttg gacgcacgca gcaccgagag cgcccctgca cgcactgacg       1740
tattttggct acttttgacgt ttgcaccttt gacagctgaa ggacagggta caattttttgc      1800
tgctgttatt acgcgcagcg cattggatac gaaaacattg gccacaagtt ctacgatttt       1860
agcgtttatt tactgttcgt agcagctttt ttccacaata aacacacaca ataacgtacc       1920
gacagtattc tttttcattgt aggatagaga agccgccggc cagcagccaa aacgcgccgc      1980
aaaacgaaag gcggcaccac cggggggaaaa acacgggagc aaaacgagaa cagaacgcag      2040
taaacaacaa aaccggccgg aacaacaacg gtgccggaaa cga                        2083
```

<210> SEQ ID NO 12
<211> LENGTH: 2374
<212> TYPE: DNA
<213> ORGANISM: Anopheles gambiae

<400> SEQUENCE: 12

```
ggggaactcc cccacccgac cagacgacgg aaagctaacg atgtgcaatt gaatagtcat         60
tagtagcgtt tttgctcgca aacgaactaa cccctttgact ttttaagttc actacggtga       120
ggacaaaaat caataaatta aatcgagacc gttgatgagc aaaagaaaaa aaatatttt         180
actgattttc atttcgttcc atcgactaca taatcataat tatatgccac attttattat        240
aagttttttgt atcattttta aacaacacaa aaatgcatcc tttcgaatat tagtcaggtt       300
gtatcaacaa tgaagtttga actgtttcaa aaatattcct ccccggacac ggtcttatcc       360
ttcgtgctaa ggcttttgca tatcgtgggc atgaatgggg caggatttcg gtcgcgaatt       420
cgagttggtg gcatttttct gttctattta atctttcttg taataccgcc actaacgggc       480
gggtacaccg atggtcacca gcgtgtacgc accagtgtgg aattcctgtt taattgcaat       540
atttacggcg gcagtatgtt ctttgcctac gatgtggcca cttttccaagc gttcatccag       600
gaactgaaga gccttttcggt tttgggtaat atttaattaa ttaaaattgc gtttattgca       660
tcatcatttg tttctctttg cagtatgctc acattcgtac agactaaagt ataagctgac       720
ccggttcaac cgtcgagcgg atattatcgc caaagtgcaa acgacctgca tgggtgctgt       780
```

| | |
|---|---|
| aacgcttttc tactggattg caccgatacc ttccatctgt gcgcactact acaggtcgac | 840 |
| caattccacc gaacccgtgc ggtttgtgca acatttagag gtgaagttct attggctcga | 900 |
| gaatcgcacc tcagtcgagg actacataac cttcgtgctg atcatgctac ccgtcgtggt | 960 |
| tatgtgtggt tacgtatgca atttgaaggt gatgaccatc tgctgcagca ttggacactg | 1020 |
| tacactgtac accaggatga ctatagagat ggtagagcag ttggaaagca tggcatcagc | 1080 |
| ggaacgaact gccagcgcca tacgcaacgt ggggcagatg cacagtggtt tactgaaatg | 1140 |
| cattaggctt ttgaacacgt caatccgatc gatgctgatg ctgcagtggt tgacctgcgt | 1200 |
| gttaaactgg agcatttctc tcatctatct aacgaacgtg gttagttttg tcttgtttgg | 1260 |
| aaatccaaaa acaaaaagat ggctataatt gaactttcta ttacagggca tctcgctaca | 1320 |
| atcggttacc gtggtggtaa tgttttttct tgccactgcg gaaactttcc tgtattgttt | 1380 |
| acttgggacg cggcttgcga cacaacagca gctgctggag cacgcactct atgctacacg | 1440 |
| gtggtacaac tacccaatag cctttcgcag cagcattagg atgatgttga gacagtcgca | 1500 |
| aaggcatgca cacataacgg tggggaagtt ttttcgcgtt aatttggaag aatttagcag | 1560 |
| gattgtcaac ttatcctact ctgcttacgt cgtacttaag gatgtaataa agatggatgt | 1620 |
| acagtgaatg ttttttttt tggcttggca acgaatgaag ttttccgaat ctatattaga | 1680 |
| tctagaattt aatctagatg tcataatatg atcttggcca tgaccggttc ctggttttgg | 1740 |
| aaccaattct caaaacaatt ttgaacttag ggcgaggcat gaaatgtccc aagaacctat | 1800 |
| ccaagttctg gaactacata ttaccgaatc tatcccatta ttgcctcgga actggttttgg | 1860 |
| tgctaaatat ttgtccaaat gttggtcctg gacctatcca gacaaagatc ttcaattatt | 1920 |
| cctaccactg gaactgatta ttgatgtag gaagtcatgg aggtgttcag ggagaattta | 1980 |
| aacactaatg ttccaactca ttatttcaag ggcaattcta tttttttatat gcccctacgg | 2040 |
| attgatacgt atgtattact ccatttcctg gactttgtct tattcttgct gctgattgga | 2100 |
| cgtgaaatgt tgagaaaaag attcttattt atgagtgata cagagccttt aaatactcct | 2160 |
| acgttgtttg ctatttaagt atggccaggc taatcacaat cgctactaat gaacagaatc | 2220 |
| tcttctaatt aaacccttc gattgatagt gtcaatgtca atgtcgagat aattgaactg | 2280 |
| caaacgatac ctaccttaaa cggagcagaa cacatcaaga agcaattagg tgtgtcgtac | 2340 |
| gttagcaagt agttcgcgag gaggaataaa atag | 2374 |

<210> SEQ ID NO 13
<211> LENGTH: 1194
<212> TYPE: DNA
<213> ORGANISM: Anopheles gambiae

<400> SEQUENCE: 13

| | |
|---|---|
| atgaagtttg aactgtttca aaaatattcc tccccggaca cggtcttatc cttcgtgcta | 60 |
| aggcttttgc atatcgtggg catgaatggg gcaggatttc ggtcgcgaat tcgagttggt | 120 |
| ggcattttc tgttctattt aatctttctt gtaataccgc cactaacggg cgggtacacc | 180 |
| gatggtcacc agcgtgtacg caccagtgtg gaattcctgt ttaattgcaa tatttacggc | 240 |
| ggcagtatgt tctttgccta cgatgtggcc actttccaag cgttcatcca ggaactgaag | 300 |
| agcctttcgg ttttggtatg ctcacattcg tacagactaa agtataagct gacccggttc | 360 |
| aaccgtcgag cggatattat cgccaaagtc caaacgacct gcatgggtgc tgtaacgctt | 420 |
| ttctactgga ttgcaccgat accttccatc tgtgcgcact actacaggtc gaccaattcc | 480 |

-continued

```
accgaacccg tgcggtttgt gcaacattta gaggtgaagt tctattggct cgagaatcgc    540
acctcagtcg aggactacat aaccttcgtg ctgatcatgc tacccgtcgt ggttatgtgt    600
ggttacgtat gcaatttgaa ggtgatgacc atctgctgca gcattggaca ctgtacactg    660
tacaccagga tgactataga gatggtagag cagttggaaa gcatggcatc agcggaacga    720
actgccagcg ccatacgcaa cgtggggcag atgcacagtg gtttactgaa atgcattagg    780
cttttgaaca cgtcaatccg atcgatgctg atgctgcagt ggttgacctg cgtgttaaac    840
tggagcattt ctctcatcta tctaacgaac gtgggcatct cgctacaatc ggttaccgtg    900
gtggtaatgt tttttcttgc cactgcggaa actttcctgt attgtttact gggacgcgg    960 cttgcgacac aacagcagct gctggagcac gcactctatg ctacacggtg gtacaactac   1020
ccaatagcct ttcgcagcag cattaggatg atgttgagac agtcgcaaag gcatgcacac   1080
ataacggtgg ggaagttttt tcgcgttaat ttggaagaat ttagcaggat tgtcaactta   1140
tcctactctg cttacgtcgt acttaaggat gtaataaaga tggatgtaca gtga         1194
```

<210> SEQ ID NO 14
<211> LENGTH: 412
<212> TYPE: PRT
<213> ORGANISM: Anopheles gambiae

<400> SEQUENCE: 14

```
Met Lys Phe Glu Leu Phe Gln Lys Tyr Ser Ser Pro Asp Thr Val Leu
  1               5                  10                  15

Ser Phe Val Leu Arg Leu Leu His Ile Val Gly Met Asn Gly Ala Gly
                 20                  25                  30

Phe Arg Ser Arg Ile Arg Val Gly Gly Ile Phe Leu Phe Tyr Leu Ile
             35                  40                  45

Phe Leu Val Ile Pro Pro Leu Thr Gly Gly Tyr Thr Asp Gly His Gln
         50                  55                  60

Arg Val Arg Thr Ser Val Glu Phe Leu Phe Asn Cys Asn Ile Tyr Gly
     65                  70                  75                  80

Gly Ser Met Phe Phe Ala Tyr Asp Val Ala Thr Phe Gln Ala Phe Ile
                 85                  90                  95

Gln Glu Leu Lys Ser Leu Ser Val Leu Val Cys Ser His Ser Tyr Arg
            100                 105                 110

Leu Lys Tyr Lys Leu Thr Arg Phe Asn Arg Arg Ala Asp Ile Ile Ala
        115                 120                 125

Lys Val Gln Thr Thr Cys Met Gly Ala Val Thr Leu Phe Tyr Trp Ile
    130                 135                 140

Ala Pro Ile Pro Ser Ile Cys Ala His Tyr Tyr Arg Ser Thr Asn Ser
145                 150                 155                 160

Thr Glu Pro Val Arg Phe Val Gln His Leu Glu Val Lys Phe Tyr Trp
                165                 170                 175

Leu Glu Asn Arg Thr Ser Val Glu Asp Tyr Ile Thr Phe Val Leu Ile
            180                 185                 190

Met Leu Pro Val Val Met Cys Gly Tyr Val Cys Asn Leu Lys Val
        195                 200                 205

Met Thr Ile Cys Cys Ser Ile Gly His Cys Thr Leu Tyr Thr Arg Met
    210                 215                 220

Thr Ile Glu Met Val Glu Gln Leu Glu Ser Met Ala Ser Ala Glu Arg
225                 230                 235                 240

Thr Ala Ser Ala Ile Arg Asn Val Gly Gln Met His Ser Gly Leu Leu
                245                 250                 255
```

```
Lys Cys Ile Arg Leu Leu Asn Thr Ser Ile Arg Ser Met Leu Met Leu
                260                 265                 270

Gln Trp Leu Thr Cys Val Leu Asn Trp Ser Ile Ser Leu Ile Tyr Leu
            275                 280                 285

Thr Asn Val Gly Ile Ser Leu Gln Ser Val Thr Val Val Met Phe
        290                 295                 300

Phe Leu Ala Thr Ala Glu Thr Phe Leu Tyr Cys Leu Leu Gly Thr Arg
305                 310                 315                 320

Leu Ala Thr Gln Gln Gln Leu Leu Glu His Ala Leu Tyr Ala Thr Arg
                325                 330                 335

Trp Tyr Asn Tyr Pro Ile Ala Phe Arg Ser Ser Ile Arg Met Met Leu
                340                 345                 350

Arg Gln Ser Gln Arg His Ala His Ile Thr Val Gly Lys Phe Phe Arg
                355                 360                 365

Val Asn Leu Glu Glu Phe Ser Arg Ile Val Asn Leu Ser Tyr Ser Ala
            370                 375                 380

Tyr Val Val Leu Lys Asp Val Ile Lys Met Asp Val Gln Asn Val Ser
385                 390                 395                 400

Tyr Ser Tyr Phe Thr Leu Leu Arg Arg Val Tyr Asn
                405                 410

<210> SEQ ID NO 15
<211> LENGTH: 1176
<212> TYPE: DNA
<213> ORGANISM: Anopheles gambiae

<400> SEQUENCE: 15
atggtgctac cgaagctgtc cgaaccgtac gccgtgatgc cgcttctact acgcctgcag      60
cgtttcgttg gctgtggggg tgaacgacgc tatcgctaca agttccggtt ggcattttta    120
agcttctgtc tgctagtagt tattccgaag gttgccttcg ctatccaga tttagagaca     180 atggttcgcg gaacagctga gctgattttc gaatggaacg tactgtttgg gatgttgctg    240 tttctctca gctagacga ctatgatgat ctggtgtacc ggtacaagga catatcaaag      300
attgctttcc gtaaggacgt tccctcgcag atgggcgact atctggtacg catcaatcat    360
cgtatcgatc ggttttccaa gatctactgc tgcagccatc tgtgtttggc catcttctac    420
tgggtggctc cttcgtccag cacctaccta gcgtacctgg gggcacgaaa cagatccgtc    480
ccggtcgaac atgtgctaca cctggaggag gagctgtact ggtttcacac ccgcgtctcg    540
ctggtagatt actccatatt caccgccatc atgctgccta caatctttat gctagcgtac    600
ttcggtggac taaagctgct aaccatcttc agcaacgtga agtactgttc ggcaatgctc    660
aggcttgtgg cgatgagaat ccagttcatg gaccggctgg acgagcgcga agcggaaaag    720
gaactgatcg aaatcatcgt catgcatcag aaggcgctaa aatgtgtgga gctgttggaa    780
atcatctttc ggtgggtttt tctgggacag ttcatacagt gcgtaatgat ctggtgcagc    840
ttggttctgt acgtcgccgt tacgggtctc agcacaaaag cggcaaacgt gggtgtactg    900
tttatactgc taacagtgga aacctacgga ttctgctact ttggcagtga tcttacctcg    960
gaggcaagtt gttattcgct gacacgtgct gcgtacggta gcctctggta tcgccgttcg   1020
gtttcgattc aacggaagct tcgaatggta ctgcagcgtg cccagaaacc ggtcggcatc   1080
tcggctggga agttttgctt cgtcgacatt gagcagtttg gcaatatggc aaaaacatca   1140
tactcgttct acatcgttct gaaggatcaa ttttaa                              1176
```

<210> SEQ ID NO 16
<211> LENGTH: 391
<212> TYPE: PRT
<213> ORGANISM: Anopheles gambiae

<400> SEQUENCE: 16

```
Met Val Leu Pro Lys Leu Ser Glu Pro Tyr Ala Val Met Pro Leu Leu
  1               5                  10                  15

Leu Arg Leu Gln Arg Phe Val Gly Leu Trp Gly Glu Arg Arg Tyr Arg
             20                  25                  30

Tyr Lys Phe Arg Leu Ala Phe Leu Ser Phe Cys Leu Leu Val Val Ile
         35                  40                  45

Pro Lys Val Ala Phe Gly Tyr Pro Asp Leu Glu Thr Met Val Arg Gly
     50                  55                  60

Thr Ala Glu Leu Ile Phe Glu Trp Asn Val Leu Phe Gly Met Leu Leu
 65                  70                  75                  80

Phe Ser Leu Lys Leu Asp Asp Tyr Asp Asp Leu Val Tyr Arg Tyr Lys
                 85                  90                  95

Asp Ile Ser Lys Ile Ala Phe Arg Lys Asp Val Pro Ser Gln Met Gly
            100                 105                 110

Asp Tyr Leu Val Arg Ile Asn His Arg Ile Asp Arg Phe Ser Lys Ile
        115                 120                 125

Tyr Cys Cys Ser His Leu Cys Leu Ala Ile Phe Tyr Trp Val Ala Pro
    130                 135                 140

Ser Ser Ser Thr Tyr Leu Ala Tyr Leu Gly Ala Arg Asn Arg Ser Val
145                 150                 155                 160

Pro Val Glu His Val Leu His Leu Glu Glu Glu Leu Tyr Trp Phe His
                165                 170                 175

Thr Arg Val Ser Leu Val Asp Tyr Ser Ile Phe Thr Ala Ile Met Leu
            180                 185                 190

Pro Thr Ile Phe Met Leu Ala Tyr Phe Gly Gly Leu Lys Leu Leu Thr
        195                 200                 205

Ile Phe Ser Asn Val Lys Tyr Cys Ser Ala Met Leu Arg Leu Val Ala
    210                 215                 220

Met Arg Ile Gln Phe Met Asp Arg Leu Asp Glu Arg Glu Ala Glu Lys
225                 230                 235                 240

Glu Leu Ile Glu Ile Ile Val Met His Gln Lys Ala Leu Lys Cys Val
                245                 250                 255

Glu Leu Leu Glu Ile Ile Phe Arg Trp Val Phe Leu Gly Gln Phe Ile
            260                 265                 270

Gln Cys Val Met Ile Trp Cys Ser Leu Val Leu Tyr Val Ala Val Thr
        275                 280                 285

Gly Leu Ser Thr Lys Ala Ala Asn Val Gly Val Leu Phe Ile Leu Leu
    290                 295                 300

Thr Val Glu Thr Tyr Gly Phe Cys Tyr Phe Gly Ser Asp Leu Thr Ser
305                 310                 315                 320

Glu Ala Ser Cys Tyr Ser Leu Thr Arg Ala Ala Tyr Gly Ser Leu Trp
                325                 330                 335

Tyr Arg Arg Ser Val Ser Ile Gln Arg Lys Leu Arg Met Val Leu Gln
            340                 345                 350

Arg Ala Gln Lys Pro Val Gly Ile Ser Ala Gly Lys Phe Cys Phe Val
        355                 360                 365

Asp Ile Glu Gln Phe Gly Asn Met Ala Lys Thr Ser Tyr Ser Phe Tyr
    370                 375                 380
```

Ile Val Leu Lys Asp Gln Phe
385              390

<210> SEQ ID NO 17
<211> LENGTH: 474
<212> TYPE: DNA
<213> ORGANISM: Anopheles gambiae

<400> SEQUENCE: 17
ttatgcttac cggatgttgc gatcgcgcac gtgcttttcc gcatacgcca gtgcacactt      60
gatggcggtg gtgatgacgt ctgctgcgca ccgttttctg ctcgtgagtc agaccttttc     120
atttcctgca atatcctgtt tctttcccga ccccacagac ggttagacgg atatatgctg     180
gtaaagtttg tcctcttcat gctgtgcttt ctgatcgagc tgctgatgct gtgtgcgtac     240
ggtgaggata ttgtggaatc gccttggggt gattgatgcc gcttacggtt gcgaatggta     300
ccgggaaggg tcgtggcgt tccatcgatc cgtgctgcaa attatacacc gcagccagca     360
gtccgtcata ctgaccgcat ggaaaatttg gcccatccaa atgagtactt tcagtcagat     420
cctgcaagct tcctggtcct actttaccct cctgaagacc gtctacggga ataa           474

<210> SEQ ID NO 18
<211> LENGTH: 157
<212> TYPE: PRT
<213> ORGANISM: Anopheles gambiae

<400> SEQUENCE: 18

Leu Cys Leu Pro Asp Val Ala Ile Ala His Val Leu Phe Arg Ile Arg
 1               5                  10                  15

Gln Cys Thr Leu Asp Gly Gly Gly Asp Val Cys Cys Ala Pro Phe
            20                  25                  30

Ser Ala Arg Glu Ser Asp Leu Phe Ile Ser Cys Asn Ile Leu Phe Leu
        35                  40                  45

Ser Arg Pro His Arg Arg Leu Asp Gly Tyr Met Leu Val Lys Phe Val
    50                  55                  60

Leu Phe Met Leu Cys Phe Leu Ile Glu Leu Leu Met Leu Cys Ala Tyr
65                  70                  75                  80

Gly Glu Asp Ile Val Glu Ser Pro Trp Gly Asp Glx Cys Arg Leu Arg
                85                  90                  95

Leu Arg Met Val Pro Gly Arg Val Gly Gly Val Pro Ser Ile Arg Ala
            100                 105                 110

Ala Asn Tyr Thr Pro Gln Pro Ala Val Arg His Thr Asp Arg Met Glu
        115                 120                 125

Asn Leu Ala His Pro Asn Glu Tyr Phe Gln Ser Asp Pro Ala Ser Phe
    130                 135                 140

Leu Val Leu Leu Tyr Pro Pro Glu Asp Arg Leu Arg Glu
145                 150                 155

<210> SEQ ID NO 19
<211> LENGTH: 1206
<212> TYPE: DNA
<213> ORGANISM: Anopheles gambiae

<400> SEQUENCE: 19
atggtgctga tccagttctt cgccatcctc ggcaacctgg cgacgaacgc ggacgacgtg      60
aacgagctga ccgccaacac gatcacgacc ctgttcttca cgcactcggt caccaagttc     120
atctactttg cggtcaactc ggagaacttc taccggacgc tcgccatctg gaaccagacc     180

```
aacacgcacc cgctgtttgc cgaatcggac gcccggtacc attcgattgc gctcgccaag      240
atgcggaagc tgctggtgct ggtgatggcc accaccgtcc tgtcggttgt cgcctgggtt      300
acgataacat ttttcggcga gagcgtcaag actgtgctcg ataaggcaac caacgagacg      360
tacacggtgg atatacccCg gctgcccatc aagtcctggt atccgtggaa tgcaatgagc      420
ggaccggcgt acatttttctc tttcatctac caggtacgtt ggcggaatgg tattatgcga     480
tcgttgatgg agctttcggc ctcgctggac acctaccggc ccaactcttc gcaactgttc      540
cgagcaattt cagccggttc caaatcggag ctgatcatca cgaagaaaa ggatccggac       600 gttaaggact ttgatctgag cggcatctac agctcgaagg cggactgggg cgcccagttc      660
cgtgcgccgt cgacgctgca aacgttcgac gagaatggca ggaacggaaa tccgaacggg      720
cttacccgga agcaggaaat gatggtgcgc agcgccatca agtactgggt cgagcggcac      780
aagcacgttg tacgtctcgt ttcagcaatc ggagatacgt acggtcctgc cctgctgcta      840
cacatgctga cctccaccat caagctgacg ctgctcgcct accaggcaac gaaaatcgac      900
ggtgtcaacg tgtacggatt gaccgtaatc ggatatttgt gctacgcgtt ggctcaggtt      960
ttcctgtttt gcatctttgg caatcggctc atcgaggaga gctcatccgt gatgaaggcg     1020
gcctattcct gccactggta cgacgggtcc gaggaggcaa aaaccttcgt ccagatcgtt     1080
tgtcagcagt gccagaaggc gatgactatt tccggagcca agttttttcac cgtttcgctc     1140 gatctgtttg cttcggttct tggagccgtt gtcacctact tcatggtgct ggtgcagctg     1200
aagtaa                                                                 1206
```

<210> SEQ ID NO 20
<211> LENGTH: 401
<212> TYPE: PRT
<213> ORGANISM: Anopheles gambiae

<400> SEQUENCE: 20

```
Met Val Leu Ile Gln Phe Phe Ala Ile Leu Gly Asn Leu Ala Thr Asn
  1               5                  10                  15

Ala Asp Asp Val Asn Glu Leu Thr Ala Asn Thr Ile Thr Thr Leu Phe
                 20                  25                  30

Phe Thr His Ser Val Thr Lys Phe Ile Tyr Phe Ala Val Asn Ser Glu
             35                  40                  45

Asn Phe Tyr Arg Thr Leu Ala Ile Trp Asn Gln Thr Asn Thr His Pro
         50                  55                  60

Leu Phe Ala Glu Ser Asp Ala Arg Tyr His Ser Ile Ala Leu Ala Lys
 65                  70                  75                  80

Met Arg Lys Leu Leu Val Leu Val Met Ala Thr Thr Val Leu Ser Val
                 85                  90                  95

Val Ala Trp Val Thr Ile Thr Phe Phe Gly Glu Ser Val Lys Thr Val
            100                 105                 110

Leu Asp Lys Ala Thr Asn Glu Thr Tyr Thr Val Asp Ile Pro Arg Leu
        115                 120                 125

Pro Ile Lys Ser Trp Tyr Pro Trp Asn Ala Met Ser Gly Pro Ala Tyr
    130                 135                 140

Ile Phe Ser Phe Ile Tyr Gln Val Arg Trp Arg Asn Gly Ile Met Arg
145                 150                 155                 160

Ser Leu Met Glu Leu Ser Ala Ser Leu Asp Thr Tyr Arg Pro Asn Ser
                165                 170                 175

Ser Gln Leu Phe Arg Ala Ile Ser Ala Gly Ser Lys Ser Glu Leu Ile
```

```
                    180              185              190
Ile Asn Glu Glu Lys Asp Pro Asp Val Lys Asp Phe Asp Leu Ser Gly
            195                  200              205
Ile Tyr Ser Ser Lys Ala Asp Trp Gly Ala Gln Phe Arg Ala Pro Ser
        210                  215                  220
Thr Leu Gln Thr Phe Asp Glu Asn Gly Arg Asn Gly Asn Pro Asn Gly
225                  230                  235                  240
Leu Thr Arg Lys Gln Glu Met Met Val Arg Ser Ala Ile Lys Tyr Trp
                245                  250                  255
Val Glu Arg His Lys His Val Val Arg Leu Val Ser Ala Ile Gly Asp
            260                  265                  270
Thr Tyr Gly Pro Ala Leu Leu Leu His Met Leu Thr Ser Thr Ile Lys
        275                  280                  285
Leu Thr Leu Leu Ala Tyr Gln Ala Thr Lys Ile Asp Gly Val Asn Val
    290                  295                  300
Tyr Gly Leu Thr Val Ile Gly Tyr Leu Cys Tyr Ala Leu Ala Gln Val
305                  310                  315                  320
Phe Leu Phe Cys Ile Phe Gly Asn Arg Leu Ile Glu Glu Ser Ser Ser
                325                  330                  335
Val Met Lys Ala Ala Tyr Ser Cys His Trp Tyr Asp Gly Ser Glu Glu
            340                  345                  350
Ala Lys Thr Phe Val Gln Ile Val Cys Gln Gln Cys Gln Lys Ala Met
        355                  360                  365
Thr Ile Ser Gly Ala Lys Phe Phe Thr Val Ser Leu Asp Leu Phe Ala
    370                  375                  380
Ser Val Leu Gly Ala Val Val Thr Tyr Phe Met Val Leu Val Gln Leu
385                  390                  395                  400

Lys

<210> SEQ ID NO 21
<211> LENGTH: 2272
<212> TYPE: DNA
<213> ORGANISM: Anopheles gambiae

<400> SEQUENCE: 21
tctagacttg aacccatgac gggcatttta ttgagtcgtt cgagttgacg actgtaccac     60
gggaccaccc gtttatcact atcactatta attaattata atatgctttt gtagcgatca    120
gcctaccggg ttttgtttct ctggatatct taagttccca tttgattatc aagatagaac    180
aacaacttgt accttaaata atcattacgt acccttaatc aacctgtgca tcaaggagtt    240
ttcgcgaaag caaaaatccg attgtctgat gttgtcttga ttccatccga ttcgttactg    300
gttctgcaaa atcgtccaat aatacggcaa tgtccttatc gatgcttgaa tcaacatcac    360
attgtttgca tttcgttttt tgcgtgcaaa tatgttattt gcaaagaagg caaggtaatg    420
tgcttaagag taaatacaat tcgctgtcca tttttgtcc accagtgtgc cagaacccgt    480
gccttttagt ccttcgaata catccgacca gtcagcaagc aagtgcatca tggtgctacc    540
gaagctgtcc gaaccgtacg ccgtgatgcc gcttctacta cgcctgcagc gtttcgttgg    600
gctgtggggt gaacgacgct atcgctacaa gttccggttg cattttttaa gcttctgtct    660
gctagtagtt attccgaagg ttgccttcgg ctatccagat ttagagacaa tggttcgcgg    720
aacagctgag ctgattttcg aatggaacgt actgtttggg atgttgctgt tttctctcaa    780
gctagacgac tatgatgatc tggtgtaccg gtacaaggac atatcaaaga ttggtgcgtg    840
```

```
ataatgattg ataaaaggaa cctttgagca actcctatcc ctttcaagct ttccgtaagg    900
acgttccctc gcagatgggc gactatctgg tacgcatcaa tcatcgtatc gatcggtttt    960
ccaagatcta ctgctgcagc catctgtgtt tggccatctt ctactgggtg gctccttcgt   1020
ccagcaccta cctagcgtac ctgggggcac gaaacagatc cgtcccggtc gaacatgtgc   1080
tacacctgga ggaggagctg tactggtttc acacccgcgt ctcgctggta gattactcca   1140
tattcaccgc catcatgctg cctacaatct ttatgctagc gtacttcggt ggactaaagc   1200
tgctaaccat cttcagcaac gtgaagtact gttcggcaat gctcaggctt gtggcgatga   1260
gaatccagtt catggaccgg ctggacgagc gcgaagcgga aaaggaactg atcgaaatca   1320
tcgtcatgca tcagaaggcg ctaaagtaag gtctgccggt atgttgtgga tagaatacat   1380
ttctagctgc tttcagatgt gtggagctgt tggaaatcat ctttcggtgg ttttttctgg   1440
gacagttcat acagtgcgta atgatctggt gcagcttggt tctgtacgtc gccgttacgg   1500
taactaaaag cactgtagtg atctgtctgc cacaccattc actgctgtgt cttgttttgt   1560
cactcttccc agggtctcag cacaaaagcg gcaaacgtgg gtgtactgtt tatactgcta   1620
acagtggaaa cctacggatt ctgctacttt ggcagtgatc ttacctcgga ggcaagttgt   1680
tattcgctga gtttcagtta ctttccgtt ccctctaac cgtaccactt gtaccatttg   1740
tttgagacag agcttgagcg tagcacgtgc tgcgtacggt agcctctggt atcgccgttc   1800
ggtttcgatt caacggaagc ttcgaatggt actgcagcgt gcccagaaac cggtcggcat   1860
ctcggctggg aagttttgct tcgtcgacat tgagcagttt ggcaatgtat ggggagacct   1920
tccactgtgg caagaaagat tttctttatt aatgcatctt ttaatttaca gatggcaaaa   1980
acatcatact cgttctacat cgttctgaag gatcaatttt aaaggggaac tcccccaccc   2040
gaccagacga cggaaagcta acgatgtgca attgaatagt cattagtagc gttttttgctc   2100
gcaaacgaac taacccttg acttttaag ttcactacgg tgaggacaaa atcaataaa   2160
ttaaatcgag accgttgatg agcaaaagaa aaaaaatat tttactgatt ttcatttcgt   2220
tccatcgact acataatcat aattatatgc cacattttat tataagtttt tg   2272
```

<210> SEQ ID NO 22
<211> LENGTH: 931
<212> TYPE: DNA
<213> ORGANISM: Anopheles gambiae

<400> SEQUENCE: 22

```
aacacccatc ttatcggcaa aattagtatt taccgtttga aagcggcttc ccttcctggc     60
tgtttctcac tctctctctc tctgtctctc ttattgatgc cgtatgcgcc gcgtgctata    120
ggctagttat gcttaccgga tgttgcgatc gcgcacgtgc ttttccgcat acgccagtgc    180
acacttgatg gcggtggtga tgacgtctgc tgcgcaccgt tttctgctcg tgagtcagac    240
cttttcattt cctgcaatat cctgtttctt tcccgacccc acagacggtt agacggatat    300
atgctggtaa agtttgtcct cttcatgctg tgctttctga tcgagctgct gatgctgtgt    360
gcgtacggtg aggatattgt ggaatcggta aggcaccagg cggtgatgag cgagtcgcga    420
gtaattgaag cttttgcttt taaaacacat cagagccttg gggtgattga tgccgcttac    480
ggttgcgaat ggtaccggga agggtcggtg gcgttccatc gatccgtgct gcaaattata    540
caccgcagcc agcagtccgt catactgacc gcatggaaaa tttggcccat ccaaatgagt    600
actttcagtc aggtgagttg ccaattgatt gccgtttgcg ttaatatttc agtaagagtg    660
cgctcttttcc cttagatcct gcaagcttcc tggtcctact ttaccctcct gaagaccgtc    720
```

```
tacgggaata agtaagcgcg agagagagag agagagcagt atcgttcacc ctttggatga    780
atcaatagat ttctaatcat gaaccattga aaaatgaatc aacattttcg ctagttgcac    840
aatattgtac cattctatac agcttcacca cgaccaagcg tttgttgcat caggaccaaa    900
cacgtttcga caagccgcgt cacctgctgg c                                   931

<210> SEQ ID NO 23
<211> LENGTH: 11103
<212> TYPE: DNA
<213> ORGANISM: Anopheles gambiae

<400> SEQUENCE: 23
ccgcccgggc aggtgactta cgcggtctga cttgctggtg cgctgctttg tacggcaaac     60
ggctacacaa gcgaatcgaa ttatttttcct atcacgctgc gcttaccagc gcctgctggt   120
aggcaaagaa tgtgcaaagt ttcatttggc ttggttcgtc tgctttgctg tgaacgtgtg    180
cacggttgca tcgctaaggt ttcggtgtga gccgagaagt tgcagatcga aatctctttg    240
tgtgtgtgtg tgtgtgtgca gtgggaagca ttgtgtttag tgagaagtga aaagaaaagt    300
gctgaaaaat gcaagtccag ccgaccaagt acgtcggcct tcgttgccga cctgatgccg    360
aacattcggg ttgatgcagg ccagcggtca actttctgtt ccggctacgt caccggcccg    420
atactgatcc gcaaggtgta ctcctggtgg acgctcgccc atggtgctga tccagttctt    480
cgccatcctc ggcaacctgg cgacgaacgg ggacgacgtg aacgagctga ccgccaacac    540
gatcacgacc ctgttcttca cgcactcggt caccaagttc atctactttg cggtcaactc    600
ggagaacttc taccggacgc tcgccatctg gaaccagacc aacacgcacc cgctgtttgc    660
cgaatcggac gcccggtacc attcgattgc gctcgccaag atgcggaagc tgctggtgct    720
ggtgatggcc accaccgtcc tgtcggttgt cggtatgtgt gtatgtgtgt ggccgtttgg    780
gaaagtgtct ttgcggcaga accccaatct actgttacgc ttgactgggt ttttgttttt    840
ttctcggtgg agggacggga taaaatatct gaaagaataa ttgagtcaac ccacaggggg    900
atgcaagaca tcgcaggcag agagtttggg tttgatttat caccgcacac cgaatatctt    960
cacggttcat aagcttcacc gcggtgaaaa gggaactccc catttccctg ttttcttttt   1020
tttcttcctc tcgataaatt actcatcgct tttcgttttt tttttttgt tgttgcttct   1080 ttcttctttc atccctacta gcctgggtta cgataacatt tttcggcgag agcgtcaaga   1140
ctgtgctcga taaggcaacc aacgagacgt acacggtgga tatacccccgg ctgcccatca   1200 agtcctggta tccgtggaat gcaatgagcg gaccggcgta catttctctt ttcatctacc   1260
aggtacgttg gcggaatgtc ctgcgcgtca cagttggcag tcagtgagcg gcaacacggc   1320
gaaaaaatgg gactaaaacc ggtcttcaca gagccaacac attcctacag caattgcata   1380
ccttcgggcg gtcgggactg ggcaatgcag ctacaacatc ctcgcctaaa gttatgcaat   1440
tcgagcgaca aatgttgccg tgttagggct ttttgtgata atagtcgttt ttttgtcctc   1500
tcgcttatca aactctatca acggaggaaa tccattttcg ctacaatgcc tacagctcaa   1560 gttttcaaggt caatcgagcg ggtggggatc aactttttta ttcattttgc taacgcccca   1620
tcaacaaatt ctatgttctc aatggcaaag attactgccc gcaccaatcg cccaacgaaa   1680
cggcaaaaga aaagcgacga ttatgaagat gtccaaacca ttgcccgccc gacgctttat   1740
ctgatgattt gcgggatggc ttttacttgt ctgctacttt caggcacaaa aggaaatgaa   1800
accagcgcag gctcgtttgc cggcttgcgg aggttcttca ggcactgagg ctgagtactt   1860
```

-continued

```
aaatcgaacg attttttacga ttctggatcc agtttttatga tgtggcctgc attacagtgg    1920
caattatacc ctgatgttca tttcattgca ttttgtaagt ttgtgctggt aacgcccgta    1980
acgattaatt cttttcaaag agattctttc aaagagattc aaaatgtgta aacaaatgc     2040
taacgaatgg accgtacttg gagggttgcg gaaagtaacg ttttaaaata ttcatcacaa    2100
tcctctgcaa acttgtgctt aattaattgg tgcacaataa gtttaaactg tggcggcaga    2160
tgtgtcgctg tccgcttcct tccttcccag caagctcgtg cgaataatt tattccatca     2220
ttttaataca gccgtttgtg cattttaatt agcaaagcaa tataaaaagc agctaaccat    2280
ccccattaaa acaaagtgct tccgggccca attgttatgg cggtggaaag taatggtttt    2340
accagtggaa gtgtcctttc ccatcgtggg tacttcgcga tattcttgtc ttatacaagt    2400
gcatacagaa aaaaggaca atcctcctt gctatggtct aaggccagct tcggtaccgc      2460
ttccgcttcg ggatgtcata agtttgatg ggtgttttta acattacttc cgctcttaac     2520
cacctaatgg acttttcatg cttgagctaa agttaaacca gccaccagcg gtacgcaccg    2580
agccacggtt gatttcggcg gcggcctcat ccccagtttt gcgccaccaa tattgccttc    2640
attaatctgt accctcggag cgttagggcc cgcggacgag tcctcgttgt aatgcaccgc    2700
catgccacgg gacgggataa tccgttggga cggcgcgaaa gcgactatcg cggacggatt    2760
ggttcgaccg tgctacaaca cattttatgc ttcacagatt tacttcctgc tgttttcgat    2820
ggtccagagc aacctcgcgg atgtcatgtt ctgctcctgg ttgctgctag cctgcgagca    2880
gctgcaacac ttgaaggtag gtacggtagc aaacgtggtt gtcttttacat ccgcgtgcag   2940
cattatcctt atcgacgtgt agtgttaacg gtaaagagg aagcgataaa aaagcaacat     3000
tctctcacac cctcgatctc tctttatttt ctctctctct ctctctctct ctctctctct    3060
ctctctctct ctctctctct ctctccatct cctcgggcag ggtattatgc gatcgttgat    3120
ggagctttcg gcctcgctgg acacctaccg gcccaactct tcgcaactgt tccgagcaat    3180
ttcagccggt tccaaatcgg agctgatcat caacgaaggt atgtgaaacg tgtgctcgtg    3240
gcagacggac tcaaagagag cataacacaa tcccctggta gttcatttca atgaccttaa    3300
cactcggcaa gctaagcgag acagtgggga cagtgagaaa gagagaacaa gaaaaaaaac    3360
catcatccgt acgacatcat cgctacgtac cggtatttca ggatgaggaa ataaaacgct    3420
aggggaatga aagtgcgaca gaatgataaa acaatcccca cccaggcccc cagcctggac    3480
gaacggatgt agtgtgcgaa gcgagcaaaa aaagtcaaat aaattgaagt ttaaaaatag    3540
atttttcccg tccatccgtg gtggagcgta aagcccggcg gacaacttcg agcacggcga    3600
ccgtgcacag tactgtgcca cagttgtagg gacggataag ctccgttcct tttttatcct    3660
ttttttttgg agatttgttt gcgttcgcat cgttagacga gcttagtgcc gtgttgctct    3720
aattgctatt tattataaag cgcttccaaa tagaagatcg gttctctcca tttaatctat    3780
cgcgcctgta cgcctgaaac tatgcactgt gctgtgaaac cgtcaagctc gagcacgacg    3840
aatggcccac cgtaccacgc ccgtggtgcc caaagcgcaa cgcgaattgc atgttaacaa    3900
acctttgcct accatccaat ccgtgtgaaa ttgcccgctc tctttctctc ttttgcgctt    3960
tcggtgtatc gaacggtttt gtcccttttt tttactttgc tcttgatctc ttgctgtgct    4020
cactttcatc tcatgttttg cctgacggtg gtgggttttc gaaaaagag cgatttcttc     4080
tgcgtgtgtg tgtggtttttt ttaaataacc gctccaggtc gtgttgaacg ctgcaggacc    4140
gatcggagct agtttattat cagctttagt gtttatccca cccatgcccc acatcacgtc    4200
tgtggagagt gggggaagct taagtccaat gtaatttacc gtgtttctgt cgttcgtcac    4260
```

-continued

| | |
|---|---|
| cttcttcgtc gatggagatt ggtgcggttg gcacgataaa agcccactgc acgttacgga | 4320 |
| ccgagggaaa ggtcttttg taggcctagc aacggtcctc attcaccgca tgggggtgta | 4380 |
| gctcagatgg tagagcgctc gcttagcatg tgagaggtac cgggatcgat acccggcatc | 4440 |
| tccaacccac acaaaacgtt ttttaagaag atttttaggg aagatattaa cgcgggtaca | 4500 |
| ctgtgctcct ctaagttgga agagtagatg agatgatgac aagggagaag gaacatgtgt | 4560 |
| acgtgtttga tagcaaacac acaaacaaca atatcatctc tgataataat ctgatgtgtg | 4620 |
| atgtgtgtgt attgttgtta tgctgccttt gccatcttgt ccctctctct cctgttcaac | 4680 |
| tcctaaaaga attgtttgga gtcctctcag ttcctcgtaa agatcctttc gagattcttc | 4740 |
| tttccttttt attatttatt ccacgagcct ctgacataag tagccttccg cttatttcct | 4800 |
| tctccttgca cttgtcagtt ccgtgtagag cgtcattttg aggtttacac atttcccacc | 4860 |
| gacgcctgat tgttacattg tcatctacat tgctttccgt ttaccgttcc gccctttttt | 4920 |
| tttaacgcta ccacagaaaa ggatccggac gttaaggact ttgatctgag cggcatctac | 4980 |
| agctcgaagg cggactgggg cgcccagttc cgtgcgccgt cgacgctgca aacgttcgac | 5040 |
| gagaatggca ggaacggaaa tccgaacggg cttacccgga agcaggaaat gatggtgcgc | 5100 |
| agcgccatca agtactgggt cgagcggcac aagcacgttg tacggtaggt atggtaattt | 5160 |
| ctaaggtgtg gtgtaaagcc tccaggttcc atgaaaagg gatactttac cacagtaaga | 5220 |
| gtttgttttg ctggacttac attctttgga gcattgtttg gtgttgtgct gaaaccggtt | 5280 |
| gcaatatcgt tttgcgaaga aattatgtgt aaagcgtatt acaatctcat tcctctgtta | 5340 |
| atctgtacca attgtgtcag ccccgaccga aagcaggcct aattcgtacc agaaaaacca | 5400 |
| caagctgttt gtaagcatcg atacgcccga agctttcaat ccagccaagg cgccacctac | 5460 |
| tattgacgtg acttttttgca cgttcacact ctccctctcc cattctttct ataaccaatc | 5520 |
| gtcgctcagc cagcatcgcc cggagtgaag ttttttattg aacgatatca cccgtatcga | 5580 |
| ttttccacta aacatgctta aatcgtttca caaagctccc ccaaaatccc atttcaccaa | 5640 |
| tccaccaatt tgaagtccgt cgtcctttgt gtccttgtgt ttgtgtgttt gtgtgagctg | 5700 |
| gagacatggg ggagtgagta accgaacaac ctcttgccgc tgcttcacga tatcgaacag | 5760 |
| caccaagata agcatccctt tttccctagc cgatgtctcc gatatctcga ttccgcttcc | 5820 |
| agcgaggcaa agaaaaaggc gaactggctg acctcacccg gggcgaggaa aaagcgtagg | 5880 |
| gattacgtcg agcagcacga gttgtgattt cttcttcttc tggttccata aatcgctgac | 5940 |
| ggtttccatt accgcctgcg gagtgcacac acgtgaaggg aaagcgaaaa cgtttagatt | 6000 |
| ccagcagcaa cggcagcacc agaagcagca gcagcgcggc aaattgaatc atcctgacgc | 6060 |
| gatgagttgt ctgggttttc gggtcggtgg cttacagcac cacaccatct gctgcagcta | 6120 |
| atacagctgt aaatttcgtt agacatagac ttgattttac aatattacac acacacttac | 6180 |
| acacacagct atagatttgt cgcttggcgt atggctctgt acggcgtgcc gtacatgccg | 6240 |
| cgagccgtgt tgctgctggt tgcgatacga atcacgtccg attcgattca gcctgcgtgt | 6300 |
| ttttggtgaa gatccttatc ggtgacccac tttcagtgtg tcgagagcga gggtcactat | 6360 |
| ggcgcctgtc agtggaaag ctaggctcga ttcaaagggc cattgtgcca gtgttctttt | 6420 |
| taagatagcg ataagctttt gatcgaaata gtaaatcaaa cattgtttct ttttttcctat | 6480 |
| tccaaactgt tgccaacctc attattacgt ttttgcagcg ggtgtatagt aaattgcata | 6540 |
| cttttaaggcg tgattttcaa atgtagcgtt ccgtatgcag aaacgccatg gattatgcaa | 6600 |

```
tttaaacaat gctgcttcct taacattcaa ataacggctt attaaggaac tttttgtgca    6660
atttgttttt aacagcaaat agttagctca gaacgatcac atttagtatc gcttcaacaa    6720
agaactcttt taaacacaca atttgtaatg ccattccctc gagaaagttt cttgtcagtc    6780
ctcctctgca tcacagcaac aaccaaacct gctcatgttt cctgctcgtt tcctagctgt    6840
tttgaacgtt atttccgatt cctgtgcttg cccgcttttc ttacaatcaa ccacaatggt    6900
tcagatttcg ctcttatttt attgacccac tgctttcgtg ctgaagcccg tggaaacaat    6960
gcgccaagct cagcatccag ccatgcatgt aaaatgagcc acgcgacaga ttttagacat    7020
cgctttcgct ctgcaccgga ggtggtttta ttcttgtttc cgattccac gtccattcgt    7080 cctgggtccg tccgccgggc ccgaaaccgt aagccgtgcg gggaattacg caatcgaaac    7140
gagccagaaa atgagcacgc caaatgcaaa gaaaatcccc ttttgagtgg tgctcctgcc    7200
accactcatc tccccaactg gtgggtgaaa aaccttgtgc gccccttctc tttccagaaa    7260
aaaaacgcct cgctcgcaca aaaacatgct cgcccggtga agctgcgtat gtcgcagaag    7320
ctcaaaccaa cgccgccagc aagcatcaac aatttctatt caaacaccca acgcagcgcc    7380
caaaccgggt gcactgtact cagtagcgaa gatgctcaga ttgtcccgtg cgctgctttc    7440
gatgcccgtt tcggagcggg aagccatcgc ttgccaacgt tggcgatgtc ttttagccgt    7500
ggatttgaat ttctgaata tcacaggcgg gcgcggtttg cctgcaaggt tgttgcttcc    7560
cacacgagca ttgctttccg taccgcggtg gggcgagttt tcaacgcaac cttctacaag    7620
caacgccaca acgcctggga gcgatattta acagaaacaa gaacatcccg aacttcagca    7680
catgccgtga tttgcctgtt ggaaaagctt ttgtgagcgt gtgagttgaa cgagctctat    7740
tttcccagcg atgggtggca tttgtgtggc atgctatcgt cagcttttct tgaatcttta    7800
cctctccatt cgcctccatt agtacacgcg tatggaaaat gggtgcaacg gatcagaacg    7860
gattttccgc gacagactta ataaagggaa agcaacgcgt tttttgcatg tgtagtgttt    7920
atgagcttta tgccgttact ttgcaattaa aaatagcaaa aaataacagt ttttttttgt    7980
aagcggatta caaagaatgt atcagaatat tacgtgaaac attcatttca tgctgttaac    8040
gctcaaatag aatagttttg taacacggat tgcataccct gccggtatcg gttacatttt    8100
cgcctaacag tatgcaatct gtttagcttt gttgtttaat gactgcgttg gtagtacaat    8160
atttatttac accgcgtaat ttatctcaca aattgcaaaa aaatgtcaat ctgtatcgat    8220
tattcacaca aatcagatcc cggaaccagt gtagcccaat gtgctcttat tgaattacca    8280
cgaacaaatc aacctgatgc ccgggtccgt tggcaaacag cttgcgccga agccgctcag    8340
tgtttcgtgc actaccgtgc tgccatttttg ctgccctcat cgaacagata aacagaaggg    8400
caactcttgt gagcatcgca atgcccgtct gaagttccgt cgaaaatggg cctaaattca    8460
atttgacgca tttacccgcg aacaattgcg cgaaggctgt caagtgtgtt ccacgaactg    8520
cgacaacaag cacacacaca aacacaaatg ttatcgtttc ggcatgtttc tcggtacaaa    8580
gcgtgtggcg ctatgtggca tgccgattcc cagacagagt gatcgatagt aaatgtagcc    8640
tatccggtag cattcaattt cctttctat cctcgcaaac aaagcccatt ctggggaggc    8700
gtggtgaagc tttcaaaggc attgtgaaac aaatgtcctg gttcggaggg atgctgggga    8760
aagcaaacac ggtgccgcca tcgctgctac cgtcaatcga tcatgcatga tgtgattaat    8820
atttgtgtta ttcacctgcg tatctatgcg tccgtcgtgt cgttcggatt tccggaagtc    8880
aaggaaaaag cgactccatt tgggattggt ttttgcagcg aaaaatcaaa acattcgcac    8940
aaaaccgtcc tccatttcaa atgcctacac ttgtcactgt atatctctct ttctctcgtt    9000
```

-continued

```
ttgccacgtt gcagtctcgt ttcagcaatc ggagatacgt acggtcctgc cctgctgcta    9060
cacatgctga cctccaccat caagctgacg ctgctcgcct accaggcaac gaaaatcgac    9120
ggtgtcaacg tgtacggatt gaccgtaatc ggatatttgt gctacgcgtt ggctcaggtt    9180
ttcctgtttt gcatctttgg caatcggctc atcgaggagg tacgtgcgct cggcgtgttg    9240
ccgtgggaaa gcattctccc tgccccatat cgcttcattc tcccagatca cacatttgca    9300
tcacaaagcc agcacacttt tgcttcgccg ctgccatctc ggcttctgaa tgttttcact    9360
tctcccatac ttctcccgtg cagagctcat ccgtgatgaa ggcggcctat tcctgccact    9420
ggtacgacgg gtccgaggag gcaaaaacct tcgtccagat cgtttgtcag cagtgccaga    9480
aggcgatgac tatttccgga gccaagtttt tcaccgtttc gctcgatctg tttgcttcgg    9540
taagtgtagc ctggtggctg gcacagaaca ggctggcaaa acagggactt tggctctagc    9600
ctgatgggtg gtatatgtgt gtctatttttt gctaccatt ctcgcatccc ttcctttcca    9660
ggttcttgga gccgttgtca cctacttcat ggtgctggtg cagctgaagt aaacagccgt    9720
ggcccggaag gatgtgtttt ttttcgctcg ttcggttgtt tgtttgtgca cactttctct    9780
tggacatttt ctctactgca aaggtttaac aaacagcaac aacaaataat cccaagtttt    9840
cttttacaga tctttgcaaa atgattagat tttaatagat taacagtgct tgattatctg    9900
tcctgtagca accggggctg aagaacgttg atttggtaaa agtacaaaag ggacgttgga    9960
aattgaacca ccagaagagt gatatttatg caaagctcac caaggaaat ctatgtatgt   10020 gtgatttgcg ctcatcaagc actgtatgtg cctttcaact agtgcagcaa taagagtac   10080 aaatgtttct tagcgcaccg tacattgtcg tttcggcgtt ttaaccgttg ttgataatac   10140 acaaagatg ataaaataa ataataacaa aatgttaata tgagtaagta ctaaatagag   10200
aaatcgtttt agtatgatca tacctccaat catttgtttg aaattaactt taattttaac   10260
tcaaattaaa ccgatgtttt actttctgtg agaattattg tggaagaact taatggaagt   10320
ataattaaat tgattgctaa ctttatgcgt ttttcaattt acgaacgcta gtcttcaaac   10380
atcgcttcaa aagtattact accacattat tcatttactt atagttatat ttattgcctc   10440
ttcatctttc catggccaga actactgcag aaaagcttct tttttgctcg ctttccgatg   10500
gttggttgga cgaagttggt aacaaacggc aagcaattag cataaactat tttcgcatcg   10560
agatggaaat gaatgtacca ctagaaccga gtgaaatgaa ttacttttca acttgcacgc   10620
caaaaccatt atctaaagta cgcacaactt aaaaacaaac cccaaattgt cgtccaccct   10680
tcattccact ttcttgctac actttccgac cgagttctgt agcgccagca gcaaaaaaat   10740
acatataaaa ccttcatcac tcaagctgta tcgagccagc gtgggttgtg tttgactgtg   10800
ctgtgaaaga aagaagaaaa aaaaaacact tccacgggaa gctagcaatt ggaaatgcat   10860
aaattaaccg gaagaaattc gcaaaacccc gcaccgacgt accgcaccgc atccgtaccg   10920
ataccggaac aaacggtgtg cgcgaaagaa tccgctagca gccccactgg cacgggtatt   10980
tgcttttggt tctgtgtttt tcttccactg gtttgggtgc ctgggcgaag gctagctcgg   11040
ctactttccc ggggccgcaa ttttctgcag cccaaggcgg cgtgctcgtg gggccaaaag   11100
aat                                                                 11103
```

<210> SEQ ID NO 24
<211> LENGTH: 5543
<212> TYPE: DNA
<213> ORGANISM: Anopheles gambiae

<400> SEQUENCE: 24

```
ggtaaagggc tggatgagga gaggagactt atattttgg aagcctttgg taggtgacaa      60
ggggagtta gtgataggg agtggggcca aatagggag gaggtaaaat ttatggtacg       120
ccccataggg gaagaggaaa gtgaccagag caggccagtg tccccgctgg ggggctcaac    180
ggtgagccgg ctgtccctcg gcgggggaat gaaaccctta caaaataaaa actagcgttt    240
ttctactctc tcaaatgtcc aaagctgttg ctcaactggg tgctgaaaac ccctgcgtta    300
tgcaaagcat tagtcagctg aaggtgcaaa atcttccaca gcttgcataa aggagctgct    360
gatccgtagc ttgtccgtgc aagatcatac gatctttata attcgcaaat tcgccttccc    420
ttcttaatcc tttatgacgc ccgtgttggt tcgctctttc ctgcgacaca cggtgctcag    480
ccaaacgtga cctaaacacg caccccacag cgtacgcgtg acgtcacgac cttttgcgtt    540
ttcgcggga aataagatta acgttcgctg ccgacgcccg ttgaccgttg catcgtaatt     600
tcgtataccg ttctgcgcgt gtaccctgc gtacgtccag gctgttgcgt atcgcaccat     660
cgtacgcgaa cggaaggcat cggggaaagg gacgcaagga tgggcatgaa ttagctgaca   720
ctatttgtcc cctccccgt aatgcaggcg caacccctg gcagtcgtc ggtggcagta      780
gctcgagcct aattcagtta atggcaatcg ggcaagcgtc gatcgatttt cccgctgcaa    840
aagcccgcac gskkwysgtc cgggaaacct tttcggtgtt ttcagtgtac ggtccaccac    900
acgggcggta aaaggtata aaactgtcca ccagccgacc gttcgatcgc acttctggtt    960
gttctttcaa accatacaat acccgaaact agctgagaac tttgtagttc aagcaattga   1020
aaaaacgcaa gaaaacagcg ctccgtagaa cgaccccgga gaatagacac gcaattttgt   1080
acgaccaatc tcgaagcgag tgaattgagg gagtgagcta ccgtgtgtga gaatactcgt   1140
gatacatttc gaaagttcta tctgattgtt tgctctgtgt ttgcgaagac acaaactaac   1200
gcgcagtgat ggttgtcgca gtgaaagtgt ttaaaaaatc cgccccgaat ggcaaactga   1260
ccgtctatct cggcaagcgt gacttcatcg accacaccga ctactgtgac ccgatcgatg   1320
gcgttatcgt gctggacgag gagtacctgc gaggccgcaa ggtcttcggc caggttggtt   1380
tactggaaga tctcgatcct cgatgactgc agttcaggaa gtctttaaga acttgttaag   1440
tgamcagata tgattctttc gagtgtctac ttactagatg agtgaatatg tgtgcaattt   1500
ggaatgaact ctcaaatgcc tggagcagaa gcagagtatc gataacttgg aattacaatc   1560
aagcctcgtt aattagccaa tactcatgtt gccatgttct gaatttatca gatctttgaa   1620
aggttcgagg atattatgaa gataatagtg cagacggcca atacaaagga cctattatcg   1680
ttctattgct gaaccacaat gttacagcgt tgatgaata tcatccgatt agtttcaata   1740
caatccaatt agtgaggtga catactagaa ggacacacaa ctgatgtcat aatgtagttg   1800
aaatgaatgc taatatcaag ggtattaaag gtttttaatg aactccaact cattggataa   1860
ctctttcgaa gaactttgat gtctcagaat agccgaattc ttatctttta ctaacatagt   1920
tgcaagttct cagcatgtaa ctgttctcca acccacttca atgttccatt tctctctctc   1980
tctctctctc tctccccgca gctcatcacc acctaccgct atggccggga agaggatgag   2040
gtgatgggcg tgaagttctc caaggagatg gtgctgacca aggaacagat ctacccgatg   2100
gagaacgcca acatggagat gacgcccatg caggagcggc tggtgaagaa gctgggcgcg   2160
aacgcgttcc cgttcacctt ccacttcccg agcatggcgc cgagctcggt gacgctgcag   2220
gccggtgagg acgacacggg caaaccgctc ggcgtcgagt acgcgatcaa ggcgcacgtc   2280
ggcgaggacg agagcgacaa gggccacaag cgcagcgccg tcacgctgac gatcaagaag   2340
```

```
ctccagtacg cgccggtgtc ccgcggtcgt cgtcttcctt cgtcgctcgt cagcaagggc    2400
ttcaccttct cgcagggcaa gatcaacctg gaggtaacgc tcgatcggga gatctactac    2460
cacggcgaga agattgcggc caacatcgtc gtgacgaaca actcgcgcaa gactgtcaag    2520
agcatcaagt gcttcgttgt gcagcactgt gaggttagta gtgatggagc attcctggga    2580 ggggcacct agatgtgatg atcgggttaa tttaactccc taatcattcc ctcctgcatt    2640
ytaggtcagc gatggtgaat gcacagttca gcaagcacat cgcctcgctg gagacscscg    2700
agggttgccc gatcacgccc ggggcgagct tcacgaaatc gttcttcctg gtcccgctcg    2760
cctccagcaa caaggaccgc cggggcattg cgctcgacgg ccacctgaag gaggatgacg    2820
tcaacctggc ctcgtccacg ctgatcagcg agggcaagtg tccgtcggat gcgatgggta    2880
ttgtcatctc gtactcgctg cgcgtcaagc tcaattgtgg cacgctcggt ggcgaactcc    2940
agacggacgt accgttcaag ctgatgaacc cagcacctgg taagtgtcgt aagggagcga    3000
acttcgtaca tcatcgaata tctggtgcta atgcatattt ttttcctatt tctctattat    3060
caggatctgt cgagcgagag cgcgtgaacg ccctgaagaa gatgaagtcg atagagcgtc    3120
accgttacga gaactcgcac tacgccgacg atgacgacaa catcgtgttc gaagactttg    3180
cccgcctgcg gatgaacgag ccggagtaag cctgtcccgc ctgatgcggc attcacykrc    3240
aaccatcctt caccccaagg gcgaacggct ttaatccgga gaggggacag caaatgccat    3300
gtcttctgtt ccatttcctc caccgagcac ccgagcaggc agcaaacgca acatgaaga    3360 aaacacacac gccccaaaaa tcctcccaat gcttttccgc gccaagtatg ctttctttca    3420 tgcccttttta atgctcccag gagcggtacg agcgtgcgtg tgatggctgg gcggggacga    3480
acgagtgtcc ctcgggggga cccttcgtct aggctagcgg ctagagtggt ggtcacctga    3540
gagacgctca tcagcctttc ccagccgtaa ccacacgtaa cmatgtccaa tgtgataaca    3600
ctgatgatgc tatttaaatt attaaacgca aaaaacacgg cgccgctaag caacgaacac    3660
tagagcgcgc gataaggaaa cagcaagaag aagaagaaga agaagtagta gagaaaaaac    3720
ctatctagtg aaggaacaac ctaccctata agtgctcccc caaaaactat aacgatatat    3780
gaagtaacga gagaaaaacg acatgaaaat gaggagtgtt aatggtagcc tccgccaaaa    3840
aacaaacaaa cgactaacga agccaaaacc cccttcctaa aatcacaaca agcaaactaa    3900
cgattatgaa atggtcaaca ccaaatagac aacaaatttg attcatcgat taattccctg    3960
ccggagaaac tgtgccgaga gttcccgag aagaaaacca gaacatcaac gactgcgcag    4020
tcaagaggtg gggcaacgcg aaccagcaac tcccttggga atgcagaatc cccaactggg    4080
ggtgcgatgg ttacaatcct cctcaatcga agaacacgca catgagtaac gtgcagcaat    4140
taatcgatca atcgaagagc aacttacatc gaaaaatgtt taaaaacgaa caaaaaaaa    4200 tatcataacc atacacaaga accaagcccc aaaamcccaa gcaaacacca gaagtgaacg    4260
aaatcgacga taatctagtg cagctccggk tcgtacgtgg acgcttttcc ccggkttggc    4320
tatggtgraa accggccmca tccgaaccgc tggcgacagc agccttagag tgtaagacgt    4380
tttatgtttc tgttttgttt ttcgtggtga gacagcaatt ggagcaggca atttaaggga    4440
aacgagcaaa cgatttaggc aaatggaagc tagaagcaac aaagacgcgc gcagaggaag    4500
aaaaaaacag acaagaagat aaaaacaaaa ccacacgagc aatgaatgca acgaatgcgg    4560
ttgggaagtg aagagctaag gaaaacggtg cggagaaatg gacatgaaga tgtcctttc    4620 ccggtaccgt tttcacttcc gattcattca ccccaactcg ttcagcgctc cttactgcga    4680
```

```
gtcaattatt gtttcagatt gtgttcgatt ggttgatata agcttgttca tgcaaaatgg      4740 gggttttct  tatctaagga aaccatgcta tattattacc tgcaaatgca ataggaacag      4800
agcagaaagg aaactttata atcmactaaa atywaaccma attaattgga aaagagaaaa      4860
aaaacccaca acttcaaacc aatgcaacga cctattgata catttgaaac aaacccaaag      4920
gtcacgcaac acatagagtc agttttgagt tttgcgatgt acagtggact gttagtagct      4980
gtgtttattt tgtataaatc taattggct atgttattat tgtaattgga gaaaaatgc       5040 tgagcaacca aaaaaaaact aacttacaaa caaaccagca actattgaat ttgttttat      5100 ttgttccaat ttgtactgtt ttttcaggtt tcttttttg cgtttggtcg ggaggctttc       5160
ggccaacggt ccacaggtag tagaggggga aagaaataac tggttgatgg aagaaaaaaa     5220
aaaagcaacc cttaccctaa ctctttgtaa agatatgtat acgaatgcac cggtatttgc      5280
tcaattagaa tgtattccct ttttgctgga agatagggga aggattggga tggaccgttt      5340
tctgtttcta gagaacaatt tactgcaacg agtgtgatat caaggatgt gataatgcat       5400 tttccagcag agagttggag ttggcactat tgtgattgta atttgaaact ttgaaactat       5460
tacaaatacc aaactttcct tataaagggg gaaattctga aagaaaaat catatttcac       5520 cccagttggg ctaaaaccat ttg                                             5543
```

<210> SEQ ID NO 25
<211> LENGTH: 398
<212> TYPE: PRT
<213> ORGANISM: Anopheles gambiae

<400> SEQUENCE: 25

```
Met Val Ala Val Lys Val Phe Lys Lys Ser Ala Pro Asn Gly Lys
  1               5                  10                  15

Leu Thr Val Tyr Leu Gly Lys Arg Asp Phe Ile Asp His Thr Asp Tyr
             20                  25                  30

Cys Asp Pro Ile Asp Gly Val Ile Val Leu Asp Glu Glu Tyr Leu Arg
         35                  40                  45

Gly Arg Lys Val Phe Gly Gln Leu Ile Thr Thr Tyr Arg Tyr Gly Arg
     50                  55                  60

Glu Glu Asp Glu Val Met Gly Val Lys Phe Ser Lys Glu Met Val Leu
 65                  70                  75                  80

Thr Lys Glu Gln Ile Tyr Pro Met Glu Asn Ala Asn Met Glu Met Thr
                 85                  90                  95

Pro Met Gln Glu Arg Leu Val Lys Lys Leu Gly Ala Asn Ala Phe Pro
            100                 105                 110

Phe Thr Phe His Phe Pro Ser Met Ala Pro Ser Ser Val Thr Leu Gln
        115                 120                 125

Ala Gly Glu Asp Asp Thr Gly Lys Pro Leu Gly Val Glu Tyr Ala Ile
    130                 135                 140

Lys Ala His Val Gly Glu Asp Glu Ser Asp Lys Gly His Lys Arg Ser
145                 150                 155                 160

Ala Val Thr Leu Thr Ile Lys Lys Leu Gln Tyr Ala Pro Val Ser Arg
                165                 170                 175

Gly Arg Arg Leu Pro Ser Ser Leu Val Ser Lys Gly Phe Thr Phe Ser
            180                 185                 190

Gln Gly Lys Ile Asn Leu Glu Val Thr Leu Asp Arg Glu Ile Tyr Tyr
        195                 200                 205

His Gly Glu Lys Ile Ala Ala Asn Ile Val Val Thr Asn Asn Ser Arg
    210                 215                 220
```

```
Lys Thr Val Lys Ser Ile Lys Cys Phe Val Gln His Cys Glu Val
225                 230                 235                 240

Thr Met Val Asn Ala Gln Phe Ser Lys His Ile Ala Ser Leu Glu Thr
            245                 250                 255

Arg Glu Gly Cys Pro Ile Thr Pro Gly Ala Ser Phe Thr Lys Ser Phe
                260                 265                 270

Phe Leu Val Pro Leu Ala Ser Ser Asn Lys Asp Arg Arg Gly Ile Ala
            275                 280                 285

Leu Asp Gly His Leu Lys Glu Asp Asp Val Asn Leu Ala Ser Ser Thr
290                 295                 300

Leu Ile Ser Glu Gly Lys Cys Pro Ser Asp Ala Met Gly Ile Val Ile
305                 310                 315                 320

Ser Tyr Ser Leu Arg Val Lys Leu Asn Cys Gly Thr Leu Gly Gly Glu
                325                 330                 335

Leu Gln Thr Asp Val Pro Phe Lys Leu Met Asn Pro Ala Pro Gly Ser
            340                 345                 350

Val Glu Arg Glu Arg Val Asn Ala Leu Lys Lys Met Lys Ser Ile Glu
            355                 360                 365

Arg His Arg Tyr Glu Asn Ser His Tyr Ala Asp Asp Asp Asn Ile
370                 375                 380

Val Phe Glu Asp Phe Ala Arg Leu Arg Met Asn Glu Pro Glu
385                 390                 395

<210> SEQ ID NO 26
<211> LENGTH: 1190
<212> TYPE: DNA
<213> ORGANISM: Anopheles gambiae

<400> SEQUENCE: 26
atggttgtcg cagtgaaagt gtttaaaaaa tccgccccga atggcaaact gaccgtctat      60
ctcggcaagc gtgacttcat cgaccacacc gactactgtg acccgatcga tggcgttatc     120
gtgctggacg aggagtacct gcgaggccgc aaggtcttcg ccagctcat caccacctac      180 cgctatggcc gggaagagga tgaggtgatg ggcgtgaagt ctccaagga gatggtgctg      240 accaaggaac agatctaccc gatggagaac gccaacatgg agatgacgcc catgcaggag     300
cggctggtga agaagctggg cgcgaacgcg ttcccgttca ccttccactt cccgagcatg     360
gcgccgagct cggtgacgct gcaggccggt gaggacgaca cgggcaaacc gctcggcgtc     420
gagtacgcga tcaaggcgca cgtcggcgag acagagcga caagggccac aagcgcagcg     480
ccgtcacgct gacgatcaag aagctccagt acgcgccggt gtcccgcggt cgtcgtcttc     540
cttcgtcgct cgtcagcaag gcttcacct tctcgcaggg caagatcaac ctggaggtaa      600
cgctcgatcg ggatctacta ccacggcgag aagattgcgg ccaacatcgt cgtgacgaac     660
aactcgcgca agactgtcaa gagcatcaag tgcttcgttg tgcagcactg tgaggttaca     720
tggtgaatgc acagttcagc aagcacatcg cctcgctgga gcgcgcgag ggtgcccgat      780 cacgcccggg gcgagcttca cgaaatcgtt cttcctggtc ccgctcgcct ccagcaacaa     840
ggaccgccgg gcattgcgct cgacggccac ctgaaggagg atgacgtcaa cctggcctcg     900
tccacgctga tcagcgaggg caagtgtccg tcggatgcga tgggtattgt catctcgtac     960
tcgctgcgcg tcaagctcaa ttgtggcacg ctggtggcga actccagacg gacgtaccgt    1020
tcaagctgat gaacccagca cctggatctg tcgagcgaga gcgcgtgaac gccctgaaga    1080
agatgaagtc gatagagcgt caccgttacg agaactcgca ctacgccgac gatgacgaca    1140
```
acatcgtgtt cgaagactttt gcccgcctgc ggatgaacga gccggagtaa                1190

<210> SEQ ID NO 27
<211> LENGTH: 401
<212> TYPE: PRT
<213> ORGANISM: Drosophila melanogaster

<400> SEQUENCE: 27

```
Met Val Val Ser Val Lys Val Phe Lys Lys Ala Thr Pro Asn Gly Lys
  1               5                  10                  15

Val Thr Phe Tyr Leu Gly Arg Arg Asp Phe Ile Asp His Ile Asp Tyr
             20                  25                  30

Cys Asp Pro Val Asp Gly Val Ile Val Glu Pro Asp Tyr Leu Lys
         35                  40                  45

Asn Arg Lys Val Phe Gly Gln Leu Ala Thr Thr Tyr Arg Tyr Gly Arg
     50                  55                  60

Glu Glu Asp Glu Val Met Gly Val Lys Phe Ser Lys Glu Leu Ile Leu
 65                  70                  75                  80

Cys Arg Glu Gln Ile Val Pro Met Thr Asn Pro Asn Met Glu Met Thr
                 85                  90                  95

Pro Met Gln Glu Lys Leu Val Arg Lys Leu Gly Ser Asn Ala Tyr Pro
            100                 105                 110

Phe Thr Phe His Phe Pro Pro Asn Ser Pro Ser Ser Val Thr Leu Gln
        115                 120                 125

Gln Glu Gly Asp Asp Asn Gly Lys Pro Leu Gly Val Glu Tyr Thr Ile
130                 135                 140

Arg Ala Phe Val Gly Asp Ser Glu Asp Asp Arg Gln His Lys Arg Ser
145                 150                 155                 160

Met Val Ser Leu Val Ile Lys Lys Leu Gln Tyr Ala Pro Leu Asn Arg
                165                 170                 175

Gly Gln Arg Leu Pro Ser Ser Leu Val Ser Lys Gly Phe Thr Phe Ser
            180                 185                 190

Asn Gly Lys Ile Ser Leu Glu Val Thr Leu Asp Arg Glu Ile Tyr Tyr
        195                 200                 205

His Gly Glu Lys Thr Ala Ala Thr Val Gln Val Ser Asn Asn Ser Lys
    210                 215                 220

Lys Ser Val Lys Ser Ile Lys Cys Phe Ile Val Gln His Thr Glu Ile
225                 230                 235                 240

Thr Met Val Asn Ala Gln Phe Ser Lys His Val Ala Gln Leu Glu Thr
                245                 250                 255

Lys Glu Gly Cys Pro Ile Thr Pro Gly Ala Asn Leu Thr Lys Thr Phe
            260                 265                 270

Tyr Leu Ile Pro Leu Ala Ala Asn Asn Lys Asp Arg His Gly Ile Ala
        275                 280                 285

Leu Asp Gly His Leu Lys Asp Glu Asp Val Asn Leu Ala Ser Ser Thr
    290                 295                 300

Met Val Gln Glu Gly Lys Ser Thr Gly Asp Ala Cys Gly Ile Val Ile
305                 310                 315                 320

Ser Tyr Ser Val Arg Ile Lys Leu Asn Cys Gly Thr Leu Gly Gly Glu
                325                 330                 335

Met Gln Thr Asp Val Pro Phe Lys Leu Leu Gln Pro Ala Pro Gly Thr
            340                 345                 350

Ile Glu Lys Lys Arg Ser Asn Ala Met Lys Lys Met Lys Ser Ile Glu
        355                 360                 365
```

-continued

```
Gln His Arg Asn Val Lys Gly Tyr Tyr Gln Asp Asp Asp Asn Ile
    370                 375                 380

Val Phe Glu Asp Phe Ala Lys Met Arg Met Asn Asn Val Asn Met Ala
385                 390                 395                 400

Asp
```